(12) United States Patent
Rubin et al.

(10) Patent No.: US 10,202,615 B2
(45) Date of Patent: Feb. 12, 2019

(54) MAMMALIAN GENES INVOLVED IN TOXICITY AND INFECTION

(75) Inventors: Donald Rubin, Nashville, TN (US); Dana Borden Lacy, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 212 days.

(21) Appl. No.: 13/992,972

(22) PCT Filed: Dec. 11, 2011

(86) PCT No.: PCT/US2011/064297
§ 371 (c)(1),
(2), (4) Date: Apr. 23, 2014

(87) PCT Pub. No.: WO2012/102793
PCT Pub. Date: Aug. 2, 2012

(65) Prior Publication Data
US 2014/0242692 A1    Aug. 28, 2014

Related U.S. Application Data

(60) Provisional application No. 61/421,750, filed on Dec. 10, 2010, provisional application No. 61/495,193, filed on Jun. 9, 2011.

(51) Int. Cl.
| | | |
|---|---|---|
| *C12N 15/85* | (2006.01) | |
| *A61K 31/7088* | (2006.01) | |
| *C12N 15/70* | (2006.01) | |
| *C12N 15/74* | (2006.01) | |
| *C12N 15/81* | (2006.01) | |

(52) U.S. Cl.
CPC .......... *C12N 15/85* (2013.01); *A61K 31/7088* (2013.01); *C12N 15/70* (2013.01); *C12N 15/74* (2013.01); *C12N 15/815* (2013.01); *Y02A 50/465* (2018.01)

(58) Field of Classification Search
CPC ....................................................... C12N 15/85
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,704,692 A | 11/1987 | Ladner |
| 4,816,567 A | 3/1989 | Cabilly et al. |
| 4,965,188 A | 10/1990 | Mullis et al. |
| 4,980,286 A | 12/1990 | Morgan et al. |
| 5,556,752 A | 9/1996 | Lockhart et al. |
| 5,578,832 A | 11/1996 | Trulson et al. |
| 5,593,839 A | 1/1997 | Hubbell et al. |
| 5,599,695 A | 2/1997 | Pease et al. |
| 5,631,734 A | 5/1997 | Stern et al. |
| 5,859,308 A | 1/1999 | Mirochnitchenko et al. |
| 5,898,221 A | 4/1999 | Mizuhara et al. |
| 6,107,094 A | 8/2000 | Crooke |
| 6,281,408 B1 | 8/2001 | Khillan |
| 6,376,743 B1 | 4/2002 | Yanagimachi |
| 6,448,000 B1 | 9/2002 | Rubin et al. |
| 6,506,559 B1 | 1/2003 | Fire et al. |
| 6,573,099 B2 | 6/2003 | Graham |
| 6,777,177 B1 | 8/2004 | Rubin et al. |
| 6,867,349 B2 | 3/2005 | Ekker et al. |
| 7,056,704 B2 | 6/2006 | Tuschl et al. |
| 7,078,196 B2 | 7/2006 | Tuschl et al. |
| 7,105,495 B2 | 9/2006 | Agrawal et al. |
| 7,115,579 B2 | 10/2006 | Agrawal et al. |
| 7,176,296 B2 | 2/2007 | Agrawal et al. |
| 7,230,096 B2 | 6/2007 | Nilsson et al. |
| 7,262,489 B2 | 8/2007 | Shoji |
| 7,329,648 B2 | 2/2008 | Agrawal |
| 2001/0044937 A1 | 11/2001 | Schatten et al. |
| 2002/0066117 A1 | 5/2002 | Nilsson et al. |

FOREIGN PATENT DOCUMENTS

| | | |
|---|---|---|
| EP | 0721016 A2 | 7/1996 |
| EP | 0728520 A1 | 8/1996 |
| EP | 0785280 A2 | 7/1997 |
| EP | 0799897 A1 | 10/1997 |
| EP | 1144623 A1 | 10/2001 |
| WO | WO-88/09810 A1 | 12/1988 |
| WO | WO-89/10134 A1 | 11/1989 |
| WO | WO-90/11364 A1 | 10/1990 |
| WO | WO-95/06764 A2 | 3/1995 |
| WO | WO-95/22058 A1 | 8/1995 |
| WO | WO-97/02357 A1 | 1/1997 |
| WO | WO-97/27317 A1 | 7/1997 |
| WO | WO-97/29212 A1 | 8/1997 |
| WO | WO-01/43540 A2 | 6/2001 |
| WO | WO-02/19811 A2 | 3/2002 |
| WO | WO-02/44321 A2 | 6/2002 |
| WO | PCT/US2011/064297 | 12/2011 |
| WO | WO-2012/102793 A2 | 8/2012 |

OTHER PUBLICATIONS

Drudy et al., 2007, Int. J. Infectious Diseases, vol. 11, pp. 5-10.*
Drudy et al. (2007, Emerging Infectious Diseases, vol. 13(3), pp. 504-505).*
Ambrosini et al. (Aug. 1, 2009, Cancer Research, vol. 69(15), pp. 6115-6121).*
"PCR Methods and Applications" (1991, Cold Spring Harbor Laboratory Press).
Bashkin, J.K., et al. 1995. "Ribozyme mimics as catalytic antisense reagents," Appl. Biochem Biotechnol. 54, 43-56.
Bray, M., et al. 2000. "Cidofovir protects mice against lethal aerosol or intranasal cowpox virus challenge," J. Infect. Dis., 181(1), 10-19.
Caplen et al. 2001. "Specific inhibition of gene expression by small double-stranded RNAs in invertebrate and vertebrate systems," Proc. Natl. Acad. Sci. 98(17):9742-9747.

(Continued)

*Primary Examiner* — Thaian N Ton
*Assistant Examiner* — David A. Montanari
(74) *Attorney, Agent, or Firm* — Ballard Spahr LLP

(57) ABSTRACT

The present invention relates to cellular proteins that are involved in toxicity and infection or are otherwise associated with the life cycle of one or more pathogens.

6 Claims, No Drawings

Specification includes a Sequence Listing.

(56) References Cited

OTHER PUBLICATIONS

Chang et al. 2004. "Using siRNA technique to generate transgenic animals with spatiotemporal and conditional gene knockdown." American Journal of Pathology 165, 1535-1541.
Chee, M., et al. 1996. "Accessing genetic information with high-density DNA arrays," Science 274(5287), 610-14.
Elbashir, S.M., et al. 2001. "Duplexes of 21-nucleotide RNAs mediate RNA interference in cultured mammalian cells," Nature, 411:494-8.
Gautier et al. 1987. "Alpha-DNA. IV: Alpha-anomeric and beta-anomeric tetrathymidylates covalently linked to intercalating oxazolopyridocarbazole. Synthesis, physiochemical properties and poly (rA) binding," Nucl. Acids Res. 15:6625-41.
Gitlin, L., et al.. 2002. "Short interfering RNA confers intracellular antiviral immunity in human cells," Nature, 418:430-4.
Goodman et al. 1994. "Recombinant adeno-associated virus-mediated gene transfer into hematopoietic progenitor cells," Blood 84:1492-1500.
Hacia, J.G., et al. 1996. "Detection of heterozygous mutations in BRCA1 using high density oligonucleotide arrays and two-colour fluorescence analysis," Nature Genetics 14(4), 441-47.
Harlow and Lane. 1988. Antibodies, A Laboratory Manual. Cold Spring Harbor Publications, New York, 1988.
Hartl, D.L. & Clark, A.G., Principles of Population Genetics, Third Edition (Sinauer Associates, Inc., Sunderland Massachusetts, 1997).
Inoue, H., et al. 1987. "Sequence-dependent hydrolysis of RNA using modified oligonucleotide splints and RNase H.," FEBS Lett. 215, 327-30.
Inoue et al. 1987. "Synthesis and hybridization studies on two complementary nona(2'O-methyl)ribonucleotides," Nucl. Acids Res. 15:6131-48.
Joliot et al. 1991. "Antennapedia homeobox peptide regulates neural morphogenesis," Proc. Natl. Acad Sci USA, 88:1864-8.
Jones, P.T., et al. 1986. "Replacing the complementarity-determining regions in a human antibody with those from a mouse," Nature, 321, 522-525.
Kaur, H. et al. 2006. "Thermodynamic, counterion, and hydration effects for the incorporation of locked nucleic acid nucleotides into DNA duplexes," Biochemistry 45(23), 7347-55.
Kehl-Fie & St. Geme. 2006. "Identification and characterization of an RTX toxin in the emerging pathogen Kingella kingae," J. Bacteriol. 189(2):430-6.
Kirby. 2004. "Anthrax lethal toxin induces human endothelial cell apoptosis," Infection and Immunity, 72:430-439.
Klimpel et al. 2008. "Levofloxacin rescues mice from lethal intranasal infections with virulent Francisella tularensis and induces immunity and production of protective antibody," Vaccine 26(52), 6874-82.
Kozel, M.J., et al. 1996. "Extensive polymorphisms observed in HIV-1 clade B protease gene using high-density oligonucleotide arrays," Nature Medicine 2(7), 753-59.
Kuiken et al. 2003. "Pathology of human influenza A (H5N1) virus infection in cynomolgus macaques (*Macaca fascicularis*)," Vet. Pathol. 40(3), 304-10.
Lam, K.S., et al. 1991. "A new type of synthetic peptide library for identifying ligand-binding activity," Nature 354(6348), 82-4.
Lemaitre et al. 1987. "Specific antiviral activity of a poly(L-lysine)-conjugated oligodeoxyribonucleotide sequence complementary to vesicular stomatitis virus N protein mRNA initiation site," Proc. Natl. Acad. Sci. USA, 84:648-52.
Letsinger et al. 1989. "Cholesteryl-conjugated oligonucleotides: synthesis, properties, and activity as inhibitors of replication of human immunodeficiency virus in cell culture," Proc. Natl. Acad. Sci USA, 86:6553-6.
Li et al. 2005. "Specific inhibition of HIV-1 replication by short hairpin RNAs targeting human cyclin T1 without inducing apoptosis." FEBS Lett.,579(14), 3100-6.
Li et al., 2008. "Galectin-3 is a negative regulator of lipopolysaccharide-mediated inflammation," J. Immunol., 181(4):2781-9.

Lockhart , D.J., et al. 1996. "Expression monitoring by hybridization to high-density oligonucleotide arrays," Nature Biotechnology 14, 1675-80.
Lowy et al. 2010. "Treatment with monomlonal antibodies against Clostridium difficle toxins," N. Engl. J. Med. 21:362(3):197-205.
Maines et al. 2005. "Avian influenza (H5N1) viruses isolated from humans in Asia in 2004 exhibit increased virulence in mammals," J. Virol. 79(18):11788-11800.
Miller et al. 1986. "Redesign of retrovirus packaging cell lines to avoid recombination leading to helper virus production," Mol. Cell. Biol. 6:2895.
Naidini, L., et al. 1996. "In vivo gene delivery and stable transduction of nondividng cells by a lentiviral vector," Science 272(5259), 263-267.
Niles, A. et al. 2007. "A homogeneous assay to measure live and dead cells in the same sample by detecting different protease markers," Anal. Biochem. 366, 197-206.
Nilsson, U.J., et al. 1997. "Immobilization of reducing sugars as toxin binding agents," Bioconjugate Chem., 8(4), 466-471.
Ottolini et al. 2005. "The cotton rat provides a useful small-animal model for the study of influenza virus pathogenesis," J. Gen. Virol., 86 (Pt 10), 2823-30.
Park et al. 2005. "Inhibition of simian immunodeficiency virus by foamy virus vectors expressing siRNAs," Virology, 343(2), 275-82.
Parren et al. 2002. "Pre- and postexposure prophylaxis of Ebola virus infection in an animal model by passive transfer of a neutralizing human antibody," J. Virol. 76:6408-12.
Pastan et al. 1988. "A retrovirus carrying an MDR1 cDNA confers multidrug resistance and polarized expression of P-glycoprotein in MDCK cells," Proc. Natl. Acad Sci. U.S.A. 85:4486.
Payungporn, S., et al. 2005. "Single step multiplex real-time RT-PCR for H5N1 influenza A virus detection," J. Virol. Methods, 131(2), 143-7.
Pichler et al. 2005. "In vivo RNA interference-mediated ablation of MDR 1 P-glycoprotein," Clin Cancer Res, 11(12), 4487-94.
Pincus, S.H., et al. 2003. "A modified SCID mouse model of HIV infection with utility for testing anti-HIV therapies," AIDS Res. Hum. Retroviruses 19, 901-8.
Presta. "Antibody engineering," Curr. Op. Struct. Biol., 2:593-596 (1992).
Remington's Pharmaceutical Sciences, by Martin, Mack Publishing Co., Easton, PA 15th Edition (1975).
Riechmann, L., et al. 1988. "Reshaping human antibodies for therapy," Nature, 332(6162), 323-327.
Riley, M., et al. 2006. "*Escherichia coli* K-12: a cooperatively developed annotation snapshot—2005," Nucleic Acids Res, 34(1), 1-9.
Sambrook et al. (2001) Molecular Cloning—A Laboratory Manual (3rd ed.) vol. 1-3, Cold Spring Harbor Laboratory, Cold Spring Harbor Press, NY, (Sambrook).
Sambrook et al. 1989. Molecular Cloning. 2nd edition, Cold Spring harbor Laboratory, Plainview, NY (chapters 9 and 11).
Sarver, N., et al. 1990. "Ribozymes as potential anti-HIV-1 therapeutic agents," Science 247(4947), 1222-5.
Schwartzenberger et al. 1996. "Targeted gene transfer to human hematopoietic progenitor cell lines through the c-kit receptor," Blood 87:472-478.
Singh et al. 2006. "An eIF5/eIF2 complex antagonizes guanine nucleotide exchange by eIF2B during translation initiation," The EMBO Journal, 25:4537-46.
Smee, D.F., et al. 2004. "Anti-cowpox virus activities of certain adenosine analogs, arabinofuranosyl nucleosides, and 2'fluro-arabinofuranosyl nucleosides," Nucleosides Nucleotides Nucleic Acids 23 (1-2), 375-83.
Smith, M. 1985. "In virtro mutagenesis," Ann. Rev. Gen., 19, 423-462.
Songyang, Z., et al. 1993. "SH2 domains recognize specific phosphopeptide sequences," Cell, 72:767-78.
Sutton, R.E.,et al. 2003. "Development of a mouse model for HIV/AIDS," Res. Initiat. Treat. Action, 8, 22-4.
Verhoeyen, M., et al. 1988. "Reshaping human antibodies: grafting an antilysozyme activity," Science, 239(4847), 1534-1536.

(56) References Cited

OTHER PUBLICATIONS

Wu et al. 1987. "Receptor-mediated in vitro gene transformation by a soluble DNA carrier system," J. Biol. Chem, 262:4429-32.

Wu et al. 2009. "Durable protection from Herpes Simplex Virus-2 transmission following intravaginal application of siRNAs targeting both a viral and host gene," Cell Host Microbe 22:5(1), 84-94.

Xu, L., et al. 1998. "Immunization for Ebola virus infection," Nat. Med. 4(1), 37-42.

Zoller, M.J. 1991. "New molecular biology methods for protein engineering," Curr. Opin. Struct. Biol. 1:605-610.

Zon, G. 1988. "Oligonucleotide analogues as potential chemotherapeutic agnets," Pharm. Res. 5:539-49.

Written Opinion and International Search Report dated Jun. 20, 2012 for international application PCT/US2011/064297, which was filed on Dec. 11, 201 and published as WO2012/102793 on Aug. 2, 2012. (Inventor—Donald Rubin; Applicant—Vanderbilt University) (pp. 1-3).

International Preliminary Report on Patebtability dated Jun. 12, 2013 for international application PCT/US2011/064297, which was filed on Dec. 11, 201 and published as WO2012/102793 on Aug. 2, 2012. (Inventor—Donald Rubin; Applicant—Vanderbilt University) (pp. 1-4).

\* cited by examiner

MAMMALIAN GENES INVOLVED IN TOXICITY AND INFECTION

CROSS REFERENCE TO RELATED APPLICATIONS

This application claims priority to U.S. Provisional Application 61/421,750, filed Dec. 10, 2010, and to U.S. Application 61/495,193, filed Jun. 9, 2011, both of which are hereby incorporated by reference in their entirety.

REFERENCE TO SEQUENCE LISTING

The Sequence Listing submitted Aug. 23, 2018 as a text file named "22000_0256U1_Updated_Sequence_Listing.txt," created on Aug. 14, 2018, and having a size of 108,361 bytes is hereby incorporated by reference pursuant to 37 C.F.R. § 1.52(e)(5).

FIELD OF THE INVENTION

The present invention relates to nucleic acid sequences and cellular proteins encoded by these sequences that are involved in the toxicity of a toxin and that are also involved in infection or are otherwise associated with the life cycle of one or more pathogens, such as a virus, bacteria, a fungus or a parasite. The invention also relates to modulators of nucleic acid sequences and cellular proteins encoded by these sequences that are involved in the toxicity of a toxin and that are also involved in infection or are otherwise associated with the life cycle of a pathogen.

BACKGROUND

Toxins, chemical compounds produced by living organisms, negatively affect the health of people and animals throughout the world, with the results ranging from mildly disabling disease to immediate death. In fact, one of the most deadly compounds currently known to man is the botulinum toxin; a bacterial toxin produced by the organism *Clostridium botulinum*. The targets and affects of toxins vary widely and include hemotoxins, which target and destroy red blood cells, necrotoxins, which indiscriminately cause cell death and destruction of all tissue types, and neurotoxins, which target and affect the nervous system. Furthermore, toxin weapons utilized in a terrorist attack could potentially cause mass casualties if properly deployed. Currently, the most effective treatment for toxicity resulting from toxin exposure is the administration of an antitoxin. However, the development of antitoxins can be a time consuming process, and during an attack with a toxin weapon antitoxin stockpiles could become rapidly depleted, thereby leaving effective treatment in short supply. Thus, there exists an immediate need for a treatment that can reduce the toxicity of a toxin, and for methods of identifying new compounds that can combat the threat of an attack with a toxin weapon.

Infectious diseases also affect the health of people and animals around the world, causing serious illness and death. Black Plague devastated the human population in Europe during the middle ages. Pandemic flu killed millions of people in the 20th century and is a threat to reemerge.

Addition of ε-toxin to MDCK cells leads to the formation of detergent-resistant toxin oligomers (Miyata et al., Nagahama et al. (1998), Petit et al.) Formation of the oligomeric complexes is detectable as early as 15 minutes after toxin addition to MDCK cells, at which time 10 to 20% of the monolayer has been killed (Petit et al.) Formation of these oligomeric complexes is observed when ε-toxin is added to sensitive, but not resistant cell lines (Nagahama et al. (1998)). In addition, the active form of ε-toxin, but not the inactive prototoxin, is able to form the detergent-resistant complexes (Nagahama et al. (1998)). Specifically, removal of a carboxyterminal peptide from the ε-prototoxin upon activation is required for both the increased cytotoxicity and the ability to form oligomeric complexes (Miyata et al.) Treating MDCK cells with ε-toxin is rapidly followed by efflux of intracellular $K^+$ and increases in intracellular $Cl^-$ and $Na^+$ (Petit et al.) There is no evidence that the ε-toxin enters cells (Nagahama et al. (1998), Petit et al.). Thus, in one pathway, the lethal activity of the toxin can be a direct effect of the toxin forming oligomeric pores in the plasma membrane of target cells, leading to depolarization of the cell's electrochemical gradient, disruption of ion homeostasis, and cell death. However, an alternate pathway leading to cell death also can be involved. Addition of ε-toxin to a murine renal cortical collecting duct cell line leads to a rapid depletion of cellular ATP levels, stimulates AMP-activated protein kinase, and induces nuclear translocation of apoptosis-inducing factor, a potent caspase-independent cell death effector (Chasin et al.) In this study, the ATP-depletion and cell death appeared to be independent of toxin oligomerization and the formation of pores (Chasin et al.) Thus host factors, in addition to the cell-surface receptor, can contribute to ε-toxin-mediated cytotoxicity.

A variety of studies exploring the cytotoxic activities of other pore-forming toxins has suggested that host factors (beyond cell-surface receptors) also contribute to toxin-induced cytotoxicity (Gonzalez et al. Bischof et al., Gurcel et al., Huffman et al., Bellier et al., Zhang et al., Skals et al., Soletti et al.) For example, the mammalian protein kinase A pathway has been shown to be required for Cry 1 Ab-induced cell death (Zhang et al.) Additionally, *E. coli* α-hemolysin has been shown to lead to leakage of ATP from cells; the extracellular ATP then activates P2X pores that potentiate cell lysis (Skals et al.) Finally, pre-treatment of glioma cells with inhibitors of mitogen-activated/extracellular regulated kinase 1, protein kinase C, or $Ca^{2+}$/calmodulin-dependent kinase 11 protects cells from Bc2 and equinatoxin-11 (Soletli et al.)

*Clostridium difficile* infection (CDI), commonly referred to as "*C. difficile*" or "c-diff", has become a significant medical problem in hospitals, long-term care facilities, and in the community and is estimated to afflict more than 450,000 people each year in the U.S. Patients typically develop CDI from the use of broad-spectrum antibiotics that disrupt normal gastrointestinal (gut) flora, thus allowing *C. difficile* bacteria to flourish and produce toxins.

*Clostridium difficile* is a member of a family of bacteria that are capable of producing toxins in response to environmental stress and can become spores impervious to most means of simple eradication. The toxins produced by these bacteria are the major reason for these organisms being highly pathogenic. At present, between 1.1 and 3 billion dollars are spent in the USA market due to antibiotic induced expression of the C-diff toxins, with direct treatment accounting for at least 10% of the total expenditures.

C-diff produces two toxins of note, TcdA and TcdB (the A and B toxins, respectively). A new strain of c-diff produces 16 to 30 times the amount of toxin A and B as the previously common c-diff isolates, and this new strain accounts for non-hospital based severe infection.

Traditional treatments for toxicity include pharmaceuticals. However, the vast majority of toxins lack an effective drug. Those drugs that exist have several limitations and drawbacks that including limited effectiveness and toxicity. Thus, an urgent need exists for alternative treatments for toxins and infectious diseases, and methods of identifying new drugs to combat these threats.

SUMMARY OF THE INVENTION

The present invention provides genes and gene products set forth in Table 1 that are involved in the toxicity of a toxin such as a bacterial toxin or a plant toxin. Also provided are methods of decreasing the toxicity of a toxin, such as a bacterial toxin or a plant toxin, comprising decreasing expression or activity of one or more of these genes or gene products set forth in Table 1. Also provided are methods of decreasing the toxicity of a toxin, such as a bacterial toxin or a plant toxin, in a subject by administering an agent that decreases the expression and/or activity of the genes or gene products set forth in Table 1. Further provided are methods of identifying an agent that decreases the toxicity of a toxin such as a bacterial toxin or a plant toxin.

The present invention further provides genes and gene products set forth in Table 1 that are involved in infection by one or more pathogens such as a virus, a parasite, a bacteria or a fungus, or are otherwise associated with the life cycle of a pathogen. Also provided are methods of decreasing infection in a cell by a pathogen comprising decreasing expression or activity of one or more of these genes or gene products set forth in Table 1. Also provided are methods of decreasing infection by a pathogen in a subject by administering an agent that decreases the expression and/or activity of the genes or gene products set forth in Table 1. Further provided are methods of identifying an agent that decreases infection by a pathogen.

DETAILED DESCRIPTION OF THE INVENTION

The present invention may be understood more readily by reference to the following detailed description of preferred embodiments of the invention and the Examples included therein.

Before the present compounds, compositions and/or methods are disclosed and described, it is to be understood that this invention is not limited to specific nucleic acids, specific polypeptides, or to particular methods, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally obtained prior to treatment" means obtained before treatment, after treatment, or not at all.

As used throughout, by "subject" is meant an individual. Preferably, the subject is a mammal such as a primate, and, more preferably, a human. Non-human primates include marmosets, monkeys, chimpanzees, gorillas, orangutans, and gibbons, to name a few. The term "subject" includes domesticated animals, such as cats, dogs, etc., livestock (for example, cattle, horses, pigs, sheep, goats, etc.), laboratory animals (for example, ferret, chinchilla, mouse, rabbit, rat, gerbil, guinea pig, etc.) and avian species (for example, chickens, turkeys, ducks, pheasants, pigeons, doves, parrots, cockatoos, geese, etc.). The subjects of the present invention can also include, but are not limited to fish (for example, zebrafish, goldfish, tilapia, salmon and trout), amphibians and reptiles.

In the present application, the genes listed in Table 1 are host genes involved in toxicity and viral infection. All of the host genes involved in toxicity and viral infection, set forth in Table 1, were identified using gene trap methods that were designed to identify host genes that are necessary for toxicity or viral infection or growth, but nonessential for cellular survival. These gene trap methods are set forth in the Examples as well as in U.S. Pat. No. 6,448,000 and U.S. Pat. No. 6,777,177, U.S. Pat. Nos. 6,448,000 and 6,777,177 and are both incorporated herein in their entireties by this reference.

As used herein, a gene "nonessential for cellular survival" means a gene for which disruption of one or both alleles results in a cell viable for at least a period of time which allows the toxicity of a toxin or viral replication to be decreased or inhibited in a cell. Such a decrease can be utilized for preventative or therapeutic uses or used in research. A gene necessary for toxicity or pathogenic infection or growth means the gene product of this gene, either protein or RNA, secreted or not, is necessary, either directly or indirectly in some way for the pathogen to grow. As utilized throughout, "gene product" is the RNA or protein resulting from the expression of a gene listed in Table 1.

The nucleic acids of these genes and their encoded proteins can be involved in all phases of the toxicity of a toxin and the viral life cycle including, but not limited to, toxin related cell membrane degradation, toxin related cell pore formation, toxin attachment to cellular receptors, toxin internalization, viral attachment to cellular receptors, viral infection, viral entry, internalization, disassembly of the virus, viral replication, genomic integration of viral sequences, transcription of viral RNA, translation of viral mRNA, transcription of cellular proteins, translation of cellular proteins, trafficking, proteolytic cleavage of viral proteins or cellular proteins, assembly of viral particles, budding, cell lysis and egress of virus from the cells.

Although the genes set forth herein were identified as cellular genes involved in toxicity of a toxin and viral infection, as discussed throughout, the present invention is not limited to toxicity of a toxin and viral infection. Therefore, any of these nucleic acid sequences and the proteins encoded by these sequences can be involved in toxicity and infection by any infectious pathogen such as a bacteria, a fungus or a parasite which includes involvement in any phase of the infectious pathogen's life cycle.

As utilized herein, when referring to any one of the genes in Table 1, what is meant is any gene, any gene product, or any nucleic acid (DNA or RNA) associated with that gene name or a pseudonym thereof, as well as any protein, or any protein from any organism that retains at least one activity of the protein associated with the gene name or any pseudonym thereof which can function as a nucleic acid or protein utilized by a pathogen. The nucleic acid or protein sequence can be from or in a cell in a human, a non-human primate, a mouse, a rat, a cat, a dog, a chimpanzee, a horse, a cow, a pig, a sheep, a guinea pig, a rabbit, a zebrafish, a chicken, to name a few.

By way of example, Table 1 refers to AP2S1. Therefore, this is intended to include, but not be limited to, any AP2S1 gene, AP2S1 gene product, for example, an AP2S1 nucleic acid (DNA or RNA) or AP2S1 protein, from any organism that retains at least one activity of AP2S1 and can function as a AP2S1 nucleic acid or protein utilized by a pathogen. For example, the nucleic acid or protein sequence can be from or in a cell in a human, a non-human primate, a mouse, a rat, a cat, a dog, a chimpanzee, a horse, a cow, a pig, a sheep, a guinea pig, a rabbit, a zebrafish, a chicken, to name a few.

As used herein, a gene is a nucleic acid sequence that encodes a polypeptide under the control of a regulatory sequence, such as a promoter or operator. The coding sequence of the gene is the portion transcribed and translated into a polypeptide (in vivo, in vitro or in situ) when placed under the control of an appropriate regulatory sequence. The boundaries of the coding sequence can be determined by a start codon at the 5' (amino) terminus and a stop codon at the 3' (carboxyl) terminus. If the coding sequence is intended to be expressed in a eukaryotic cell, a polyadenylation signal and transcription termination sequence can be included 3' to the coding sequence.

Transcriptional and translational control sequences include, but are not limited to, DNA regulatory sequences such as promoters, enhancers, and terminators that provide for the expression of the coding sequence, such as expression in a host cell. A polyadenylation signal is an exemplary eukaryotic control sequence. A promoter is a regulatory region capable of binding RNA polymerase and initiating transcription of a downstream (3' direction) coding sequence. Additionally, a gene can include a signal sequence at the beginning of the coding sequence of a protein to be secreted or expressed on the surface of a cell. This sequence can encode a signal peptide, N-terminal to the mature polypeptide, which directs the host cell to translocate the polypeptide.

Table 1 provides the Entrez Gene numbers for the human genes set forth herein. The information provided under the Entrez Gene numbers listed in Table 1 is hereby incorporated entirely by this reference. One of skill in the art can readily obtain this information from the National Center for Biotechnology Information at the National Library of Medicine (http://www.ncbi.nlm.nih.gov/entrez/query.fcgi?db=gene). By accessing Entrez Gene, one of skill in the art can readily obtain information about every gene listed in Table 1, such as the genomic location of the gene, a summary of the properties of the protein encoded by the gene, expression patterns, function, information on homologs of the gene as well as numerous reference sequences, such as the genomic, mRNA and protein sequences for each gene. Therefore, one of skill in the art can readily obtain sequences, such as genomic, mRNA and protein sequences by accessing information available under the Entrez Gene number provided for each gene. Thus, all of the information readily obtained from the Entrez Gene Nos. set forth herein is also hereby incorporated by reference in its entirety.

Also provided in Table 1 are the GenBank Accession Nos. for at least one example of for at least one example of the mRNA sequence and the GenBank Accession Nos. for the human protein sequence if available. It is noted that there may be multiple isoforms or variants of a gene or protein, and these are also contemplated herein by reference to the gene, even when the specific Accession Number for that isoform or variant is not given. For certain non-protein coding genes, a non-coding RNA is provided, for example, for SNORA and SNORD molecules. The nucleic acid sequences and protein sequences provided under the GenBank Accession Nos. mentioned herein are hereby incorporated in their entireties by this reference. One of skill in the art would know that the nucleotide sequences provided under the GenBank Accession Nos. set forth herein can be readily obtained from the National Center for Biotechnology Information at the National Library of Medicine (http://www.ncbi.nlm.nih.gov/entrez/query.fcgi?db=nucleotide). Similarly, the protein sequences set forth herein can be readily obtained from the National Center for Biotechnology Information at the National Library of Medicine (http://www.ncbi.nlm.nih.gov/entrez/query.fcgi?db=protein). The nucleic acid sequences and protein sequences provided under the GenBank Accession Nos. mentioned herein are hereby incorporated in their entireties by this reference.

These examples are not meant to be limiting as one of skill in the art would know how to obtain additional sequences for the genes and gene products listed in Table 1 from other species by accessing GenBank or other sequence databases. One of skill in the art would also know how to align the sequences disclosed herein with sequences from other species in order to determine similarities and differences between the sequences set forth in Table 1 and related sequences, for example, by utilizing BLAST. As set forth herein, a nucleic acid sequence for any of the genes set forth in Table 1 can be a full-length wild-type (or native) sequence, a genomic sequence, a variant (for example, an allelic variant or a splice variant), a nucleic acid fragment, a homolog or a fusion sequence that retains the activity of the gene utilized by the pathogen or its encoded gene product.

TABLE 1

| HUGO Gene Name | Entrez Gene Number | Human Genbank RNA accession number | Human Genbank protein accession number | Aliases | Trap toxin |
|---|---|---|---|---|---|
| AP2S1 | 1175 | NM_004069.3 | NP_004060.2 | AP17; CLAPS2; AP17-DELTA | C. difficile toxin |

TABLE 1-continued

TABLE 1

| HUGO Gene Name | Entrez Gene Number | Human Genbank RNA accession number | Human Genbank protein accession number | Aliases | Trap toxin |
|---|---|---|---|---|---|
| AREG | 374 | NM_001657.2 | NP_001648.1 | AR; SDGF; AREGB; CRDGF; MGC13647 | C. difficile toxin |
| ARL61P1 | 23204 | NM_015161.1 (SEQ ID NO: 371) | NP_055976.1 | AIP1; ARMER; ARL61P; KIAA0069 | C. difficile toxin |
| ATAD4 | 79170 | NM_024320.2 | NP_077296.1 | MGC11242; PRR15L | C. difficile toxin |
| BRP44 | 25874 | NM_001143674.1 | NP_001137146.1 | MGC125752; MGC125753; DKFZp564B167 | C. difficile toxin |
| C200RF72 | 92667 | NM_052865.2 | NP_443097.1 | FLJ14597; bA504H3.4 | C. difficile toxin |
| CCNGI | 900 | NM_004060.3 | NP_004051.1 | CCNG | C. difficile toxin |
| CDH17 | 1015 | NM_001144663.1 | NP_001138135.1 | HPT1; CDH16; HPT-1; FLJ26931; MGC138218; MGC142024 | C. difficile toxin |
| CPEB4 | 80315 | NM_030627.2 | NP_085130.2 | KIAA1673 | C. difficile toxin |
| DCAF6 | 55827 | NM_018442.2 | NP_060912.2 | NRIP; ARCAP; IQWD1; PC326; MSTP'055; RP4-745114.1; 1200006M05Rik | C. difficile toxin |
| DRG1 | 4733 | NM_004147.3 | NP_004138.1 | NEDD3; DKFZp434NI827 | C. difficile toxin |
| EHD1 | 10938 | NM_006795.2 | NP_006786.2 | PAST; PAST1; H-PAST; HPAST1; FLJ42622; FLJ44618 | C. difficile toxin |
| EIF3B | 8662 | NM_001037283.1 | NP_001032360.1 | PRT1; EIF3S9; E13-ETA; E1F3-P110; EIF3-P116; MGC104664; MGC131875 | C. difficile toxin |
| FGL1 | 2267 | NM_004467.3 | NP_004458.3 | HFREP1; HP-041; LFIRE1; MGC12455 | C. difficile toxin |
| FNDC1 | 84624 | NM_032532.2 (SEQ ID NO: 374) | NP_115921.2 | AGS8; FNDC2; MEL4B3; KIAA1866; bA243O10.1; dJ322A24.1; RP11-243O10.2 | C. difficile toxin |
| HIST1H2B1 | 8346 | NM_003525.2 | NP_003516.1 | H2B/a; H2B/g; H2B/h; H2B/k; H2B/l; H2BFK; HIST1H2BC; HIST1H2BE; HISTIH2BF; HISTIH2BG | C. difficile toxin |
| hmm1252364 | | | | | C. difficile toxin |
| hmm1436894 | | | | | C. difficile toxin |
| hmm1438894 | | | | | C. difficile toxin |
| hmm2826564 | | | | | C. difficile toxin |
| hmm34086333 | | | | | C. difficile toxin |
| hmm697334 | | | | | C. difficile toxin |
| HNRNPH1 | 3187 | NM_005520.2 | NP_005511.1 | HNRPH; HNRPH1; hnRNPH; DKFZp686A15170 | C. difficile toxin |

TABLE 1-continued

| HUGO Gene Name | Entrez Gene Number | Human Genbank RNA accession number | Human Genbank protein accession number | Aliases | Trap toxin |
|---|---|---|---|---|---|
| LGALS3 | 3958 | NM_002306.3 | NP_002297.2 | L31; GAL3; MAC2; CBP35; GALBP; GALIG; LGALS2 | C. difficile toxin |
| LGALS3BP | 3959 | NM_005567.3 | NP_005558.1 | 90K; BTBD17B; MAC-2-BP' | C. difficile toxin |
| LOC645960 | 645960 | XM_002342818.1 | XP_002342859.1 | | C. difficile toxin |
| MIR1304 | 100302240 | NR_031639.1 | | MIRN1304; hsa-mir-1304 | C. difficile toxin |
| MIR192 | 406967 | NR_029578.1 | | MIRN192; miR-192; miRNA192 | C. difficile toxin |
| MIR194-2 | 406970 | NR_029829.1 | | MIRN194-2 | C. difficile toxin |
| N4BP2L2 | 10443 | NM_014887.2 (SEQ ID NO: 370) | NP_055702.1 | CG005; PFAAP5; 92M18.3; FLJ36195; FLJ41089; FLJ43077 | C. difficile toxin |
| PL1N2 | 123 | NM_001122.2 | NP_001113.2 | ADFP; ADRP; MGC10598 | C. difficile toxin |
| POU3F3 | 5455 | NM_006236.1 | NP_006227.1 | BRN1; OTF8 | C. difficile toxin |
| PRR15L | 79170 | NM_024320.2 | NP_077296.1 | ATAD4; MGC11242 | C. difficile toxin |
| PVRL3 | 25945 | NM_015480.1 | NP_056295.1 | PPR3; PRR3; CD113; PVRR3; CDw113; FLJ90624; nectin-3; DKFZp566B0846 | C. difficile toxin |
| RAB3B | 5865 | NM_002867.3 | NP_002858.2 | | C. difficile toxin |
| RPL6P23 | 100130524 | | | | C. difficile toxin |
| RPS15A | 6210 | NM_001019.4 | NP_001010.2 | S15a; FLJ27457; MGC111208 | C. difficile toxin |
| RPS6P1O | 100270865 | | | RPS6_4_967 | C. difficile toxin |
| RSPH3 | 83861 | NM_031924.4 | NP_114130.3 | RSP3; RSHL2; dJ111C20.1 | C. difficile toxin |
| SC5DL | 6309 | NM_001024956.2 (SEQ ID NO: 373) | NP_001020127.1 | ERG3; SC5D; S5DES | C. difficile toxin |
| SEC31A | 22872 | NM_001077207.2 (SEQ ID NO: 372) | NP_001070675.1 | ABP125; ABP130; HSPC275; HSPC334; SEC31L1; KIAA0905; MGC90305; DKFZp686N07171 | C. difficile toxin |
| SLCO2B1 | 11309 | NM_007256.3 | NP_009187.1 | OATPB; OATP-B; OATP2B1; SLC21A9; KIAA0880; DKFZp686E0517 | C. difficile toxin |
| SNORA25 | 684959 | NR_003028.1 | | ACA25 | C. difficile toxin |
| SNORD17 | 692086 | NR_003045.1 | | HB1-43 | C. difficile toxin |
| SNX5 | 27131 | NM_014426.2 | NP_055241.1 | FLJ10931 | C. difficile toxin |
| TM4SF1 | 4071 | NM_014220.2 (SEQ ID NO: 369) | NP_055035.1 | L6; H-L6; M3S1; TAAL6 | C. difficile toxin |
| TTR | 7276 | NM_000371.3 | NP_000362.1 | PALB; TBPA; HsT2651 | C. difficile toxin |

As used herein, the term "nucleic acid" refers to single or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the moieties discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides), a reduction in the AT content of AT rich regions, or replacement of non-preferred codon usage of the expression system to preferred codon usage of the expression system. The nucleic acid can be directly cloned into an appropriate vector, or if desired, can be modified to facilitate the subsequent cloning steps. Such modification steps are routine, an example of which is the addition of oligonucleotide linkers which contain restriction sites to the termini of the nucleic acid. General methods are set forth in in Sambrook et al. (2001) *Molecular Cloning—A Laboratory Manual* (3rd ed.) Vol. 1-3, Cold Spring Harbor Laboratory, Cold Spring Harbor Press, NY, (Sambrook).

Once the nucleic acid sequence is obtained, the sequence encoding the specific amino acids can be modified or changed at any particular amino acid position by techniques well known in the art. For example, PCR primers can be designed which span the amino acid position or positions and which can substitute any amino acid for another amino acid. Alternatively, one skilled in the art can introduce specific mutations at any point in a particular nucleic acid sequence through techniques for point mutagenesis. General methods are set forth in Smith, M. "In vitro mutagenesis" *Ann. Rev. Gen.*, 19:423-462 (1985) and Zoller, M. J. "New molecular biology methods for protein engineering" *Curr. Opin. Struct. Biol.*, 1:605-610 (1991), which are incorporated herein in their entirety for the methods. These techniques can be used to alter the coding sequence without altering the amino acid sequence that is encoded.

The sequences contemplated herein include full-length wild-type (or native) sequences, as well as allelic variants, variants, fragments, homo logs or fusion sequences that retain the ability to function as the cellular nucleic acid or protein involved in viral infection. In certain examples, a protein or nucleic acid sequence has at least 50% sequence identity, for example at least 50%, 55%, 60%, 65%, 70%, 75%, 80%, 85%, 90%, 95%, or 98% sequence identity to a native sequences of the genes set forth in Table 1. In other examples, a nucleic acid sequence involved in viral infection has a sequence that hybridizes to a sequence of a gene set forth in Table 1 and retains the activity of the sequence of the gene set forth in Table 1. For example, and not to be limiting, a nucleic acid that hybridizes to an AP2S1 nucleic acid sequence and encodes a protein that retains AP2S1 activity is contemplated by the present invention. Such sequences include the genomic sequence for the genes set forth in Table 1. The examples set forth above for AP2S1 are merely illustrative and should not be limited to AP2S1 as the analysis set forth in this example applies to every nucleic acid and protein for the genes listed in Table 1.

Unless otherwise specified, any reference to a nucleic acid molecule includes the reverse complement of the nucleic acid. Except where single-strandedness is required by the text herein (for example, a ssRNA molecule), any nucleic acid written to depict only a single strand encompasses both strands of a corresponding double-stranded nucleic acid. Fragments of the nucleic acids for the genes set forth in Table 1 and throughout the specification are also contemplated. These fragments can be utilized as primers and probes to amplify, inhibit or detect any of the nucleic acids or genes set forth in Table 1.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

| Very High Stringency (detects sequences that share 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |
| High Stringency (detects sequences that share 80% identity or greater) | |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |
| Low Stringency (detects sequences that share greater than 50% identity) | |
| Hybridization: | 6x SSC at RT to 55° C. for 16-20 hours |
| Wash at least twice: | 2x-3x SSC at RT to 55° C. for 20-30 minutes each. |

Also provided is a vector, comprising a nucleic acid set forth herein. The vector can direct the in vivo or in vitro synthesis of any of the proteins or polypeptides described herein. The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene (See generally, Sambrook et al.). The vector, for example, can be a plasmid. The vectors can contain genes conferring hygromycin resistance, ampicillin resistance, gentamicin resistance, neomycin resistance or other genes or phenotypes suitable for use as selectable markers, or methotrexate resistance for gene amplification.

There are numerous other *E. coli* (*Escherichia coli*) expression vectors, known to one of ordinary skill in the art, which are useful for the expression of the nucleic acid insert. Other microbial hosts suitable for use include bacilli, such as *Bacillus sublilis*, and other enterobacteriaceae, such as *Salmonella, Serratia*, and various *Pseudomonas* species. In these prokaryotic hosts one can also make expression vectors, which will typically contain expression control sequences compatible with the host cell (e.g. an origin of replication). In addition, any number of a variety of well-known promoters will be present, such as the lactose promoter system, a tryptophan (Trp) promoter system, a beta-lactamase promoter system, or a promoter system from phage lambda. Additionally, yeast expression can be used. The invention provides a nucleic acid encoding a polypeptide of the present invention, wherein the nucleic acid can be expressed by a yeast cell. More specifically, the nucleic acid can be expressed by *Pichia pastoris* or *S. cerevisiae*.

Mammalian cells also permit the expression of proteins in an environment that favors important post-translational modifications such as folding and cysteine pairing, addition of complex carbohydrate structures, and secretion of active protein. Vectors useful for the expression of active proteins are known in the art and can contain genes conferring hygromycin resistance, genticin or G418 resistance, or other genes or phenotypes suitable for use as selectable markers, or methotrexate resistance for gene amplification. A number of suitable host cell lines capable of secreting intact human proteins have been developed in the art, and include the CHO cell lines, HeLa cells, COS-7 cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc.

The expression vectors described herein can also include nucleic acids of the present invention under the control of an inducible promoter such as the tetracycline inducible promoter or a glucocorticoid inducible promoter. The nucleic acids of the present invention can also be under the control of a tissue-specific promoter to promote expression of the nucleic acid in specific cells, tissues or organs. Any regulatable promoter, such as a metallothionein promoter, a heat-shock promoter, and other regulatable promoters, of which many examples are well known in the art are also contemplated. Furthermore, a Cre-loxP inducible system can also be used, as well as a Flp recombinase inducible promoter system, both of which are known in the art.

Insect cells also permit the expression of mammalian proteins. Recombinant proteins produced in insect cells with baculovirus vectors undergo post-translational modifications similar to that of wild-type proteins. The invention also provides for the vectors containing the contemplated nucleic acids in a host suitable for expressing the nucleic acids. The host cell can be a prokaryotic cell, including, for example, a bacterial cell. More particularly, the bacterial cell can be an *E. coli* cell. Alternatively, the cell can be a eukaryotic cell, including, for example, a Chinese hamster ovary (CHO) cell, a COS-7 cell, a HELA cell, an avian cell, a myeloma cell, a *Pichia* cell, or an insect cell. A number of other suitable host cell lines have been developed and include myeloma cell lines, fibroblast cell lines, a cell line suitable for infection by a pathogen, and a variety of tumor cell lines such as melanoma cell lines. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, Lipofectamine, or lipofectin mediated transfection, electroporation or any method now known or identified in the future can be used for other eukaryotic cellular hosts.

The mammalian genome contains over 25,000 genes that are differentially expressed in various tissues. A host may vary in the level of expression or in the function of a particular gene (through single nucleotide polymorphisms) which confers a phenotype, such as susceptibility to an infectious disease. Some of these disease states can be mirrored in tissue culture cells, or may be evident through epidemiology/genomic study of susceptible individuals. In order to more quickly discover genes that play a role in particular cells or hosts, the differential expression of genes can be analyzed. The use of gene-trap data may allow for a limited gene set to be queried, thereby saving resources and helping to select most likely candidate genes for a particular phenotype. Targeted gene expression as directed by gene-trap selected genes may thus yield a validation set more quickly.

Also disclosed herein is PheDA (Phenotype Directed Array). Gene-trap selection finds candidate genes that confer a phenotype of resistance to intoxication (toxin) or resistance to infection (virus, bacteria, parasite). To further define which genes may provide tissue specific traits, or confer disease producing properties, it's proposed a gene-trap selection can be linked with resistance/susceptibility patterns in tissue culture cells (differential display) and mammalian hosts (GWA/differential display).

Polypeptides

The present invention provides isolated polypeptides comprising the polypeptide or protein sequences for the genes set forth in Table 1. The present invention also provides fragments of these polypeptides. These fragments can be of sufficient length to serve as antigenic peptides for the generation of antibodies. The present invention also contemplates functional fragments that possess at least one activity of a gene or gene product listed in Table 1, for example, involved in viral infection.

By "isolated polypeptide" or "purified polypeptide" is meant a polypeptide that is substantially free from the materials with which the polypeptide is normally associated in nature or in culture. The polypeptides of the invention can be obtained, for example, by extraction from a natural source if available (for example, a mammalian cell), by expression of a recombinant nucleic acid encoding the polypeptide (for example, in a cell or in a cell-free translation system), or by chemically synthesizing the polypeptide. In addition, a polypeptide can be obtained by cleaving full length polypeptides. When the polypeptide is a fragment of a larger naturally occurring polypeptide, the isolated polypeptide is shorter than and excludes the full-length, naturally occurring polypeptide of which it is a fragment.

Also provided by the present invention is a polypeptide comprising an amino acid sequence at least about 50%, 55%; 60%, 65%, 70%, 75%, 80%, 85%, 90%, 95%, 96%, 97%, 98% or 99% identical to the native polypeptide sequence for any gene set forth in Table 1. It is understood that as discussed herein the use of the terms "homology" and "identity" mean the same thing as similarity. Thus, for example, if the use of the word homology is used to refer to two non-natural sequences, it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related.

In general, it is understood that one way to define any known variants and derivatives or those that might arise, of the disclosed nucleic acids and polypeptides herein, is through defining the variants and derivatives in terms of homology to specific known sequences. In general, variants of nucleic acids and polypeptides herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two polypeptides or nucleic acids.

Methods of Decreasing Toxicity

The present invention provides a method of decreasing the toxicity of a toxin in a cell comprising decreasing expression or activity of a gene or gene product set forth in Table 1. The cell can be in vitro, ex vivo or in vivo. The toxin can be an exotoxin or an endotoxin. More specifically, the toxin can be a type I exotoxin, for example a superantigen, a type II exotoxin, for example a pore forming toxin, a type III exotoxin, for example an AB toxin, or a lipopolysaccharide. Toxins can include, but are not limited to, a bacterial toxin, neurotoxins, such as botulinum neurotoxins, ricin, *Clostridium perfringens* toxins, *Clostridium difficile* toxins, *Clostridium tetani* toxins, saxitoxins, tetrodotoxins, abrin, conotoxins, Staphlococcal toxins, *E. coli* toxins, streptococcal toxins, diphtheria toxin, cholera toxin, pertussis toxin, *pseudomonas* toxin, *bacillus* toxin, shigatoxins, T-2 toxins, anthrax toxins, chimeric forms of the toxins listed herein, and the like. Toxins can further include, but are not limited to cyanotoxins, hemotoxins, necrotoxins, and mycotoxins, such as aflatoxin, amatoxin, citrinin, cytohalasin, ergotamine, fumonisin, gliotoxin, ibotenic acid, muscimol, ochratoxin, patulin, sterigmatocystin, trichothecene, vomitoxin, zeranol, and zearalenone. The decrease in toxicity can be at least about 10%, 20%, 30%, 40%, 50%, 60, 70%, 80%, 90%, 95%, 100% or any other percentage decrease in between these percentages as compared to the level of toxicity in a cell wherein expression or activity of a gene or gene product set forth in Table 1 has not been decreased.

Toxicity can be measured, for example, via a cell viability, apoptosis assay, LDH release assay or cytotoxicity assay (See, for example, Kehl-Fie and St. Geme "Identification and characterization of an RTX toxin in the emerging pathogen *Kingella kingae*," *J. Bacteriol.* 189(2):430-6 (2006) and Kirby "Anthrax Lethal Toxin Induces Human Endothelial cell Apoptosis," *Infection and Immunity* 72: 430-439 (2004), both of which are incorporated herein in their entireties by this reference.)

In the methods set forth herein, expression can be inhibited, for example, by inhibiting transcription of the gene, or inhibiting translation of its gene product. Similarly, the activity of a gene product (for example, an mRNA, a polypeptide or a protein) can be inhibited, either directly or indirectly. Inhibition or a decrease in expression does not have to be complete as this can range from a slight decrease in expression to complete ablation of expression. For example, expression can be inhibited by about 10%, 20%, 30%, 40%, 50%, 60%, 70%, 80%, 90%, 95%, 99%, 100% or any percentage in between as compared to a control cell wherein the expression of a gene or gene product set forth in Table 1 has not been decreased or inhibited. Similarly, inhibition or decrease in the activity of a gene product does not have to be complete as this can range from a slight decrease to complete ablation of the activity of the gene product. For example, the activity of a gene product can be inhibited by about 10%, 20%, 30%, 40%, 50%, 60%, 70%, 80%, 90%, 95%, 99%, 100% or any percentage in between as compared to a control cell wherein activity of a gene or gene product set forth in Table 1 has not been decreased or inhibited. As utilized herein, "activity of a gene product" can be an activity that is involved in the toxicity of a toxin, for example, interacting directly or indirectly, with a toxin, or an activity that the gene product performs in a normal cell, i.e. in a non-intoxicated cell. Depending on the gene product, one of skill in the art would know how to assay for an activity that is involved in toxicity, an activity that is involved in normal cellular function, or both. As set forth above, an activity of the proteins and nucleic acids listed herein can be the ability to bind or interact with other proteins. Therefore, the present invention also provides a method of decreasing the toxicity of a toxin by inhibiting or decreasing the interaction between any of the proteins of the present invention and other cellular proteins, such as, for example, receptors, enzymes, nucleic acids and hormones, provided that such inhibition correlates with decreasing the toxicity of a toxin. Also provided is a method of decreasing the toxicity of a toxin by inhibiting or decreasing the interaction between any of the proteins of the present invention and a viral, bacterial, parasitic or fungal protein (i.e. a non-host protein).

The cells of the present invention can be prokaryotic or eukaryotic, such as a cell from an insect, fish, crustacean, mammal, bird, reptile, yeast or a bacterium, such as *E. coli*. The cell can be part of an organism, or part of a cell culture, such as a culture of mammalian cells or a bacterial culture. Therefore, the cell can also be part of a population of cells. The cell(s) can also be in a subject.

Further provided by the present invention is a method of inhibiting the toxicity of a toxin in a cell comprising decreasing expression or activity of a gene or gene product set forth in Table 1, wherein the toxin is a *Clostridium difficile* toxin. More specifically, and not to be limiting the *Clostridium* toxin can be a *Clostridium perfringens* alpha toxin, *Clostridium perfringens* beta toxin, *Clostridium perfringens* epsilon toxin, *Clostridium perfringens* delta toxin, *Clostridium perfringens* theta toxin, *Clostridium perfringens* kappa toxin, *Clostridium perfringens* lambda toxin, *Clostridium perfringens* mu toxin, *Clostridium perfringens* toxin, *Clostridium perfringens* gamma toxin, *Clostridium perfringens* eta toxin, *Clostridium difficile* toxin A, *Clostridium difficile* toxin B, *Clostridium botulinum* A toxin, *Clostridium botulinum* B toxin, *Clostridium botulinum* C toxin, *Clostridium botulinum* D toxin, *Clostridium botulinum* E toxin, *Clostridium botulinum* F toxin or *Clostridium botulinum* G toxin.

The present invention also provides a method of inhibiting toxicity of a toxin in a cell comprising decreasing expression or activity of a gene or gene product set forth in Table 1, wherein the toxin is a ricin toxin, saxitoxin, tetrodotoxin, abrin, conotoxin, *E. coli* toxin, streptococcal toxins, diphtheria toxin, cholera toxin, pertussis toxin, *pseudomonas* toxin, *bacillus* toxin, shigatoxin, T-2 toxin, anthrax toxin, cyanotoxin, hemotoxin, necrotoxin, or a mycotoxin, such as aflatoxin, amatoxin, citrinin, cytohalasin, ergotamine, fumonisin, gliotoxin, ibotenic acid, muscimol, ochratoxin, patulin, sterigmatocystin, trichothecene, vomitoxin, zeranol, and zearalenone.

The present invention also provides a method of inhibiting the toxicity of two or more toxins in a cell comprising decreasing the expression or activity of a gene or a gene product set forth in Table 1, wherein the two or more toxins are selected from the groups consisting of *Clostridium perfringens* toxins, *Clostridium difficile* toxins, *Clostridium botulinum* toxins, *Clostridium tetani* toxins, saxitoxins, tetrodotoxins, abrin, conotoxins, Staphlococcal toxins, *E. coli* toxins, streptococcal toxins, diphtheria toxin, cholera toxin, pertussis toxin, *pseudomonas* toxin, *bacillus* toxin, shigatoxins, T-2 toxins, and anthrax toxins.

Specifically, any of the genes disclosed in Table 1 involved in the toxicity of a toxin can be involved in toxicity of both *Clostridium difficile* toxin A as well as *Clostridium difficile* toxin B. Other *Clostridium difficile* toxins, such as binary toxin, can also be inhibited utilizing the targets in Table 1. They can also inhibit the toxins individually. The toxicity of *Clostridium difficile* toxins, and in particular toxin A as well as *Clostridium difficile* toxin B, can be decreased by decreasing expression or activity of one or more of these genes or gene products, e.g. RNA or proteins, set forth in Table 1.

Methods of Decreasing Infection

The present invention also provides a method of inhibiting infection in a cell by a pathogen comprising decreasing expression or activity of a gene or gene product set forth in Table 1.

As stated above, an infection can be a viral infection, bacterial infection, fungal infection or a parasitic infection, to name a few. A decrease or inhibition of infection can occur in a cell, in vitro, ex vivo or in vivo. As utilized throughout, the term "infection" encompasses all phases of pathogenic life cycles including, but not limited to, attachment to cellular receptors, entry, internalization, disassembly, replication, genomic integration of pathogenic sequences, transcription of viral RNA, translation of viral RNA, transcription of host cell mRNA, translation of host cell mRNA, proteolytic cleavage of pathogenic proteins or cellular proteins, assembly of particles, endocytosis, cell lysis, budding, and egress of the pathogen from the cells. Therefore, a decrease in infection can be a decrease in attachment to cellular receptors, a decrease in entry, a decrease in internalization, a decrease in disassembly, a decrease in replication, a decrease in genomic integration of pathogenic sequences, a decrease in translation of mRNA, a decrease in proteolytic cleavage of pathogenic proteins or cellular proteins, a decrease in assembly of particles, a decrease in endocytosis, a decrease in cell lysis, a decrease in budding, or a decrease in egress of the pathogen from the cells. This decrease does not have to be complete as this can range from a slight decrease to complete ablation of the infection. A decrease in infection can be at least about 10%, 20%, 30%, 40%, 50%, 60, 70%, 80%, 90%, 95%, 100% or any other percentage decrease in between these percentages as compared to the level of infection in a cell wherein expression or activity of a gene or gene product set forth in Table 1 has not been decreased.

In the methods set forth herein, expression can be inhibited, for example, by inhibiting transcription of the gene, or inhibiting translation of its gene product. Similarly, the activity of a gene product (for example, an mRNA, a polypeptide or a protein) can be inhibited, either directly or indirectly. Inhibition or a decrease in expression does not have to be complete as this can range from a slight decrease in expression to complete ablation of expression. For example, expression can be inhibited by about 10%, 20%, 30%, 40%, 50%, 60%, 70%, 80%, 90%, 95%, 99%, 100% or any percentage in between as compared to a control cell wherein the expression of a gene or gene product set forth in Table 1 has not been decreased or inhibited. Similarly, inhibition or decrease in the activity of a gene product does not have to be complete as this can range from a slight decrease to complete ablation of the activity of the gene product. For example, the activity of a gene product can be inhibited by about 10%, 20%, 30%, 40%, 50%, 60%, 70%, 80%, 90%, 95%, 99%, 100% or any percentage in between as compared to a control cell wherein activity of a gene or gene product set forth in Table 1 has not been decreased or inhibited. As utilized herein, "activity of a gene product" can be an activity that is involved in pathogenicity, for example, interacting directly or indirectly, with pathogen, e.g. viral protein or viral nucleic acids, or an activity that the gene product performs in a normal cell, i.e. in a non-infected cell. Depending on the gene product, one of skill in the art would know how to assay for an activity that is involved in pathogenicity, an activity that is involved in normal cellular function, or both. As set forth above, an activity of the proteins and nucleic acids listed herein can be the ability to bind or interact with other proteins. Therefore, the present invention also provides a method of decreasing infection by inhibiting or decreasing the interaction between any of the proteins of the present invention and other cellular proteins, such as, for example, receptors, enzymes, nucleic acids and hormones, provided that such inhibition correlates with decreasing infection by the pathogen. Also provided is a method of decreasing infection by inhibiting or decreasing the interaction between any of the proteins of the present invention and a viral, bacterial, parasitic or fungal protein (i.e. a non-host protein).

The cells of the present invention can be prokaryotic or eukaryotic, such as a cell from an insect, fish, crustacean, mammal, bird, reptile, yeast or a bacterium, such as *E. coli*. The cell can be part of an organism, or part of a cell culture, such as a culture of mammalian cells or a bacterial culture. Therefore, the cell can also be part of a population of cells. The cell(s) can also be in a subject.

Examples of viral infections include but are not limited to, infections caused by RNA viruses (including negative stranded RNA viruses, positive stranded RNA viruses, double stranded RNA viruses and retroviruses), or DNA viruses. All strains, types, and subtypes of RNA viruses and DNA viruses are contemplated herein.

Examples of RNA viruses include, but are not limited to picornaviruses, which include aphthoviruses (for example, foot and mouth disease virus 0, A, C, Asia 1, SAT1, SAT2 and SAT3), cardioviruses (for example, encephalomycarditis virus and Theiller's murine encephalomyelitis virus), enteroviruses (for example polioviruses 1, 2 and 3, human enteroviruses A-D, bovine enteroviruses 1 and 2, human coxsackieviruses A1-A22 and A24, human coxsackieviruses B1-B5, human echoviruses 1-7, 9, 11-12, 24, 27, 29-33, human enteroviruses 68-71, porcine enteroviruses 8-10 and simian enteroviruses 1-18), erboviruses (for example, equine rhinitis virus), hepatovirus (for example human hepatitis A virus and simian hepatitis A virus), kobuviruses (for example, bovine kobuvirus and Aichi virus), parechoviruses (for example, human parechovirus I and human parechovirus 2), rhinovirus (for example, rhinovirus A, rhinovirus B, rhinovirus C, $HRV_{16}$, $HRV_{16}$ (VR-11757), $HRV_{14}$ (VR-284), or $HRV_{14}$ (VR-1559), human rhinovirus 1-100 and bovine rhinoviruses 1-3) and teschoviruses (for example, porcine teschovirus).

Additional examples of RNA viruses include caliciviruses, which include noroviruses (for example, Norwalk virus), sapoviruses (for example, Sapporo virus), lagoviruses (for example, rabbit hemorrhagic disease virus and European brown hare syndrome) and vesiviruses (for example vesicular exanthema of swine virus and feline calicivirus).

Other RNA viruses include astroviruses, which include mamastorviruses and avastroviruses. Togaviruses are also RNA viruses. Togaviruses include alphaviruses (for example, Chikungunya virus, Sindbis virus, Semliki Forest virus, Western equine encephalitis, Getah virus, Everglades virus, Venezuelan equine encephalitis virus and Aura virus) and rubella viruses. Additional examples of RNA viruses include the flaviviruses (for example, tick-borne encephalitis virus, Tyuleniy virus, Aroa virus, Dengue virus (types 1 to 4), Kedougou virus, Japanese encephalitis virus (JEV), West Nile virus (WNV), Kokobera virus, Ntaya virus, Spondweni virus, Yellow fever virus, Entebbe bat virus, Modoc virus, Rio Bravo virus, Cell fusing agent virus, pestivirus, GB virus A, GBV-A like viruses, GB virus C, Hepatitis G virus, hepacivirus (hepatitis C virus (HCV)) all six genotypes), bovine viral diarrhea virus (BVDV) types 1 and 2, and GB virus B).

Other examples of RNA viruses are the coronaviruses, which include, human respiratory coronaviruses such as SARS—CoV, HCoV-229E, HCoV-NL63 and HCoV-OC43. Coronaviruses also include bat SARS-like CoV, turkey coronavirus, chicken coronavirus, feline coronavirus and canine coronavirus. Additional RNA viruses include arteriviruses (for example, equine arterivirus, porcine reproductive and respiratory syndrome virus, lactate dehyrogenase elevating virus of mice and simian hemorraghic fever virus). Other RNA viruses include the rhabdoviruses, which include lyssaviruses (for example, rabies, Lagos bat virus, Mokola virus, Duvenhage virus and European bat lyssavirus), vesiculoviruses (for example, VSV-Indiana, VSV-New Jersey, VSV-Alagoas, Piry virus, Cocal virus, Maraba virus, Isfahan virus and Chandipura virus), and ephemeroviruses (for example, bovine ephemeral fever virus, Adelaide River virus and Berrimah virus). Additional examples of RNA viruses include the filoviruses. These include the Marburg and Ebola viruses (for example, EBOV-Z, EBOV-S, EBOV-IC and EBOV-R.

The paramyxoviruses are also RNA viruses. Examples of these viruses are the rubulaviruses (for example, mumps, parainfluenza virus 5, human parainfluenza virus type 2, Mapuera virus and porcine rubulavirus), avulaviruses (for example, Newcastle disease virus), respoviruses (for example, Sendai virus, human parainfluenza virus type 1 and type 3, bovine parainfluenza virus type 3), henipaviruses (for example, Hendra virus and Nipah virus), morbilliviruses (for example, measles, Cetacean morvilliirus, Canine distemper virus, Peste-des-petits-ruminants virus, Phocine distemper virus and Rinderpest virus), pneumoviruses (for example, human respiratory syncytial virus A2, B1 and S2, bovine respiratory syncytial virus and pneumonia virus of mice), metapneumoviruses (for example, human metapneumovirus and avian metapneumovirus). Additional paramyxoviruses include Fer-de-Lance virus, Tupaia paramyxovirus, Menangle virus, Tioman virus, Beilong virus, J virus, Mossman virus, Salem virus and Nariva virus.

Additional RNA viruses include the orthomyxoviruses. These viruses include influenza viruses and strains (e.g., influenza A, influenza A strain A/Victoria/3/75, influenza A strain A/Puerto Rico/8/34, influenza A HI NI (including but not limited to A/WS/33, A/NWS/33 and A/California/04/2009 strains), influenza B, influenza B strain Lee, and influenza C viruses) H2N2, H3N2, H5N1, H7N7, H1N2, H9N2, H7N2, H7N3 and H10N7), as well as avian influenza (for example, strains H5N1, H5N1 Duck/MN/1525/81, H5N2, H7N1, H7N7 and H9N2) thogotoviruses and isaviruses. Orthobunyaviruses (for example, Akabane virus, California encephalitis, Cache Valley virus, Snowshoe hare virus,) nairoviruses (for example, Nairobi sheep virus, Crimean-Congo hemorrhagic fever virus Group and Hughes virus), phleboviruses (for example, Candiru, Punta Toro, Rift Valley Fever, Sandfly Fever, Naples, Toscana, Sicilian and Chagres), and hantaviruses (for example, Hantaan, Dobrava, Seoul, Puumala, Sin Nombre, Bayou, Black Creek Canal, Andes and Thottapalayam) are also RNA viruses. Arenaviruses such as lymphocytic choriomeningitis virus, Lujo virus, Lassa fever virus, Argentine hemorrhagic fever virus, Bolivian hemorrhagic fever virus, Venezuelan hemorrhagic fever virus, SABV and WWAV are also RNA viruses. Borna disease virus is also an RNA virus. Hepatitis D (Delta) virus and hepatitis E are also RNA viruses.

Additional RNA viruses include reoviruses, rotaviruses, birnaviruses, chrysoviruses, cystoviruses, hypoviruses partitiviruses and totoviruses. Orbiviruses such as African horse sickness virus, Blue tongue virus, Changuinola virus, Chenuda virus, Chobar Gorge Corriparta virus, epizootic hemorraghic disease virus, equine encephalosis virus, Eubenangee virus, Ieri virus, Great Island virus, Lebombo virus, Orungo virus, Palyam virus, Peruvian Horse Sickness virus, St. Croix River virus, Umatilla virus, Wad Medani virus, Wallal virus, Warrego virus and Wongorr virus are also RNA viruses.

Retroviruses include alpharetroviruses (for example, Rous sarcoma virus and avian leukemia virus), betaretroviruses (for example, mouse mammary tumor virus, Mason-Pfizer monkey virus and Jaagsiekte sheep retrovirus), gammaretroviruses (for example, murine leukemia virus and feline leukemia virus, deltraretroviruses (for example, human T cell leukemia viruses (HTLV-1, HTLV-2), bovine leukemia virus, STLV-1 and STLV-2), epsilonretriviruses (for example, Walleye dermal sarcoma virus and Walleye epidermal hyperplasia virus 1), reticuloendotheliosis virus (for example, chicken syncytial virus, lentiviruses (for example, human immunodeficiency virus (HIV) type 1, human immunodeficiency virus (HIV) type 2, human immunodeficiency virus (HIV) type 3, simian immunodeficiency virus, equine infectious anemia virus, feline immunodeficiency virus, caprine arthritis encephalitis virus and Visna maedi virus) and spumaviruses (for example, human foamy virus and feline syncytia-forming virus).

Examples of DNA viruses include polyomaviruses (for example, simian virus 40, simian agent 12, BK virus, JC virus, Merkel Cell polyoma virus, bovine polyoma virus and lymphotrophic papovavirus), papillomaviruses (for example, human papillomavirus, bovine papillomavirus, adenoviruses (for example, adenoviruses A-F, canine adenovirus type 1, canined adeovirus type 2), circoviruses (for example, porcine circovirus and beak and feather disease virus (BFDV)), parvoviruses (for example, canine parvovirus), erythroviruses (for example, adeno-associated virus types 1-8), betaparvoviruses, amdoviruses, densoviruses, iteraviruses, brevidensoviruses, pefudensoviruses, herpes viruses 1, 2, 3, 4, 5, 6, 7 and 8 (for example, herpes simplex virus 1, herpes simplex virus 2, varicella-zoster virus, Epstein-Barr virus, cytomegalovirus, Kaposi's sarcoma associated herpes virus, human herpes virus-6 variant A, human herpes virus-6 variant B and cercophithecine herpes virus 1 (B virus)), poxviruses (for example, smallpox (variola), cowpox, monkeypox, vaccinia, Uasin Gishu, camelpox, psuedocowpox, pigeonpox, horsepox, fowlpox, turkeypox and swinepox), and hepadnaviruses (for example, hepatitis B and hepatitis B-like viruses). Chimeric viruses comprising portions of more than one viral genome are also contemplated herein.

For animals, in addition to the animal viruses listed above, viruses include, but are not limited to, the animal counterpart to any above listed human virus. The provided compounds can also decrease infection by newly discovered or emerging viruses. Such viruses are continuously updated on http://en.wikipedia.org/wiki/Virus and www.virology.net.

Examples of bacterial infections include, but are not limited to infections caused by the following bacteria: *Listeria* (sp.), *Franscicella tularensis*, *Mycobacterium tuberculosis*, *Rickettsia* (all types), *Ehrlichia*, *Chlamydia*. Further examples of bacteria that can be targeted by the present methods include *M. tuberculosis*, *M. bovis*, *M. bovis* strain BCG, BCG sub strains, *M. avium*, *M. intracellulare*, *M. africanum*, *M. kansasii*, *M. marinum*, *M. ulcerans*, *M. avium* subspecies paratuberculosis, *Nocardia asteroides*, other *Nocardia* species, *Legionella pneumophila*, other *Legionella* species, *Salmonella typhi*, other *Salmonella* species, *Shigella* species, *Yersinia pestis*, *Pasteurella haemolytica*, *Pasteurella multocida*, other *Pasteurella* species, *Actinobacillus pleuropneumoniae*, *Listeria monocytogenes*, *Listeria ivanovii*, *Brucella abortus*, other *Brucella* species, *Cowdria ruminantium*, *Chlamydia pneumoniae*, *Chlamydia trachomatis*, *Chlamydia psittaci*, *Coxiella burnetti*, other Rickettsial species, *Ehrlichia* species, *Staphylococcus aureus*, *Staphylococcus epidermidis*, *Streptococcus pyogenes*, *Streptococcus agalactiae*, *Bacillus anthracis*, *Escherichia coli*, *Vibrio cholerae*, *Kingella kingae*, *Campylobacter* species, *Neiserria meningitidis*, *Neiserria gonorrhea*, *Pseudomonas aeruginosa*, other *Pseudomonas* species, *Haemophilus influenzae*, *Haemophilus ducreyi*, other *Hemophilus* species, *Clostridium tetani*, other *Clostridium* species, *Yersinia enterolitica*, and other *Yersinia* species.

Examples of parasitic infections include, but are not limited to infections caused by the following parasites: *Cryptosporidium*, *Plasmodium* (all species), American trypanosomes (*T. cruzi*), African trypanosomes, *Acanthamoeba*, *Entaoeha histolytica*, *Angiostrongylus*, *Anisakis*, *Ascaris*, *Babesia*, *Balantidium*, *Baylisascaris*, lice, ticks, mites, fleas, *Capillaria*, *Clonorchis*, *Chilomastix mesnili*, *Cyclspora*, *Diphyllobothrium*, *Dipylidium caninum*, *Fasciola*, *Giardia*, *Gnathostoma*, *Hetetophyes*, *Hymenolepsis*, *Isospora*, *Loa loa*, *Microsporidia*, *Naegleria*, *Toxocara*, *Onchocerca*, *Opisthorchis*, *Paragonimus*, *Baylisascaris*, *Strongyloides*, *Taenia*, *Trichomonas* and *Trichuris*.

Furthermore, examples of protozoan and fungal species contemplated within the present methods include, but are not limited to, *Plasmodium falciparum*, other *Plasmodium* species, *Toxoplasma gondii*, *Pneumocystis carinii*, *Trypanosoma cruzi*, other trypanosomal species, *Leishmania donovani*, other *Leishmania* species, *Theileria annulata*, other *Theileria* species, *Eimeria tenella*, other *Elmeria* species, *Histoplasma capsulatum*, *Clyptococcus neoformans*, *Blastomyces dermatitidis*, *Coccidioides immitis*, *Paracoccidioides brasiliensis*, *Penicillium marneffei*, and *Candida* species. The provided compounds can also decrease infection by newly discovered or emerging bacteria, parasites or fungi, including multidrug resistant strains of same.

Further provided by the present invention is a method of inhibiting infection in a cell by a pathogen comprising decreasing expression or activity of a gene or gene product set forth in Table 1, wherein the pathogen is a respiratory virus. Respiratory viruses include, but are not limited to, picornaviruses, orthomyxoviruses, paramyxoviruses, coronaviruses and adenoviruses. More specifically, and not to be limiting, the respiratory virus can be an influenza virus, a parainfluenza virus, an adenovirus, a rhinovirus or a respiratory syncytial virus (RSV).

Also provided by the present invention is a method of inhibiting infection in a cell by a pathogen comprising decreasing expression or activity of a gene or gene product set forth in Table 1, wherein the pathogen is a gastrointestinal virus. Gastrointestinal viruses include, but are not limited to, picornaviruses, filoviruses, flaviviruses, calciviruses and reoviruses. More specifically, and not to be limiting, the gastrointestinal virus can be a reovirus, a Norwalk virus, an Ebola virus, a Marburg virus, a rotavirus, an enterovirus, a Dengue fever virus, a yellow fever virus, or a West Nile virus.

The present invention also provides a method of inhibiting infection in a cell by a pathogen comprising decreasing expression or activity of a gene or gene product set forth in Table 1, wherein the pathogen is a pox virus, BVDV, a herpes virus, HIV, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus.

Also provided is a method of inhibiting infection in a cell by a pathogen comprising decreasing expression or activity of a gene or gene product set forth in Table 1, wherein the pathogen is a pox virus, LCM, Junin virus, Machupo virus, Guanarito virus, Lassa Fever virus, hantavirus, Rift Valley Fever virus, Ebola virus, Marburg virus or Dengue Fever virus.

The present invention also provides a method of inhibiting the toxicity of a toxin in a cell and inhibiting infection in a cell by a pathogen comprising decreasing the expression or activity of a gene or a gene product set forth in Table 1, wherein the toxin is a *Clostridium perfringens* toxin, *Clostridium difficile* toxin, *Clostridium botulinum* toxin, *Clostridium tetani* toxin, saxitoxin, tetrodotoxin, abrin, conotoxin, Staphlococcal toxin, *E. coli* toxin, streptococcal toxin, diphtheria toxin, cholera toxin, pertussis toxin, *pseudomonas* toxin, *bacillus* toxin, shigatoxin, T-2 toxin, and anthrax toxin and wherein the pathogen is a pox virus, BVDV, a herpes virus, HIV, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus.

In the methods of the present invention, expression and/or activity of a gene or gene product set forth in Table 1 can be decreased by contacting the cell with any composition that can decrease expression or activity. For example, the composition can comprise a chemical, a small or large molecule (organic or inorganic), a drug, a protein, a peptide, a cDNA, an antibody, a morpholino, a triple helix molecule, an aptamer, an siRNA, a shRNA, an miRNA, an antisense RNA, a ribozyme or any other compound now known or identified in the future that decreases the expression and/or activity of a gene or gene product set forth in Table 1. A decrease in expression or activity can occur by decreasing transcription of mRNA or decreasing translation of RNA. A composition can also be a mixture or "cocktail" of two or more of the compositions described herein.

These compositions can be used alone or in combination with other therapeutic agents such as antiviral compounds, antibacterial agents, antifungal agents, antiparasitic agents, anti-inflammatory agents, anti-cancer agents, etc. All of the compounds described herein can be contacted with a cell in vitro, ex vivo or in vivo.

Examples of compounds used to treat *Clostridium difficile* include; but are not limited to, flagyl (metronidazole) and vancomycin. These antibiotics keep *C. difficile* from growing, which allows normal bacteria to flourish again in the intestine. Dificid is another drug that can be used to treat *C. difficile*. Various antibodies are also known in the art which can be used to treat *C. difficile* toxin. Disclosed herein is the treatment of *C. difficile* using antagonists to the targets disclosed in Table 1, in combination with one or more other drugs or antibodies which are known to those of skill in the art. Examples of such antibodies include, but are not limited to, those found in Lowy et al. (N Engl J Med. 2010 Jan. 21; 362(3):197-205 (hereby incorporated by reference in its entirety for its teaching concerning *C. difficile* toxin antibodies). For example, an antagonist to one of the targets of Table 1 can be used in combination with flagyl, vancomycin, dificid, or an antibody (such as Merck's CDA-1 and CDB-1), or any combination of these things.

Examples of antiviral compounds include, but are not limited to, amantadine, rimantadine, ribavirin, zanamavir (Relenza®) and oseltamavir (Tamiflu®) for the treatment of flu and its associated symptoms. Antiviral compounds useful in the treatment of HIV include Combivir® (lamivudine-zidovudine), maraviroc, Crixivan® (indinavir), Emtriva® (emtricitabine), Epivir® (lamivudine), Fortovase® (saquinavir-sg), Hivid® (zalcitabine), Invirase® (saquinavir-hg), Kaletra® (lopinavir-ritonavir), Lexiva™ (fosamprenavir), Norvir® (ritonavir), Retrovir® (zidovudine), Sustiva® (efavirenz), Videx EC® (didanosine), Videx® (didanosine), Viracept® (nelfinavir), Viramune® (nevirapine), Zerit® (stavudine), Ziagen® (abacavir), Fuzeon® (enfuvirtide), Rescriptor® (delavirdine), Reyataz® (atazanavir), Trizivir® (abacavir-lamivudine-zidovudine), Viread® (tenofovir disoproxil fumarate), Truvada® (tenofovir-emtricitabine), Atripla® (tenofovir-emtricitabine-efavirenz) and Agenerase® (amprenavir). Other antiviral compounds useful in the treatment of Ebola and other filoviruses include ribavirin and cyanovirin-N(CV-N). For the treatment of herpes virus, Zovirax (acyclovir) is available. Antibacterial agents include, but are not limited to, antibiotics (for example, penicillin and ampicillin), sulfa Drugs and folic acid Analogs, Beta-Lactams, aminoglycosides, tetracyclines, macrolides, lincosamides, streptogramins, fluoroquinolones, rifampin, mupirocin, cycloserine, aminocyclitol and oxazolidinones.

Antifungal agents include, but are not limited to, amphotericin, nystatin, terbinafine, itraconazole, fluconazole, ketoconazole, and griselfulvin.

Antiparasitic agents include, but are not limited to, antihelmintics, antinematodal agents, antiplatyhelmintic agents, antiprotozoal agents, amebicides, antimalarials, antitrichomonal agents, aoccidiostats and trypanocidal agents.

Antibodies

The present invention also provides antibodies that specifically bind to the gene products, proteins and fragments thereof set forth in Table 1. The antibody of the present invention can be a polyclonal antibody or a monoclonal antibody. The antibody of the invention selectively binds a polypeptide. By "selectively binds" or "specifically binds" is meant an antibody binding reaction which is determinative of the presence of the antigen (in the present case, a polypeptide set forth in Table 1 or antigenic fragment thereof among a heterogeneous population of proteins and other biologics). Thus, under designated immunoassay conditions, the specified antibodies bind preferentially to a particular peptide and do not bind in a significant amount to other proteins in the sample. Preferably, selective binding includes binding at about or above 1.5 times assay background and the absence of significant binding is less than 1.5 times assay background.

This invention also contemplates antibodies that compete for binding to natural interactors or ligands to the proteins set forth in Table 1. In other words, the present invention provides antibodies that disrupt interactions between the proteins set forth in Table 1 and their binding partners. For example, an antibody of the present invention can compete with a protein for a binding site (e.g. a receptor) on a cell or the antibody can compete with a protein for binding to another protein or biological molecule, such as a nucleic acid that is under the transcriptional control of a transcription factor set forth in Table 1. An antibody can also disrupt the interaction between a protein set forth in Table 1 and a pathogen, or the product of a pathogen. For example, an antibody can disrupt the interaction between a protein set forth in Table 1 and a toxin, a viral protein, a bacterial protein, a parasitic protein, or a fungal protein. The antibody optionally can have either an antagonistic or agonistic function as compared to the antigen. Antibodies which antagonize pathogenic infection are utilized to decrease infection.

Preferably, the antibody binds a polypeptide in vitro, ex vivo or in vivo. Optionally, the antibody of the invention is labeled with a detectable moiety. For example, the detectable moiety can be selected from the group consisting of a fluorescent moiety, an enzyme-linked moiety, a biotin moiety and a radiolabeled moiety. The antibody can be used in techniques or procedures such as diagnostics, screening, or imaging. Anti-idiotypic antibodies and affinity matured antibodies are also considered to be part of the invention.

As used herein, the term "antibody" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. Such antibodies and fragments can be made by techniques known in the art and can be screened for specificity and activity according to the methods set forth in the Examples and in general methods for producing antibodies and screening antibodies for specificity and activity (See Harlow and Lane, Antibodies, A Laboratory Manual. Cold Spring Harbor Publications, New York, (1988)).

Also included within the meaning of "antibody" are conjugates of antibody fragments and antigen binding proteins (single chain antibodies) as described, for example, in U.S. Pat. No. 4,704,692, the contents of which are hereby incorporated by reference.

Optionally, the antibodies are generated in other species and "humanized" for administration in humans. In one embodiment of the invention, the "humanized" antibody is a human version of the antibody produced by a germ line mutant animal. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin.

Humanized antibodies include human immunoglobulins (recipient antibody) in which residues from a CDR of the recipient are replaced by residues from a CDR of a non-human species (donor antibody) such as mouse, rat or rabbit having the desired specificity, affinity and capacity. In one embodiment, the present invention provides a humanized version of an antibody, comprising at least one, two, three, four, or up to all CDRs of a monoclonal antibody that specifically binds to a protein or fragment thereof set forth in Table 1. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Examples of antibodies that correspond with the proteins of Table 1 are as follows:

TABLE 2

| HUGO Gene Name | Antibody |
| --- | --- |
| AP2S1 | EPR2696 (Abcam) |
| AREG | LS-B1048 (LS BIO) |
| ARL61P1 | SAB1400447 (Sigma Aldrich) |
| ATAD4 | HPA022918 (Sigma Aldrich) |
| BRP44 | 00025874-M03 (Novus Biologicals) |
| C20ORF72 | Ab95093 (Abcam) |
| CCNG1 | 10897-1-AP (Protein Tech Group) |
| CDH17 | WH0001015M1 (Sigma Aldrich) |
| CPEB4 | Ab83009 (Abcam) |
| DCAF6 | ABIN252404 |
| DRG1 | Ab80869 (Abcam) |
| EHD1 | Ab75886 (Abcam) |

TABLE 2-continued

| HUGO Gene Name | Antibody |
| --- | --- |
| EIF3B | Ab50709 (Abcam) |
| FGL1 | H00002267-MO1 (Novus Bio) |
| FNDC1 | Sc-107546 (Santa Cruz Biotechnology) |
| HIST1H2B1 | |
| HNRNPH1 | 14774-1-AP (PTG Labs) |
| LGALS3 | Ls-c106930 (LS BIO) |
| LGALS3BP | Ab81489 (Abcam) |
| N4BP2L2 | Ag10568 (PTG Labs) |
| PLIN2 | NBP1-39469 (Novus Bio) |
| POU3F3 | Ab90727 (Abcam) |
| PRR15L | HPA022918 (Sigma Aldrich) |
| PVRL3 | 1100025945-B01P (Novus Bio) |
| RAB3B | Ab55655 (Abcam) |
| RPS15A | Ab91071 (Abcam) |
| RSPH3 | 17603-1-AP (PTG Labs) |
| SC5DL | Ab90008 (Abcam) |
| SEC31A | HPA005457 (Sigma Aldrich) |
| SNX5 | Ab5383 (Abcam) |
| TM4SF1 | HPA002823 (Sigma Aldrich) |
| TTR | HPA002550 (Sigma Aldrich) |

Peptides

Peptides that inhibit expression or activity of a gene or a gene product set forth in Table 1 are also provided herein. Peptide libraries can be screened utilizing the screening methods set forth herein to identify peptides that inhibit activity of any of the genes or gene products set forth in Table 1. These peptides can be derived from a protein that binds to any of the genes or gene products set forth in Table 1. These peptides can be any peptide in a purified or non-purified form, such as peptides made of D- and/or L-configuration amino acids (in, for example, the form of random peptide libraries; see Lam et al., Nature 354:82-4, 1991), phosphopeptides (such as in the form of random or partially degenerate, directed phosphopeptide libraries; see, for example, Songyang et al., Cell 72:767-78, 1993).

siRNAs

Short interfering RNAs (siRNAs), also known as small interfering RNAs, are double-stranded RNAs that can induce sequence-specific post-transcriptional gene silencing, thereby decreasing gene expression (See, for example, U.S. Pat. Nos. 6,506,559, 7,056,704, 7,078,196, 6,107,094, 5,898,221, 6,573,099, and European Patent No. 1,144,623, all of which are hereby incorporated in their entireties by this reference). siRNAs can be of various lengths as long as they maintain their function. In some examples, siRNA molecules are about 19-23 nucleotides in length, such as at least 21 nucleotides, for example at least 23 nucleotides. In one example, siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends. The direction of dsRNA processing determines whether a sense or an anti sense target RNA can be cleaved by the produced siRNA endonuclease complex. Thus, siRNAs can be used to modulate transcription or translation, for example, by decreasing expression of a gene set forth in Table 1. The effects of siRNAs have been demonstrated in cells from a variety of organisms, including Drosophila, C. elegans, insects, frogs, plants, fungi, mice and humans (for example, WO 02/44321; Gitlin et al., Nature 418:430-4, 2002; Caplen et al., Proc. Natl. Acad. Sci. 98:9742-9747, 2001; and Elbashir et al., Nature 411:494-8, 2001).

Utilizing sequence analysis tools, one of skill in the art can design siRNAs to specifically target one or more of the genes set forth in Table 1 for decreased gene expression. siRNAs that inhibit or silence gene expression can be obtained from numerous commercial entities that synthesize siRNAs, for example, Ambion Inc. (2130 Woodward Austin, Tex. 78744-1832, USA), Qiagen Inc. (27220 Tumberry Lane, Valencia, Calif. USA) and Dharmacon Inc. (650 Crescent Drive, #100 Lafayette, Colo. 80026, USA). The siRNAs synthesized by Ambion Inc., Qiagen Inc. or Dharmacon Inc, can be readily obtained from these and other entities by providing a GenBank Accession No. for the mRNA of any gene set forth in Table 1. In addition, siRNAs can be generated by utilizing Invitrogen's BLOCK-JT™ RNAi Designer https://rnaidesigner.invitrogen.com/maiexpress. siRNA sequences can comprise a 3' TT overhang and/or additional sequences that allow efficient cloning and expression of the siRNA sequences. siRNA sequences can be cloned into vectors and utilized in vitro, ex vivo or in vivo to decrease gene expression. One of skill in the art would know that it is routine to utilize publicly available algorithms for the design of siRNA to target mRNA sequences. These sequences can then be assayed for inhibition of gene expression in vitro, ex vivo or in vivo.

Examples of siRNA sequences that can be utilized in the methods described herein include, but are not limited to those set forth in Table 3 below. Specifically, the sense siRNA sequences set forth below and sequences complementary to these sequences can be used alone or in combination with other sequences to inhibit gene expression. Also contemplated are siRNA sequences that are shorter or longer than the sequences set forth below. For example, an siRNA sequence comprising any of the sequences set forth below can be readily generated by adding nucleotides, on one or both ends of the siRNA, that flank these sequences in the full-length mRNA for the gene of interest. Nucleotides can also be removed, from one or both ends of the siRNA to generate shorter siRNA sequences that retain their function. These sequences can comprise a 3'TT overhang and/or additional sequences that allow efficient cloning and expression of the siRNA sequences. All of the sequences disclosed herein can be cloned into vectors and utilized in vitro, ex vivo or in vivo to decrease gene expression. These siRNA sequences are merely exemplary as one of skill in the art would know that it is routine to utilize publicly available algorithms for the design of siRNA to target mRNA sequences. It is understood that any siRNA sequence set forth in the present application also includes disclosure of its reverse complement to produce siRNA duplexes. These sequences can then be assayed for inhibition of gene expression in vitro, ex vivo or in vivo.

TABLE 3

SiRNA

| HUGO Gene Name | siRNA | Human Genbank RNA accession number |
|---|---|---|
| AP2S1 | TGATCCGCTTTATCCTCATCCAGAA (SEQ ID NO: 1)<br>CGAGACGCCAAACACACCAACTTTG (SEQ ID NO: 2)<br>CCAAACACACCAACTTTGTGGAGTT (SEQ ID NO: 3)<br>CAACTTTGTGGAGTTCCGGAACTTT (SEQ ID NO: 4)<br>ACTTTGTGGAGTTCCGGAACTTTAA (SEQ ID NO: 5) | NM_004069.3 |
| AREG | GCTCAGGCCATTATGCTGCTGGATT (SEQ ID NO: 6)<br>CATTATGCTGCTGGATTGGACCTCA (SEQ ID NO: 7)<br>GCTGCTGGATTGGACCTCAATGACA (SEQ ID NO: 8)<br>CCTACTCTGGGAAGCGTGAACCATT (SEQ ID NO: 9)<br>GGGACCACAGTGCTGATGGATTTGA (SEQ ID NO: 10) | NM_001657.2 |
| ARL61P1 | GAGATAATCGCAGCACCAACCTGCT (SEQ ID NO: 11)<br>GAGAAGTGATGCTGATGGCTGATAA (SEQ ID NO: 12)<br>AGAAGTGATGCTGATGGCTGATAAA (SEQ ID NO: 13)<br>GGTGTGGTTTCTTTGGTGTTTCTGA (SEQ ID NO: 14)<br>GATCCATCTGTTCTGTCCGGCGTTT (SEQ ID NO: 15) | NM_015161.1 |
| BRP44 | GGCTCCTCGATAAAGTGGAGCTGAT (SEQ ID NO: 16)<br>GCTCCTCGATAAAGTGGAGCTGATG (SEQ ID NO: 17)<br>GAGCTGATGCTGCCCGAGAAATTGA (SEQ ID NO: 18)<br>TGCCCGAGAAATTGAGGCCGTTGTA (SEQ ID NO: 19)<br>CCCGAGAAATTGAGGCCGTTGTACA (SEQ ID NO: 20) | NM_001143674.1 |
| C20ORF72 | CCTTGTGGCTTTCTCTACTTCCTCT (SEQ ID NO: 21)<br>GAGCAAGCATAAGCTGCCAAACCAA (SEQ ID NO: 22)<br>CAAGTGATCCTTCAGTTCCTTTGAA (SEQ ID NO: 23)<br>GGAACTGGGAGAAGATGGCTTTAAA (SEQ ID NO: 24)<br>GAACTGGGAGAAGATGGCTTTAAAG (SEQ ID NO: 25) | NM_052865.2 |
| CCNGI | GAGACTAATTGAGTCTGCACACGAT (SEQ ID NO: 26)<br>TGGCCTCAGAATGACTGCAAGACTA (SEQ ID NO: 27)<br>CAAGACTAAGGGACTTTGAAGTAAA (SEQ ID NO: 28)<br>CCATTGGCAACTGACTTGATCCGAA (SEQ ID NO: 29)<br>TGGAGAAGGTGTGTTGGAAAGTCAA (SEQ ID NO: 30) | NM_004060.3 |
| CDH17 | CAGGAAAGCCCTTCTTGTATGTCAA (SEQ ID NO: 31)<br>CCACTCCCAATGGCCAGCTTTATTA (SEQ ID NO: 32)<br>CATATCCGCTGGAAATTCATGTAAA (SEQ ID NO: 33)<br>CAAGATACTCCTCAGTACAACTTAA (SEQ ID NO: 34)<br>CACAAACATTGGGTCCACCATCTTA (SEQ ID NO: 35) | NM_001144663.1 |

TABLE 3-continued siRNA

| HUGO Gene Name | siRNA | Human Genbank RNA accession number |
|---|---|---|
| CPEB4 | CGGCTAATAACGGTGCTCTGTTGTT(SEQ ID NO: 36)<br>CCAGCTGCCTCATTTGGCGAATAAT(SEQ ID NO: 37)<br>CCCTGAACTCCATCTCGCCTTTGAA(SEQ ID NO: 38)<br>CAAGCAATCATATTCAGCTCCAGAA(SEQ ID NO: 39)<br>CAGGATCCGATAGCTCTCTGCTTAT(SEQ ID NO: 40) | |
| DCAF6 | CCTTAATGTGCATGATGGTTGTGTT(SEQ ID NO: 41)<br>CAGACAATGCCAATTTACGTGTCAT(SEQ ID NO: 42)<br>GATGGAACTGTTAGGTGGTTTGATA(SEQ ID NO: 43)<br>CCCGAAAGATGATACAGCACGAGAA(SEQ ID NO: 44)<br>GATGCAGAGAATGTCTGATATGTTA(SEQ ID NO: 45) | NM_018442.2 |
| DRGI | GCACCTTAGCTAAGATCGCGGAGAT(SEQ ID NO: 46)<br>CACCTTAGCTAAGATCGCGGAGATA(SEQ ID NO: 47)<br>CCTTAGCTAAGATCGCGGAGATAGA(SEQ ID NO: 48)<br>GAGATAGAAGCAGAGATGGCTCGGA(SEQ ID NO: 49)<br>GATAGAAGCAGAGATGGCTCGGACT(SEQ ID NO: 50) | NM_004147.3 |
| EHDI | TCAGGAAGCTCAATGACCTGATCAA(SEQ ID NO: 51)<br>GCCAAGGTTCACGCCTACATCATCA(SEQ ID NO: 52)<br>CCTACATCATCAGCTCCCTCAAGAA(SEQ ID NO: 53)<br>GCTCCCTCAAGAAAGAGATGCCCAA(SEQ ID NO: 54)<br>CCTCAAGAAAGAGATGCCCAATGTC(SEQ ID NO: 55) | NM_006795.2 |
| EIF3B | CACACATTCCGGGTCAACCTCTTTA(SEQ ID NO: 56)<br>GATCAGTGACGAGTGGGATATTCCA(SEQ ID NO: 57)<br>GGAACTTACGTTACTGGCTTGAAGA(SEQ ID NO: 58)<br>GCTTATTGACTTCTCACCTTGTGAA(SEQ ID NO: 59)<br>GAGATCCGAGTGAGGAACCTGTTCA(SEQ ID NO: 60) | NM_001037283.1 |
| FGL1 | AGGAGATGAGAATACTGTCATTGAT(SEQ ID NO: 61)<br>GAGATGAGAATACTGTCATTGATCT(SEQ ID NO: 62)<br>CAAGAGGCAGTATGCAGATTGTTCA(SEQ ID NO: 63)<br>CAGTATGCAGATTGTTCAGAGATTT(SEQ ID NO: 64)<br>GACTGTAATTCAGAGACGATCTGAT(SEQ ID NO: 65) | NM_004467.3 |
| FNDC1 | AGGAGATGAGAATACTGTCATTGAT(SEQ ID NO: 66)<br>GAGATGAGAATACTGTCATTGATCT(SEQ ID NO: 67)<br>CAAGAGGCAGTATGCAGATTGTTCA(SEQ ID NO: 68)<br>CAGTATGCAGATTGTTCAGAGATTT(SEQ ID NO: 69)<br>GACTGTAATTCAGAGACGATCTGAT(SEQ ID NO: 70) | NM_032532.2 |
| HIST1H2B1 | GCAAGGAGAGCTATTCCGTGTACGT(SEQ ID NO: 71)<br>CAAGGAGAGCTATTCCGTGTACGTG(SEQ ID NO: 72)<br>AGGAGAGCTATTCCGTGTACGTGTA(SEQ ID NO: 73)<br>GAGAGCTATTCCGTGTACGTGTACA(SEQ ID NO: 74)<br>GCTATTCCGTGTACGTGTACAAGGT(SEQ ID NO: 75) | NM_003525.2 |
| HNRNPH1 | AAGAATAGGGCACAGGTATATTGAA(SEQ ID NO: 76)<br>GAATAGGGCACAGGTATATTGAAAT(SEQ ID NO: 77)<br>AGGGCACAGGTATATTGAAATCTTT(SEQ ID NO: 78)<br>GGGCACAGGTATATTGAAATCTTTA(SEQ ID NO: 79)<br>GGTAGAGGGTATAACAGCATTGGCA(SEQ ID NO: 80) | NM_005520.2 |
| LGALS3 | CCATGATGCGTTATCTGGGTCTGGA(SEQ ID NO: 81)<br>TGCTGGGCCACTGATTGTGCCTTAT(SEQ ID NO: 82)<br>GCTGGGCCACTGATTGTGCCTTATA(SEQ ID NO: 83)<br>TGATTGTGCCTTATAACCTGCCTTT(SEQ ID NO: 84)<br>TGGTGCCTCGCATGCTGATAACAAT(SEQ ID NO: 85) | NM_002306.3 |
| LGALS3BP | GCTGGTGTGGTCTGCACCAATGAAA(SEQ ID NO: 86)<br>ACCTGTCCATCAGCGTGAATGTGCA(SEQ ID NO: 87)<br>GCAGCAATGTCACCATGAGTGTGGA(SEQ ID NO: 88)<br>AGGGACCTTCTCAGGTACTTCTACT(SEQ ID NO: 89)<br>CAGGTACTTCTACTCCCGAAGGATT(SEQ ID NO: 90) | NM_005567.3 |
| LOC645960 | ACGGAAACCTGTGCCATTCTGTGTA(SEQ ID NO: 91)<br>CGGAAACCTGTGCCATTCTGTGTAT(SEQ ID NO: 92)<br>GCCATTCTGTGTATGAGAACGTTTG(SEQ ID NO: 93)<br>CATTCTGTGTATGAGAACGTTTGCA(SEQ ID NO: 94)<br>GAGGCCCTATGCAAGGCCAACTTTA(SEQ ID NO: 95) | XM_002342818.1 |

TABLE 3-continued siRNA

| HUGO Gene Name | siRNA | Human Genbank RNA accession number |
|---|---|---|
| M1R192 | GCTGCCAATTCCATAGGTCACAGGT(SEQ ID NO: 96)<br>TGCCAATTCCATAGGTCACAGGTAT(SEQ ID NO: 97)<br>GCCAATTCCATAGGTCACAGGTATG(SEQ ID NO: 98)<br>CCAATTCCATAGGTCACAGGTATGT(SEQ ID NO: 99)<br>CAATTCCATAGGTCACAGGTATGTT(SEQ ID NO: 100) | NR_029578.1 |
| M1R194-2 | CCCTGTAACAGCAACTCCATGTGGA(SEQ ID NO: 101) | NR_029829.1 |
| N4BP2L2 | GAGGACATAGTTATTTGCAGGAGAA(SEQ ID NO: 102)<br>CAGTTGTAAAGAATCTGAACCTTCT(SEQ ID NO: 103)<br>GAGGGTCATAATAATGGTCTCTTAA(SEQ ID NO: 104)<br>CATGTTAACTGGAATTGCATGACTT(SEQ ID NO: 105)<br>CAAGCATAATGGAACAGACAGGTTT(SEQ ID NO: 106) | NM_014887.2 |
| PL1N2 | GAGAACGGTGTGAAGACCATCACCT(SEQ ID NO: 107)<br>CAGCAGGGTTAAAGAAGCTAAGCAA(SEQ ID NO: 108)<br>CATTTCTCAGCTCCATTCTACTGTT(SEQ ID NO: 109)<br>TCACCTGATTGAATTTGCCAGGAAG(SEQ ID NO: 110)<br>GAGCATTGGATATGATGATACTGAT(SEQ ID NO: 111) | NM_001122.2 |
| POU3F3 | CAGCTGAGCTTCAAGAACATGTGCA(SEQ ID NO: 112)<br>AGCTGAGCTTCAAGAACATGTGCAA(SEQ ID NO: 113)<br>GCTTCAAGAACATGTGCAAGCTCAA(SEQ ID NO: 114)<br>AGAACATGTGCAAGCTCAAGCCGCT(SEQ ID NO: 115) | NM_006236.1 |
| PRR15L | GCTGTATGAGATCCCTGACACCTAT(SEQ ID NO: 116)<br>TCCCTGACACCTATGCCCAAACAGA(SEQ ID NO: 117)<br>CACCTATGCCCAAACAGAGGGAGAT(SEQ ID NO: 118)<br>TGCCCAAACAGAGGGAGATGCAG   (SEQ ID NO: 119)<br>GAGAAGATTGTGGACAAGAGCACAA(SEQ ID NO: 120) | NM_024320.2 |
| PVRL3 | GAATATCAGGGAAGAGTCTTGTTTA(SEQ ID NO: 121)<br>ACGGCAACGATTATCAGCCAGTACA(SEQ ID NO: 122)<br>CCAGTACAAGCTATTTCCAACCAGA(SEQ ID NO: 123)<br>TAGAGGAAGGCGAATTACTTGTGTT(SEQ ID NO: 124)<br>GAAGGCGAATTACTTGTGTTGTAAA(SEQ ID NO: 125) | NM_015480.1 |
| RAB3B | TGAAGACAGTCTACCGTCACGAGAA(SEQ ID NO: 126)<br>GGGCCATGGGCTTCATTCTGATGTA(SEQ ID NO: 127)<br>CCATGGGCTTCATTCTGATGTATGA(SEQ ID NO: 128)<br>CATCACCAATGAAGAGTCCTTCAAT(SEQ ID NO: 129)<br>CACCAATGAAGAGTCCTTCAATGCT(SEQ ID NO: 130) | NM_002H67.3 |
| RSPH3 | GCATCAAAGCCAAGCTCCACCGAAA(SEQ ID NO: 131)<br>AAGGGTAATTCGAGGTAACACTTAT(SEQ ID NO: 132)<br>GAAAGCATGTCGATGTGCAAACAGA(SEQ ID NO: 133)<br>GACAGACCACCAACACCACTCTTTA(SEQ ID NO: 134)<br>GGAAGACAATTGAGCAGTCTCTTCT(SEQ ID NO: 135) | NM_031924.4 |
| SC5DL | CATCTTCCGACAAGCTATTAGTCTT(SEQ ID NO: 136)<br>GACAAGCTATTAGTCTTCTGATTGT(SEQ ID NO: 137)<br>CAAGTCCGTCGAGAGATTAAGTTTA(SEQ ID NO: 138)<br>GAGGTTACAGCAAATTACATGATGA(SEQ ID NO: 138)<br>GCCTTCATCATAGACTGGTATATAA(SEQ ID NO: 140) | NM_001024956.2 |
| SEC31A | GCTCAGCAATTGGATGCAACATTTA(SEQ ID NO: 141)<br>CAAGGAAGTTGTGATTGCCCAGAAT(SEQ ID NO: 142)<br>CCAGACTAATCTGGTAGCTTCTGGT(SEQ ID NO: 143)<br>GAGCATGGCAGATCCTGAATTGTTA(SEQ ID NO: 144)<br>CAGAAACAAGTTGACAAGCTTTCAT(SEQ ID NO: 145) | NM_001077207.2 |
| SLCO2B1 | CGGCCAAGTGTGTTCCATAACATCA(SEQ ID NO: 146)<br>TCCATAACATCAAGCTGTTCGTTCT(SEQ ID NO: 147)<br>CAGCTCATGATCTCCGGCTACCTAA(SEQ ID NO: 148)<br>GATATGCCACAGGACTTCAAGGCTT(SEQ ID NO: 149)<br>GGCAACTGCTCAAGCTACACAGAAA(SEQ ID NO: 150) | NM_007256.3 |
| SNORA25 | GGGTCATTTCAAAGAGGGCTTATGA(SEQ ID NO: 151)<br>GGTCATTTCAAAGAGGGCTTATGAG(SEQ ID NO: 152)<br>CATTTCAAAGAGGGCTTATGAGGCT(SEQ ID NO: 153)<br>CAAAGAGGGCTTATGAGGCTGTGAA(SEQ ID NO: 154)<br>AAAGAGGGCTTATGAGGCTGTGAAA(SEQ ID NO: 155) | NR_00302&.1 |

TABLE 3-continued siRNA

| HUGO Gene Name | siRNA | Human Genbank RNA accession number |
|---|---|---|
| SNORD17 | TGTTCTACTGTGAACTGCTTGTGTG (SEQ ID NO: 156)<br>GAACTGCTTGTGTGTTGGCAGGCTA (SEQ ID NO: 157)<br>TGTTGGCAGGCTACCGGTAAGAATG (SEQ ID NO: 158)<br>TGGCAGGCTACCGGTAAGAATGGTT (SEQ ID NO: 159)<br>GGCTACCGGTAAGAATGGTTGGTGT (SEQ ID NO: 160) | NR_003045.1 |
| SNX5 | CCGCAGCAAGCTGAGATCTGTATCT (SEQ ID NO: 161)<br>CAGCAAGCTGAGATCTGTATCTGTG (SEQ ID NO: 162)<br>CATGAAGACTTTGTGTGGCTACATG (SEQ ID NO: 163)<br>ACAACAGACTATGCTGGGCTTATTA (SEQ ID NO: 164)<br>CAACAGACTATGCTGGGCTTATTAT (SEQ ID NO: 165) | NM_014426.2 |
| TM4SF1 | CCTCCTGTGCATCGCGGCTAATATT (SEQ ID NO: 166)<br>TCTGTATTGGCTGCTCTCATTGGAA (SEQ ID NO: 167)<br>GCACTGAACCCAAGCACATTGTGGA (SEQ ID NO: 168)<br>AACCCAAGCACATTGTGGAATGGAA (SEQ ID NO: 169)<br>ACCCAAGCACATTGTGGAATGGAAT (SEQ ID NO: 170) | NM_014220.2 |
| TTR | CCGGTGAATCCAAGTGTCCTCTGAT (SEQ ID NO: 171)<br>CGGTGAATCCAAGTGTCCTCTGATG (SEQ ID NO: 172)<br>CAAGTGTCCTCTGATGGTCAAAGTT (SEQ ID NO: 173)<br>AGTGTCCTCTGATGGTCAAAGTTCT (SEQ ID NO: 174)<br>CCATCAATGTGGCCGTGCATGTGTT (SEQ ID NO: 175) | NM_000371.3 | shRNA shRNA (short hairpin RNA) is a DNA molecule that can be cloned into expression vectors to express siRNA (typically 19-29 nt RNA duplex) for RNAi interference studies. shRNA has the following structural features: a short nucleotide sequence ranging from about 19-29 nucleotides derived from the target gene, followed by a short spacer of about 4-15 nucleotides (i.e. loop) and about a 19-29 nucleotide sequence that is the reverse complement of the initial target sequence.

Antisense Nucleic Acids

Generally, the term "antisense" refers to a nucleic acid molecule capable of hybridizing to a portion of an RNA sequence (such as mRNA) by virtue of some sequence complementarity. The antisense nucleic acids disclosed herein can be oligonucleotides that are double-stranded or single-stranded, RNA or DNA or a modification or derivative thereof, which can be directly administered to a cell (for example by administering the antisense molecule to the subject), or which can be produced intracellularly by transcription of exogenous, introduced sequences (for example by administering to the subject a vector that includes the antisense molecule under control of a promoter).

Antisense nucleic acids are polynucleotides, for example nucleic acid molecules that are at least 6 nucleotides in length, at least 10 nucleotides, at least 15 nucleotides, at least 20 nucleotides, at least 100 nucleotides, at least 200 nucleotides, such as 6 to 100 nucleotides. However, antisense molecules can be much longer. In particular examples, the nucleotide is modified at one or more base moiety, sugar moiety, or phosphate backbone (or combinations thereof), and can include other appending groups such as peptides, or agents facilitating transport across the cell membrane (Letsinger et al., *Proc. Natl. Acad. Sci. USA* 1989, 86:6553-6; Lemaitre et al., *Proc. Natl. Acad. Sci. USA* 1987, 84:648-52; WO 88/09810) or blood-brain barrier (WO 89/10134), hybridization triggered cleavage agents (Krol et al., *Bio-Techniques* 1988, 6:958-76) or intercalating agents (Zon, *Pharm. Res.* 5:539-49, 1988). Additional modifications include those set forth in U.S. Pat. Nos. 7,176,296: 7,329,648; 7,262,489, 7,115,579; and 7,105,495.

Examples of modified base moieties include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyl adenine, 1-methylguanine, 1-methylinosine, 2,2-dimethylguanine, 2-methyl adenine, 2-methylguanine, 3-methyl cytosine, 5-methyl cytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine.

Examples of modified sugar moieties include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

In a particular example, an antisense molecule is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625-41, 1987). The oligonucleotide can be conjugated to another molecule, such as a peptide, hybridization triggered cross-linking agent, transport agent, or hybridization-triggered cleavage agent. Oligonucleotides can include a targeting moiety that enhances uptake of the molecule by host cells. The targeting moiety can be a specific binding molecule, such as an antibody or fragment thereof that recognizes a molecule present on the surface of the host cell.

In a specific example, antisense molecules that recognize a nucleic acid set forth herein, include a catalytic RNA or a ribozyme (for example see WO 90/11364; WO 95/06764; and Sarver et al., *Science* 247:1222-5, 1990). Conjugates of antisense with a metal complex, such as terpyridylCu (II), capable of mediating mRNA hydrolysis, are described in Bashkin et al. (*Appl. Biochem Biotechnol.* 54:43-56, 1995). In one example, the antisense nucleotide is a 2'-0-methyl-ribonucleotide (Inoue et al., Nucl. Acids Res. 15:6131-48, 1987), or a chimeric RNA-DNA analogue (Inoue et al., *FEBS Lett.* 215:327-30, 1987). Antisense molecules can be generated by utilizing the Antisense Design algorithm of Integrated DNA Technologies, Inc. (1710 Commercial Park, Coralville, Iowa 52241 USA; http://www.idtdna.com/Scitools/Applications/AntiSense/Antisense.aspx.

Any antisense sequence that is not the full length mRNA for any of the genes listed in Table 1 can be used as antisense sequences. It is known to those of skill in the art that once an mRNA sequence is routinely obtained for any of the genes set forth in Table 1, it is routine to walk along the mRNA sequence to generate anti sense sequences that decrease expression of the gene. Therefore, the methods of the present invention can utilize any antisense sequence that decreases the expression of a gene set forth in Table 1.

Antisense molecules can be generated by utilizing the Antisense Design algorithm of Integrated DNA Technologies, Inc. (1710 Commercial Park, Coralville, Iowa 52241 USA; http://www.idtdna.com/Scitools/Applications/AntiSense/Antisense.aspx/)

Examples of antisense nucleic acid molecules that can be utilized to decrease expression in the methods of the present invention, include, but are not limited to those found in Table 3, below:

TABLE 4

ANTISENSE RNA

| HUGO Gene Name | Antisense | | Human Genbank RNA accession number |
|---|---|---|---|
| AP2S1 | 5' CTTCGTCTGGCTGGTCTCTC 3' | (SEQ ID NO: 176) | NM 004069.3 |
| | 5' GTCTGGCTGGTCTCTCGGAT 3' | (SEQ ID NO: 177) | |
| | 5' GTCTGGCTGGTCTCTCGGATT 3' | (SEQ ID NO: 178) | |
| | 5' CCTTCGTCTGGCTGGTCTCT 3' | (SEQ ID NO: 179) | |
| | 5' CTTCGTCTGGCTGGTCTCT 3' | (SEQ ID NO: 180) | |
| AREG | 5' GGCTCTCATTGGTCCTTCGCA 3' | (SEQ ID NO: 181) | NM 001657.2 |
| | 5' GGCTCTCATTGGTCCTTCGC 3' | (SEQ ID NO: 182) | |
| | 5' GAGTAGTCATAGTCGGCTCCC 3' | (SEQ ID NO: 183) | |
| | 5' AGTAGTCATAGTCGGCTCCC 3' | (SEQ ID NO: 184) | |
| | 5' GTAGTCATAGTCGGCTCCC 3' | (SEQ ID NO: 185) | |
| ARL61P1 | 5' ATTATCTCCCTCCGCCATC 3' | (SEQ ID NO: 186) | NM 015161.1 |
| | 5' ATTATCTCCCTCCGCCATCG 3' | (SEQ ID NO: 187) | |
| | 5' TTATCTCCCTCCGCCATCG 3' | (SEQ ID NO: 188) | |
| | 5' TTGTTGTCCCACCCAAGCA 3' | (SEQ ID NO: 189) | |
| | 5' ATCTCCCTCCGCCATCGTCT 3' | (SEQ ID NO: 190) | |
| ATAD4 | 5' CACTCTCTCCATTCCCTGCCA 3' | (SEQ ID NO: 191) | NM 024320.2 |
| | 5' ACTCTCTCCATTCCCTGCCA 3' | (SEQ ID NO: 192) | |
| | 5' TCACTCTCTCCATTCCCTGCC 3' | (SEQ ID NO: 193) | |
| | 5' ACTCTCTCCATTCCCTGCCAT 3' | (SEQ ID NO: 194) | |
| | 5' CACTCTCTCCATTCCCTGCC 3' | (SEQ ID NO: 195) | |
| BRP44 | 5' GTGTTCTCGTCCCTGGCTGT 3' | (SEQ ID NO: 196) | NM 001143674.1 |
| | 5' GTTCTCGTCCCTGGCTGTTGT 3' | (SEQ ID NO: 197) | |
| | 5' GTGTTCTCGTCCCTGGCTGTT 3' | (SEQ ID NO: 198) | |
| | 5' TGTGTTCTCGTCCCTGGCTGT 3' | (SEQ ID NO: 199) | |
| | 5' CTGTGTTCTCGTCCCTGGCT 3' | (SEQ ID NO: 200) | |
| C20ORF72 | 5' GCCATCTTCTCCCAGTTCCA 3' | (SEQ ID NO: 201) | NM 052865.2 |
| | 5' GCCATCTTCTCCCAGTTCCAG 3' | (SEQ ID NO: 202) | |
| | 5' GCCATCTTCTCCCAGTTCC 3' | (SEQ ID NO: 203) | |
| | 5' AGCCATCTTCTCCCAGTTCC 3' | (SEQ ID NO: 204) | |
| | 5' AGCCATCTTCTCCCAGTTCCA 3' | (SEQ ID NO: 205) | |
| CCNG1 | 5' GTCCCTTAGTCTTGCAGTCA 3' | (SEQ ID NO: 206) | NM 004060.3 |
| | 5' AGTCCCTTAGTCTTGCAGTCA 3' | (SEQ ID NO: 207) | |
| | 5' GTCCCTTAGTCTTGCAGTCAT 3' | (SEQ ID NO: 208) | |
| | 5' AGTCCCTTAGTCTTGCAGTC 3' | (SEQ ID NO: 209) | |
| | 5' GTCCCTTAGTCTTGCAGTC 3' | (SEQ ID NO: 210) | |
| CDH17 | 5' ACTCCCTCTCCTCAAACTCT 3' | (SEQ ID NO: 211) | NM 001144663.1 |
| | 5' GCCTCCCATGTCCTTCACT 3' | (SEQ ID NO: 212) | |
| | 5' CTCCCTCTCCTCAAACTCT 3' | (SEQ ID NO: 213) | |
| | 5' CGACATACTCCCTCTCCTCA 3' | (SEQ ID NO: 214) | |
| | 5' ACGACATACTCCCTCTCCTCA 3' | (SEQ ID NO: 215) | |

TABLE 4-continued

ANTISENSE RNA

| HUGO Gene Name | Antisense | | Human Genbank RNA accession number |
|---|---|---|---|
| CPEB4 | 5' CCTTCTTCCTCCTCTTCCTCC 3' | (SEQ ID NO: 216) | NM 030627.2 |
| | 5' TCTTCCTCCTCTTCCTCCTCT 3' | (SEQ ID NO: 217) | |
| | 5' CTTCCTCCTCTTCCTCCTCT 3' | (SEQ ID NO: 218) | |
| | 5' TCTTCCTCCTCTTCCTCCTC 3' | (SEQ ID NO: 219) | |
| | 5' CTTCTTCCTCCTCTTCCTCCT 3' | (SEQ ID NO: 220) | |
| DCAF6 | 5' ACTCTTCTCTTCTCTCTTCC 3' | (SEQ ID NO: 221) | NM 018442.2 |
| | 5' CTCGCCTCATACTCTCCTTCT 3' | (SEQ ID NO: 222) | |
| | 5' CTCTTCTCTTCTCTCTTCC 3' | (SEQ ID NO: 223) | |
| | 5' ACTCTTCTCTTCTCTCTTCCG 3' | (SEQ ID NO: 224) | |
| | 5' CTCGCCTCATACTCTCCTTC 3' | (SEQ ID NO: 225) | |
| DRGI | 5' GCCTCCCTTGTCCTTCTTCT 3' | (SEQ ID NO: 226) | NM 004147.3 |
| | 5' CCTCCCTTGTCCTTCTTCTT 3' | (SEQ ID NO: 227) | |
| | 5' CTCCACCACCACCACCCTTT 3' | (SEQ ID NO: 228) | |
| | 5' CCTCCCTTGTCCTTCTTCT 3' | (SEQ ID NO: 229) | |
| | 5' GCCTCCCTTGTCCTTCTTCTT 3' | (SEQ ID NO: 230) | |
| EHD1 | 5' TCTTCACTTCTCTTCCCACA 3' | (SEQ ID NO: 231) | NM 006795.2 |
| | 5' GTCTTCACTTCTCTTCCCACA 3' | (SEQ ID NO: 232) | |
| | 5' CTTCACTTCTCTTCCCACA 3' | (SEQ ID NO: 233) | |
| E1F3B | 5' TCCTCTTCCCAGTCGTCCAC 3' | (SEQ ID NO: 234) | NM 001037283.1 |
| | 5' GTCCTCTTCCCAGTCGTC 3' | (SEQ ID NO: 235) | |
| | 5' TCTCCTCTTCCCAGTCGTCC 3' | (SEQ ID NO: 236) | |
| | 5' TCTCCTCTTCCCAGTCGTCCA 3' | (SEQ ID NO: 237) | |
| | 5' CTCCTCTTCCCAGTCGTCCA 3' | (SEQ ID NO: 238) | |
| FGL1 | 5' ATACCACCACCCATGCCAG 3' | (SEQ ID NO: 239) | NM 004467.3 |
| | 5' GAATACCACCACCCATGCCAG 3' | (SEQ ID NO: 240) | |
| | 5' AGTCCATCCTCCTCCATCGG 3' | (SEQ ID NO: 241) | |
| | 5' GAATACCACCACCCATGCCA 3' | (SEQ ID NO: 242) | |
| | 5' GTCATGATCTCTGTCCCACGT 3' | (SEQ ID NO: 243) | |
| FNDC1 | 5' TCACCATCCTTCCCGCCCTT 3' | (SEQ ID NO: 244) | NM 032532.2 |
| | 5' GTTTCCCATTGTCCTCCGTGT 3' | (SEQ ID NO: 245) | |
| | 5' TCCCATTGTCCTCCGTGTTCT 3' | (SEQ ID NO: 246) | |
| | 5' TCCCATTGTCCTCCGTGTTC 3' | (SEQ ID NO: 247) | |
| | 5' TTCCCATTGTCCTCCGTGTTC 3' | (SEQ ID NO: 248) | |
| HIST1H2B1 | 5' CCATCCTTCTTCTGTGCCT 3' | (SEQ ID NO: 249) | NM 003525.2 |
| | 5' GCCATCCTTCTTCTGTGCCT 3' | (SEQ ID NO: 250) | |
| | 5' GCCATCCTTCTTCTGTGCCTT 3' | (SEQ ID NO: 251) | |
| | 5' CCATCCTTCTTCTGTGCCTT 3' | (SEQ ID NO: 252) | |
| | 5' TGCCATCCTTCTTCTGTGCCT 3' | (SEQ ID NO: 253) | |
| HNRNPH1 | 5' ATCCCTCTCCACCTTCCGT 3' | (SEQ ID NO: 254) | NM 005520.2 |
| | 5' CCACGAATCCCTCTCCACCT 3' | (SEQ ID NO: 255) | |
| | 5' ACCACGAATCCCTCTCCACCT 3' | (SEQ ID NO: 256) | |
| | 5' AATCCCTCTCCACCTTCCG 3' | (SEQ ID NO: 257) | |
| | 5' CCACGAATCCCTCTCCACCTT 3' | (SEQ ID NO: 258) | |
| LGALS3 | 5' CTGTCTTTCTTCCCTTCCC 3' | (SEQ ID NO: 259) | NM 002306.3 |
| | 5' ACTGTCTTTCTTCCCTTCCC 3' | (SEQ ID NO: 260) | |
| | 5' GGTAGACTCCAGGTGCAGGT 3' | (SEQ ID NO: 261) | |
| | 5' GACTGTCTTTCTTCCCTTCCC 3' | (SEQ ID NO: 262) | |
| | 5' GACTCTCCTGTTGTTCTCAT 3' | (SEQ ID NO: 263) | |
| LGALS3BP | 5' GGCATCAGTCAGGTCCCACA 3' | (SEQ ID NO: 264) | NM 005567.3 |
| | 5' TCTTCTCCACCAAGCCCTCC 3' | (SEQ ID NO: 265) | |
| | 5' TCTTCTCCACCAAGCCCTCA 3' | (SEQ ID NO: 266) | |
| | 5' CTTCTCCACCAAGCCCTCCA 3' | (SEQ ID NO: 267) | |
| | 5' CAAGCCCTCCACCTCCTCAT 3' | (SEQ ID NO: 268) | |
| LOC645960 | 5' TTCCGTTTGGTCCTCCTCCC 3' | (SEQ ID NO: 269) | XM 002342818.1 |
| | 5' TTTCCGTTTGGTCCTCCTCCC 3' | (SEQ ID NO: 270) | |
| | 5' GTTTCCGTTTGGTCCTCCTCC 3' | (SEQ ID NO: 271) | |
| | 5' GGTTTCCGTTTGGTCCTCCTC 3' | (SEQ ID NO: 272) | |
| | 5' GGTTTCCGTTTGGTCCTCC 3' | (SEQ ID NO: 273) | |

TABLE 4-continued

ANTISENSE RNA

| HUGO Gene Name | Antisense | Human Genbank RNA accession number |
|---|---|---|
| M1R1304 | 5' GGGTTCGAGGCTACAGTGAGA 3' (SEQ ID NO: 274)<br>5' CCGCTGGGCTCAAGTGTTT 3' (SEQ ID NO: 275)<br>5' GGGTTCGAGGCTACAGTGAG 3' (SEQ ID NO: 276)<br>5' GTGGCAGGATCACATCTCACT 3' (SEQ ID NO: 277)<br>5' GGGTTCGAGGCTACAGTGA 3' (SEQ ID NO: 278) | NR 031639.1 |
| M1R192 | 5' CTGGCTGTCAATTCATAGGTC 3' (SEQ ID NO: 279)<br>5' GTCAATTCATAGGTCAGAGC 3' (SEQ ID NO: 280)<br>5' TGTCAATTCATAGGTCAGAGC 3' (SEQ ID NO: 281)<br>5' GGCTGTCAATTCATAGGTCAG 3' (SEQ ID NO: 282)<br>5' GGCTGTCAATTCATAGGTCA 3' (SEQ ID NO: 283) | NR 029578.1 |
| M1R194-2 | 5' CCACATGGAGTTGCTGTTACA 3' (SEQ ID NO: 284)<br>5' CCACATGGAGTTGCTGTTAC 3' (SEQ ID NO: 285)<br>5' GGGCACTTCCACATGGAGTT 3' (SEQ ID NO: 286)<br>5' GGGCACTTCCACATGGAGT 3' (SEQ ID NO: 287)<br>5' TGGGCACTTCCACATGGAGTT 3' (SEQ ID NO: 288) | NR 029829.1 |
| N4BP2L2 | 5' GCTCCTACCCACCACTCTAT 3' (SEQ ID NO: 289)<br>5' GCTCCTACCCACCACTCTA 3' (SEQ ID NO: 290)<br>5' GTGCCTCATTCCTCCCTTCA 3' (SEQ ID NO: 291)<br>5' GCTCCTACCCACCACTCTATT 3' (SEQ ID NO: 292)<br>5' CTCCTACCCACCACTCTATT 3' (SEQ ID NO: 293) | NM 014887.2 |
| PL1N2 | 5' GGTCTCCTGGCTGCTCTTGT 3' (SEQ ID NO: 294)<br>5' GTCTCCTGGCTGCTCTTGTC 3' (SEQ ID NO: 295)<br>5' TCTCCTGGCTGCTCTTGTCC 3' (SEQ ID NO: 296)<br>5' AGCTGCATCATCCGACTCCC 3' (SEQ ID NO: 297)<br>5' GCTGCTCTTGTCCATCTCTGC 3' (SEQ ID NO: 298) | NM 001122.2 |
| POU3F3 | 5' CCTCCTCCAGCCACTTGTTC 3' (SEQ ID NO: 299)<br>5' CCTCCTCCAGCCACTTGTTCA 3' (SEQ ID NO: 300)<br>5' GCCTCCTCCAGCCACTTGTT 3' (SEQ ID NO: 301)<br>5' CCTCCTCCAGCCACTTGTT 3' (SEQ ID NO: 302)<br>5' CTCCTCCAGCCACTTGTTCA 3' (SEQ ID NO: 303) | NM 006236.1 |
| PRR15L | 5' CACTCTCTCCATTCCCTGCCA 3' (SEQ ID NO: 304)<br>5' ACTCTCTCCATTCCCTGCCA 3' (SEQ ID NO: 305)<br>5' TCACTCTCTCCATTCCCTGCC 3' (SEQ ID NO: 306)<br>5' ACTCTCTCCATTCCCTGCAT 3' (SEQ ID NO: 307)<br>5' CACTCTCTCCATTCCCTGCC 3' (SEQ ID NO: 308) | NM 024320.2 |
| PVRL3 | 5' AACATACCACTCCCTCCTG 3' (SEQ ID NO: 309)<br>5' GTCCATCCAACCTGCTCCACA 3' (SEQ ID NO: 310)<br>5' GTCCATCCAACCTGCTCCAC 3' (SEQ ID NO: 311)<br>5' TGTCCATCCAACCTGCTCCAC 3' (SEQ ID NO: 312)<br>5' AAACATACCACTCCCTCCT 3' (SEQ ID NO: 313) | NM 015480.1 |
| RAB3B | 5' CTTTCCTTCCTTCTCTCCCAC 3' (SEQ ID NO: 314)<br>5' TTCCTTCCTTCTCTCCCACA 3' (SEQ ID NO: 315)<br>5' TCCTTCCTTCTCTCCCACA 3' (SEQ ID NO: 316)<br>5' TCCTTTCCTTCCTTCTCTCCC 3' (SEQ ID NO: 317)<br>5' TTTCCTTCCTTCTCTCCCAC 3' (SEQ ID NO: 318) | NM 002867.3 |
| RPS15A | 5' TCCCAGCTCTGTGGTCATCA 3' (SEQ ID NO: 319)<br>5' TTCCCAGCTCTGTGGTCATCA 3' (SEQ ID NO: 320)<br>5' TCGTCTTGCTTCTTCATGGTC 3' (SEQ ID NO: 321)<br>5' TTCCCAGCTCTGTGGTCATC 3' (SEQ ID NO: 322)<br>5' TCCCAGCTCTGTGGTCATC 3' (SEQ ID NO: 323) | NM 001019.4 |
| RSPH3 | 5' TCCTAGCCTCCCGTTGTCTCT 3' (SEQ ID NO: 324)<br>5' CCTCTTCCTAGCCTCCCGTT 3' (SEQ ID NO: 325)<br>5' CCTAGCCTCCCGTTGTCTCT 3' (SEQ ID NO: 326)<br>5' CTCTTCCTAGCCTCCCGTTGT 3' (SEQ ID NO: 327)<br>5' TCCTAGCCTCCCGTTGTCTC 3' (SEQ ID NO: 328) | NM 031924.4 |
| SC5DL | 5' GCTTTCCCTCTGTCATCTCCT 3' (SEQ ID NO: 329)<br>5' GCTTTCCCTCTGTCATCTCC 3' (SEQ ID NO: 330)<br>5' CGCTTTCCCTCTGTCATCTCC 3' (SEQ ID NO: 331)<br>5' CCGCCAATCCTATCCCACA 3' (SEQ ID NO: 332)<br>5' GCCGCCAATCCTATCCCACA 3' (SEQ ID NO: 333) | NM 001024956.2 |

TABLE 4-continued

ANTISENSE RNA

| HUGO Gene Name | Antisense | | Human Genbank RNA accession number |
|---|---|---|---|
| SEC31A | 5' CCATCTGTGCTTCCTCCCA 3' | (SEQ ID NO: 334) | NM 001077207.2 |
| | 5' CCATCTGTGCTTCCTCCCAT 3' | (SEQ ID NO: 335) | |
| | 5' ACCATCTGTGCTTCCTCCCA 3' | (SEQ ID NO: 336) | |
| | 5' CCATCTGTGCTTCCTCCCATG 3' | (SEQ ID NO: 337) | |
| | 5' ACCATCTGTGCTTCCTCCC 3' | (SEQ ID NO: 338) | |
| SLCO2B1 | 5' CTTCTGTCTCTCCCTTGCCCT 3' | (SEQ ID NO: 339) | NM 007256.3 |
| | 5' TCCTTCTGTCTCTCCCTTGCC 3' | (SEQ ID NO: 340) | |
| | 5' CTCCTTCTGTCTCTCCCTTG 3' | (SEQ ID NO: 341) | |
| | 5' CTTCTGTCTCTCCCTTGCCC 3' | (SEQ ID NO: 342) | |
| | 5' CCTTCTGTCTCTCCCTTGCC 3' | (SEQ ID NO: 343) | |
| SNORA25 | 5' GCCCTCTTTGAAATGACCC 3' | (SEQ ID NO: 344) | NR 003028.1 |
| | 5' AGCCCTCTTTGAAATGACCC 3' | (SEQ ID NO: 345) | |
| | 5' CTGGGTTTCACAGCCTCAT 3' | (SEQ ID NO: 346) | |
| | 5' CTCTGGGTTTCACAGCCTCA 3' | (SEQ ID NO: 347) | |
| | 5' CTGGGTTTCACAGCCTCATA 3' | (SEQ ID NO: 348) | |
| SNORD17 | 5' GTCCCTGCTGACACCAACCA 3' | (SEQ ID NO: 349) | NR 003045.1 |
| | 5' GTCCCTGCTGACACCAACCAT 3' | (SEQ ID NO: 350) | |
| | 5' TCCCTGCTGACACCAACCAT 3' | (SEQ ID NO: 351) | |
| | 5' TCCCTGCTGACACCAACCA 3' | (SEQ ID NO: 352) | |
| | 5' TCCCTGCTGACACCAACCATT 3' | (SEQ ID NO: 353) | |
| SNX5 | 5' GCTGCCACTCTCTTCCGTTT 3' | (SEQ ID NO: 354) | NM 014426.2 |
| | 5' GCTGCCACTCTCTTCCGTT 3' | (SEQ ID NO: 355) | |
| | 5' GCTGCCACTCTCTTCCGTTTG 3' | (SEQ ID NO: 356) | |
| | 5' TGCTGCCACTCTCTTCCGTT 3' | (SEQ ID NO: 357) | |
| | 5' TGCTGCCACTCTCTTCCGT 3' | (SEQ ID NO: 358) | |
| TM4SF1 | 5' CACCACTCTCAGCCCATTCC 3' | (SEQ ID NO: 359) | NM 014220.2 |
| | 5' ACACCACTCTCAGCCCATTCC 3' | (SEQ ID NO: 360) | |
| | 5' CACCACTCTCAGCCCATTCCT 3' | (SEQ ID NO: 361) | |
| | 5' ACCACTCTCAGCCCATTCCT 3' | (SEQ ID NO: 362) | |
| | 5' ACCACTCTCAGCCCATTCC 3' | (SEQ ID NO: 363) | |
| TTR | 5' TCCCATCCCTCGTCCTTCAG 3' | (SEQ ID NO: 364) | NM 000371.3 |
| | 5' TCCCATCCCTCGTCCTTCA 3' | (SEQ ID NO: 365) | |
| | 5' ATCCCATCCCTCGTCCTTCA 3' | (SEQ ID NO: 366) | |
| | 5' ATTCCCATCCCTCGTCCTTCAG 3' | (SEQ ID NO: 367) | |
| | 5' ATCCCATCCCTCGTCCTTC 3' | (SEQ ID NO: 368) | |

LNAs

Also disclosed herein are LNAs corresponding to the genes of Table 1. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. Such oligomers are commercially available, and one of skill in the art would understand how to design them. The locked ribose conformation enhances base stacking and backbone pre-organization. This significantly increases the hybridization properties (melting temperature) of oligonucleotides. (Kaur, H; Arora, A; Wengel, J; Maiti, S; Arora, A.; Wengel, J.; Maiti, S. (2006). "Thermodynamic, Counterion, and Hydration Effects for the Incorporation of Locked Nucleic Acid Nucleotides into DNA Duplexes". Biochemistry 45 (23): 7347-55.)

LNA nucleotides are used to increase the sensitivity and specificity of expression in DNA microarrays. FISH probes, real-time PCR probes and other molecular biology techniques based on oligonucleotides. For the in situ detection of miRNA the use of LNA is an efficient method. A triplet of LNA nucleotides surrounding a single-base mismatch site maximizes LNA probe specificity unless the probe contains the guanine base of G-T mismatch.

Morpholinos

Morpholinos are synthetic antisense oligos that can block access of other molecules to small (about 25 base) regions of ribonucleic acid (RNA). Morpholinos are often used to determine gene function using reverse genetics methods by blocking access to mRNA. Morpholinos, usually about 25 bases in length, bind to complementary sequences of RNA by standard nucleic acid base-pairing. Morpholinos do not degrade their target RNA molecules. Instead, Morpholinos act by "steric hindrance", binding to a target sequence within an RNA and simply interfering with molecules which might otherwise interact with the RNA. Morpholinos have been used in mammals, ranging from mice to humans.

Bound to the 5'-untranslated region of messenger RNA (mRNA), Morpholinos can interfere with progression of the ribosomal initiation complex from the 5' cap to the start codon. This prevents translation of the coding region of the targeted transcript (called "knocking down" gene expression). Morpholinos can also interfere with pre-mRNA processing steps, usually by preventing the splice-directing snRNP complexes from binding to their targets at the borders of introns on a strand of pre-RNA. Preventing U1 (at the donor site) or U2/U5 (at the polypyrimidine moiety & acceptor site) from binding can cause modified splicing, commonly leading to exclusions of exons from the mature mRNA. Targeting some splice targets results in intron inclusions, while activation of cryptic splice sites can lead to partial inclusions or exclusions. Targets of U11/U12 snRNPs can also be blocked. Splice modification can be conveniently assayed by reverse-transcriptase polymerase chain reaction (RT-PCR) and is seen as a band shift after gel electrophoresis of RT-PCR products. Methods of designing, making and utilizing morpholinos are disclosed in U.S. Pat. No. 6,867,349, which is incorporated herein by reference in its entirety.

Small Molecules

Any small molecule that inhibits activity of a gene or a gene product, e.g. an RNA or protein, set forth in Table 1 can be utilized in the methods of the present invention to decrease infection. Examples of such small molecules can be found in Example 3. Small molecules can be found in the scientific literature, in the StarLite/CHEMBL database available from the European Bioinformatics Institute, in DrugBank (Wishart et al. *Nucleic Acids Res.* 2006 Jan. 1; 34 (Database issue):D668-72), package inserts, brochures, chemical suppliers (for example, Sigma, Tocris, Aurora Fine Chemicals, to name a few), or by any other means, such that one of skill in the art makes the association between a gene product of Table 1 and inhibition of this gene product by a molecule. Preferred small molecules are those small molecules that have $IC_{50}$ values of less than about 1 mM, less than about 100 micromolar, less than about 75 micromolar, less than about 50 micromolar, less than about 25 micromolar, less than about 10 micromolar, less than about 5 micromolar or less than about 1 micromolar. The half maximal inhibitory concentration ($IC_{50}$) is a measure of the effectiveness of a compound in inhibiting biological or biochemical function. This quantitative measure indicates how much of a particular compound or other substance (inhibitor) is needed to inhibit a given biological process (or component of a process, i.e. an enzyme, cell, cell receptor or microorganism) by half. In other words, it is the half maximal (50%) inhibitory concentration (1C) of a substance (50% 1C, or $1C_{50}$). It is commonly used as a measure of antagonist drug potency in pharmacological research.

Sometimes, it is also converted to the $pIC_{50}$ scale ($-\log 1C_{50}$), in which higher values indicate exponentially greater potency. According to the FDA, $1C_{50}$ represents the concentration of a drug that is required for 50% inhibition in vitro. It is comparable to an $EC_{50}$ for agonist drugs. $EC_{50}$ also represents the plasma concentration required for obtaining 50% of a maximum effect in vivo.

The present invention also provides the synthesis of small molecules that inhibit activity of a gene product set forth in Table 1. The present invention describes gene products for which three-dimensional structures are well known and can be obtained from the RCSB Protein Databank http://www.rcsb.org/pdb/home/home.do or http://www.rcsb.org for available three-dimensional structures. For each protein set forth above, unique identifiers from the RCSB Protein Database and the resolution of the crystal structure in angstroms are provided in brackets. The structures and coordinates provided under the unique RCSB identifiers are hereby incorporated in their entireties by this reference. All of the structural information about the gene products set forth herein, for example, crystal structures and their corresponding coordinates, are readily available to one of skill in the art from the references cited herein, from the RCSB Protein Databank or elsewhere in the scientific literature.

Crystal structures can also be generated. Alternatively, one of skill in the art can obtain crystal structures for proteins, or domains of proteins, that are homologous to the proteins set forth in Table 1 from the RCSB Protein Databank or elsewhere in the scientific literature for use in homology modeling studies.

Routine high throughput in silico or in vitro screening of compound libraries for the identification of small molecules is also provided by the present invention. Compound libraries are commercially available. With an available crystal structure, it is routine for one of skill in the art to screen a library in silico and identify compounds with desirable properties, for example, binding affinity. For example, one of skill in the art can utilize the crystal structure(s) of Havcr1 in a computer program to identify compounds that bind to a site on the crystal structure with a desirable binding affinity. This can be performed in an analogous way for any protein set forth herein to identify compounds that bind with a desirable binding affinity. Numerous computer programs are available and suitable for rational drug design and the processes of computer modeling, model building, and computationally identifying, selecting and evaluating potential compounds. These include, for example, SYBYL (available from TRIPOS, St. Louis Mo.), DOCK (available from University of California, San Francisco), GRID (available from Oxford University, UK), MCSS (available from Molecular Simulations Inc., Burlington, Mass.), AUTODOCK (available from Oxford Molecular Group), FLEX X (available from TRIPOS, St. Louis Mo.), CAVEAT (available from University of California, Berkeley), HOOK (available from Molecular Simulations Inc., Burlington, Mass.), and 3-D database systems such as MACCS-3D (available from MDL Information Systems, San Leandro, Calif.), UNITY (available from TRIPOS, St. Louis Mo.), and CATALYST (available from Molecular Simulations Inc. Burlington, Mass.). Compounds can also be computationally modified using such software packages as LUDI (available from Biosym TechMA), and LEAPFROG (TRIPOS Associates, St. Louis, Mo.). These computer-modeling techniques can be performed on any suitable hardware including tor example, workstations available from Silicon Graphics, Sun Microsystems, and the like. These techniques, methods, hardware and software packages are representative and are not intended to be comprehensive listing. Other modeling techniques known in the art can also be employed in accordance with this invention.

A filter can be applied to the results to yield one or more compounds with a binding affinity in a particular range, for example, and not to be limiting, from about 100 micromolar to about 100 nanomolar, from about 10 micromolar to about 10 nanomolar, from about 1 micromolar to about 1 nanomolar, or from about 0.5 micromolar to about 0.5 nanomolar. Another filter can provide compounds with a certain binding affinity and size, for example, less than 1000 daltons, less than 500 daltons, less than 400 daltons, less than 300 daltons, less than 200 daltons, less than 100 daltons or less than 50 daltons or any size in between. The ranges and properties can be modified depending on the protein being studied. The compounds identified via this screening method can be further studied in silico, in vitro or in vivo. For example, the compounds can be modified in silico and rescreened in silico to determine the effects of chemical modifications on binding affinity or other properties being assessed in silico. The compounds identified in silico can be synthesized for in vitro or in vivo analysis.

All of the screening leading up to in vivo testing can be done in silico or in combination with in vitro assays. The initial compounds identified in silico and the resulting modified compounds can be screened in vitro, for example, in cellular assays to determine the effect of the compound on the cellular host protein as well as in viral assays, to determine antiviral activity. $IC_{50}$ values can be obtained from the cellular assays, which may or may not be similar to the concentration necessary to effect 50% inhibition of viral infection in a viral assay. However, although not required, it is desirable to have a compound that has an $IC_{50}$ value of less than about 1 mM, less than about 100 micromolar, less than about 75 micromolar, less than about 50 micromolar, less than about 25 micromolar, less than about 10 micromolar, less than about 5 micromolar or less than about 1 micromolar. Similarly, although not required, it is desirable to have a compound that effects 50% inhibition of viral infection at a concentration of less than about 1 mM, less than about 100 micromolar, less than about 75 micromolar, less than about 50 micromolar, less than about 25 micromolar, less than about 10 micromolar, less than about 5 micromolar or less than about 1 micromolar or any concentration in between.

Further modifications of the compounds can be done after in vitro screening, either in silico or via chemical synthesis, for further evaluation, prior to additional in vitro screening or in vivo studies. It is understood that this process can be iterative, involving a combination of in silico and wet chemistry techniques, but routine in drug development.

Other filters can be applied to the in silico screening process, for example, a filter that takes ADMET (adsorption, distribution, metabolism, excretion, toxicity) properties into consideration can be applied. ADMET modeling can be used during compound optimization to define an acceptable property space that contains compounds likely to have the desired properties. These filters can be applied sequentially or simultaneously depending.

Libraries for virtual or in vitro screening are available for the skilled artisan, for example from ChemBridge Corporation (San Diego, Calif.), such as a GPCR library, a kinase targeted library (KINACore), or an ion channel library (Ion Channel Set), to name a few. Compound libraries can also be obtained from the National Institutes of Health. For example, the NIH Clinical Collection of compounds that have been used in clinical trials can also be screened. Biofocus DPI (Essex, United Kingdom) also maintains and designs compound libraries that can be purchased for screening. One of skill in the art can select a library based on the protein of interest. For example, a kinase library can be screened to identify a compound that binds to and/or modulates a kinase. Other libraries that target enzyme families, for example, ATPases, hydrolases, isomerases, polymerases, transferases, phosphatases, etc., can also be screened, depending on the type of enzyme.

Compound libraries can also be screened in order to identify a compound that disrupts or inhibits specific interactions, for example, the interaction of E1F5 with E1F2. See, for example, Singh et al, *The EMBO Journal* 2006 September; 25:4537-46. Compounds can be administered to cells comprising both E1F5 and E1F2 in order to identify compounds that disrupt this interaction and result in decreased interaction between of the two proteins. Co-immunoprecipiation experiments can be utilized. Similarly, FRET analysis can be utilized, to identify compounds that disrupt the interaction between a two proteins.

Additional inhibitors include compositions comprising carbon and hydrogen, and optionally comprising one or more of —S, —N, —O, —Cl, —Br, or —Fl, appropriately bonded as a structure, with a size of less than about 1000 daltons, less than about 500 daltons, less than about 300 daltons, less than about 200 daltons, or less than about 100 daltons, that fits into a binding pocket or an active site of a gene product set forth herein. In particular, inhibitors that have the properties described in Lipinsky's Rule of Five are included herein. Lipinski's rule of five states that a drug/inhibitor has a weight under 500 Daltons, a limited lipophilicity or octanol-water partition coefficient (expressed by Log P<5, with P=[drug]org./[drug]aq.), a maximum of 5 H-bond donors (expressed as the sum of OHs and NHs), and a maximum of 10 H-bond acceptors (expressed as the sum of oxygen and nitrogen atoms). Inhibitors that violate no more than one of the above-listed five rules are also included herein.

Other methods of decreasing expression and/or activity include methods of interrupting or altering transcription of mRNA molecules by site-directed mutagenesis (including mutations caused by a transposon or an insertional vector). Chemical mutagenesis can also be performed in which a cell is contacted with a chemical (for example ENU) that mutagenizes nucleic acids by introducing mutations into a gene set forth in Table 1. Transcription of mRNA molecules can also be decreased by modulating a transcription factor that regulates expression of any of the genes set forth in Table 1. Radiation can also be utilized to effect mutagenesis.

The present invention also provides decreasing expression and/or activity of a gene or a gene product set forth in Table 1 via modulation of other genes and gene products in pathways associated with the targets set forth in Table 1. Pathways include, but are not limited to ubiquitination pathways, trafficking pathways, cell signaling pathways, apoptotic pathways, TNF receptor pathways, GPCR pathways etc. Thus, other genes either upstream or downstream of the genes set forth in Table 1 are also provided herein as targets for inhibition of infection. These examples are merely exemplary as this applies to all of the genes and gene products set forth in Table 1 and the cellular pathways they are involved in.

Galectin-3

The galectins are a family of proteins defined by shared sequence elements and by affinity for β-galactosides (Barondes et al., 1994). There are now ten known mammalian galectins, but biochemical analysis of tissues as well as the accumulation of partial DNA sequences from expressed sequence tags (ESTs) suggest that there are many more (Cooper and Barondes, 1999). Galectins occur at high concentration (usually 0.1% of total soluble cell protein) in a limited range of cell types, different for each galectin. All galectins bind lactose and other β-galactosides, but they differ in their affinity for more complex saccharides (Leffler and Barondes, 1986, Barondes et al., 1994).

Galectin-3 plays an important role in inflammatory diseases. It also interacts with the surface carbohydrates of many pathogens, including LPS. Galectin-3 is a negative regulator of LPS-induced inflammation. Galectin-3 is constitutively produced by macrophages and directly binds to LPS. Galectin-3-deficient macrophages had markedly elevated LPS-induced signaling and inflammatory cytokine production compared with wild-type cells, which was specifically inhibited by the addition of recombinant galectin-3 protein. In contrast, blocking galectin-3 binding sites by using a neutralizing Ab or its ligand, beta-lactose, enhanced LPS-induced inflammatory cytokine expression by wild-type macrophages. In vivo, mice lacking galectin-3 were more susceptible to LPS shock associated with excessive induction of inflammatory cytokines and NO production. However, these changes conferred greater resistance to Salmonella infection. Thus, galectin-3 is a previously unrecognized, naturally occurring, negative regulator of LPS function, which protects the host from endotoxin shock but, conversely, favors Salmonella survival. (Li et al., J. Immunol., 2008 Aug. 15; 181(4):2781-9.) It is herein disclosed that galectin-3 is also involved in C. difficile toxin infection. Therefore, inhibiting galectin-3 can inhibit infection.

Solid phase binding assays and inhibition assays have identified a number of saccharides and glycoconjugates with the ability to bind galectins (reviewed by Leffler, 2001). All galectins bind lactose with Kd of 0.5 to 1 mM. The affinity of D-galactose is 50 to 100 times lower. N-Acetyllactosamine and related disaccharides bind about as well as lactose but for certain galectins up to 10 times better. The best small saccharide ligands for galectin-3 were those carrying blood group A-determinants attached to lactose or lacNAc-residues and were found to bind up to about 50 times better than lactose. Galectin-1 shows no preference for these saccharides.

Larger saccharides of the polylactosamine type have been proposed as preferred ligands for galectins. In solution using polylactosamine carrying glycopeptides, there was evidence for this for galectin-3 but not galectin-1 (Leffler and Barondes, 1986). A modified plant pectin polysaccharide has been reported to bind galectin-3 (Pienta et al., 1995).

A further inhibitor of galectin-3 is found in U.S. Pat. No. 7,230,096, which is hereby incorporated by reference in its entirety for the teaching concerning the compound disclosed therein for inhibiting galectin-3.

Thiodigalactoside is known to be a synthetic inhibitor approximately as efficient as N-acetyllactosamine (Leffler and Barondes, 1986). Saccharides coupled to amino acids with anti-cancer activity were first identified as natural compounds in serum, but subsequently synthetic analogues have been made (Glinsky et al., 1996). Among them, those with lactose or Gal coupled to the amino acid inhibits. Adivalent form of a lactosyl-amino acid had higher potency in a solid phase assay (Naidenko et al., 2000). Starburst dendrimers (Andre et al, 1999) and glycopolymers (Pohl et al, 1999), made polyvalent in lactose-residues, have been described as galectin-3 inhibitors with improved potency as compared to lactose.

Lactose, galactose, and glucose, as well as analogues and derivatives thereof can be used as inhibitors of galectin-3, thereby treating C. difficile toxic infection. A simple and economical procedure for the attachment of reducing sugars to aminated solid supports has been developed. Reaction of the amino groups on the solid support with p-nitrophenyl chloroformate, followed by 1,6-hexanediamine, yields a chain-extended amine to which reducing sugars can be attached while remaining accessible to macromolecules. Immobilization of the reducing sugars involves a simple incubation followed by trapping of the resulting glycosylamine with acetic anhydride and recovery of the unreacted sugar by filtration. This technique was used to immobilize lactose and sialyllactose onto silylaminated Chromosorb P, producing solid supports that effectively neutralized the activity of cholera toxin from *Vibrio cholerae* and heat-labile enterotoxin of enterotoxigenic *Escherichia coli*. The general applicability of such solid supports for toxin neutralization was further demonstrated by immobilization of the enzymatically synthesized αGal(1-3)βGal(1-4)Glc trisaccharide, which produced a support that efficiently neutralized toxin A of *Clostridium difficile*. The results from this study suggest that these solid supports have the potential to serve as inexpensive therapeutics for bacterial toxin-mediated diarrheal diseases. (Nilsson et al., Bioconjugate Chem., 1997, 8(4), pp 466-471).

Pharmaceutical Compositions and Modes of Administration

The present invention provides a method of decreasing the toxicity of a toxin in a subject by decreasing the expression or activity of a gene or gene product set forth in Table 1, said method comprising administering to the subject an effective amount of a composition that decreases the expression or activity of a gene or a gene product set forth in Table 1.

Also provided is a method of decreasing the toxicity of a toxin in a subject comprising administering to the subject an effective amount of a composition that decreases expression or activity of a gene or a gene product set forth in Table 1, wherein the composition inhibits the toxicity of a *Clostridium* toxin, a *staphylococcus* toxin, or a ricin toxin.

Also provided is a method of decreasing the toxicity of a toxin in a subject comprising administering to the subject an effective amount of a composition that decreases expression or activity of a gene or a gene product set forth in Table 1, wherein the composition inhibits the toxicity of a *Clostridium difficile* toxin.

The present invention also provides method of decreasing the toxicity of a toxin in a subject comprising administering to the subject an effective amount of a composition that decreases expression or activity of a gene or a gene product set forth in Table 1, wherein the composition inhibits toxicity by two or more toxins selected from the group consisting of *Clostridium perfringens* toxins, *Clostridium difficile* toxins, *Clostridium botulinum* toxins, *Clostridium tetani* toxins, saxitoxins, tetrodotoxins, abrin, conotoxins, Staphlococcal toxins, *E. coli* toxins, streptococcal toxins, diphtheria toxin, cholera toxin, pertussis toxin, *pseudomonas* toxin, *bacillus* toxin, shigatoxins, T-2 toxins, and anthrax toxins.

As described herein, the genes set forth in Table 1 can be involved in the toxicity of two or more toxins. Therefore, the present invention provides methods of treating or preventing the toxicity of an unspecified toxin in a subject by administering a composition that decreases activity or expression of a gene involved in the toxicity of two or more toxins. More particularly, the present invention provides a method of decreasing the toxicity of an unspecified toxin in a subject comprising: a) diagnosing a subject with toxicity of an unspecified toxin; and b) administering to the subject an effective amount of a composition that decreases expression or activity of a gene or a gene product set forth in Table 1, wherein the composition inhibits the toxicity of two or more toxins selected from the group consisting of *Clasiridium perfringens* toxins, *Clostridium difficile* toxins, *Clostridium botulinum* toxins, *Clostridium tetani* toxins, saxitoxins, tetrodotoxins, abrin, conotoxins, Staphlococcal toxins, *E. coli* toxins, streptococcal toxins, diphtheria toxin, cholera toxin, pertussis toxin, *pseudomonas* toxin, *bacillus* toxin, shigatoxins, T-2 toxins, and anthrax toxins. More specifically, the toxins can be any *Clostridium difficile* toxin.

The present invention also provides a method of preventing or decreasing an unspecified bioterror threat in a subject comprising: a) diagnosing a subject with an unspecified bioterrorist inflicted intoxication; and b) administering to the subject an effective amount of a composition that decreases expression or activity of a gene or a gene product set forth in Table 1, wherein the composition inhibits the toxicity of two or more, three or more, four or more; or five or more toxins selected from the group consisting of a bacterial toxin, neurotoxins, such as botulinum neurotoxins, ricin,

*Clostridium perfringens* toxins, *Clostridium difficile* toxins, *Clostridium tetani* toxins, saxitoxins, tetrodotoxins, abrin, conotoxins, Staphlococcal toxins, *E. coli* toxins, streptococcal toxins, diphtheria toxin, cholera toxin, pertussis toxin, *pseudomonas* toxin, *bacillus* toxin, shigatoxins, T-2 toxins, anthrax toxins, cyanotoxins, hemotoxins, necrotoxins, mycotoxins, such as aflatoxin, amatoxin, citrinin, cytohalasin, ergotamine, fumonisin, gliotoxin, ibotenic acid, muscimol, ochratoxin, patulin, sterigmatocystin, trichothecene, vomitoxin, zearanol, and zearalenone, chimeric forms of the toxins listed herein, and the like.

The present also invention provides a method of decreasing infection by a pathogen in a subject by decreasing the expression or activity of a gene or gene product set forth in Table 1, said method comprising administering to the subject an effective amount of a composition that decreases the expression or activity of a gene or a gene product set forth in Table 1.

Also provided is a method of decreasing infection in a subject comprising administering to the subject an effective amount of a composition that decreases expression or activity of a gene or a gene product set forth in Table 1, wherein the composition inhibits infection by two or more respiratory viruses. Also provided is a method of decreasing infection in a subject comprising administering to the subject an effective amount of a composition that decreases expression or activity of a gene or a gene product set forth in Table 1, wherein the composition inhibits infection by three or more respiratory viruses. Also provided is a method of decreasing infection in a subject comprising administering to the subject an effective amount of a composition that decreases expression or activity of a gene or a gene product set forth in Table 1, wherein the composition inhibits infection by four or more respiratory viruses. Also provided is a method of decreasing infection in a subject comprising administering to the subject an effective amount of a composition that decreases expression or activity of a gene or a gene product set forth in Table 1, wherein the composition inhibits infection by five or more respiratory viruses. These can be selected from the group consisting of: a picornavirus, an orthomyxovirus, a paramyxovirus, a coronavirus and an adenovirus. Since picornaviruses, orthomyxoviruses, paramyxoviruses, coronaviruses and adenoviruses are families of viruses, two or more, three or more, four or more, or five or more respiratory viruses can be from the same or from different families. For example, and not to be limiting, the composition can inhibit infection by two or more orthomyxoviruses; two or more picornaviruses; an orthomyxovirus, an adenovirus, and a picornavirus; an orthomyxovirus, a paramyxovirus and an adenovirus; an orthomyxovirus, two picornaviruses and a paramyxovirus; three orthomyxoviruses, a picornavirus and an adenovirus, etc. More particularly, the composition can inhibit infection by two or more, three or more or four or more respiratory viruses selected from the group consisting of an influenza virus, a parainfluenza virus, an adenovirus, a rhinovirus and an RSV virus.

The present invention also provides a method of decreasing infection in a subject comprising administering to the subject an effective amount of a composition that decreases expression or activity of a gene or a gene product set forth in Table 1, wherein the composition inhibits infection by two or more gastrointestinal viruses. The present invention also provides a method of decreasing infection in a subject comprising administering to the subject an effective amount of a composition that decreases expression or activity of a gene or a gene product set forth in Table 1, wherein the composition inhibits infection by three or more gastrointestinal viruses. The present invention also provides a method of decreasing infection in a subject comprising administering to the subject an effective amount of a composition that decreases expression or activity of a gene or a gene product set forth in Table 1, wherein the composition inhibits infection by four or more gastrointestinal viruses. The present invention also provides a method of decreasing infection in a subject comprising administering to the subject an effective amount of a composition that decreases expression or activity of a gene or a gene product set forth in Table 1, wherein the composition inhibits infection by five or more gastrointestinal viruses. These viruses can be selected from the group consisting of: a filovirus, a picornavirus, a calcivirus, a flavivirus or a reovirus. Since filoviruses, picornaviruses, calciviruses, flaviviruses and reoviruses are families of viruses, the composition can inhibit infection by two or more, three or more, four or more, or five or more gastrointestinal viruses from the same or from different families. More particularly, the composition can inhibit infection by two or more, three or more, four or more, or five or more gastrointestinal viruses selected from the group consisting of a reovirus, a Norwalk virus, an Ebola virus, a Marburg virus, a Dengue fever virus, a West Nile virus, a yellow fever virus, a rotavirus and an enterovirus.

The present invention also provides a method of decreasing infection in a subject comprising administering to the subject an effective amount of a composition that decreases expression or activity of a gene or a gene product set forth in Table 1, wherein the composition inhibits infection by one or more pathogens selected from the group consisting of: a picornavirus, an orthomyxovirus, a paramyxovirus, a coronavirus, an adenovirus, and inhibits infection by one or more pathogens selected from the group consisting of: a flavivirus, a filovirus, a calcivirus or a reovirus.

The present invention also provides a method of decreasing infection in a subject comprising administering to the subject an effective amount of a composition that decreases expression or activity of a gene or a gene product set forth in Table 1, wherein the composition inhibits infection by two or more pathogens selected from the group consisting of HIV virus, a pox virus, a herpes virus, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus.

The present invention also provides a method of decreasing infection in a subject comprising administering to the subject an effective amount of a composition that decreases expression or activity of a gene or a gene product set forth in Table 1 wherein the composition inhibits infection by two or more pathogens selected from the group consisting of: influenza, a pox virus, LCM, Junin virus, Machupo virus, Guanarito virus, Lassa Fever virus, hantavirus, Rift Valley Fever virus, Ebola virus, Marburg virus or Dengue Fever virus.

The present invention also provides a method of decreasing infection in a subject comprising administering to the subject an effective amount of a composition that decreases expression or activity of a gene or a gene product set forth in Table 1, wherein the composition inhibits infection by three or more pathogens. The three or more pathogens can be selected from the viruses, bacteria, parasites and fungi set forth herein. More particularly, the three or more pathogens can be selected from the group consisting of: an HIV virus, a pox virus, a herpes virus, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus.

The present invention also provides a method of decreasing infection in a subject comprising administering to the subject an effective amount of a composition that decreases expression or activity of a gene or a gene product set forth in Table 1, wherein the composition inhibits infection by four or more pathogens. The four or more pathogens can be selected from the viruses, bacteria, parasites and fungi set forth herein. More particularly, the four or more pathogens can be selected from the group consisting of: a pox virus, BVDV, a herpes virus, HIV, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus.

The present invention also provides a method of decreasing infection in a subject comprising administering to the subject an effective amount of a composition that decreases expression or activity of a gene or a gene product set forth in Table 1, wherein the composition inhibits infection by five or more pathogens. The five or more pathogens can be selected from the viruses, bacteria, parasites and fungi set forth herein. More particularly, the five or more pathogens can be selected from the group consisting of: a pox virus, BVDV, a herpes virus, HIV, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus.

The present invention also provides a method of decreasing infection in a subject comprising administering to the subject an effective amount of a composition that decreases expression or activity of a gene or a gene product set forth in Table 1, wherein the composition inhibits infection by six or more pathogens. The six or more pathogens can be selected from the viruses, bacteria, parasites and fungi set forth herein. More particularly, the six or more pathogens can be selected from the group consisting of: a pox virus, BVDV, a herpes virus, HIV, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus; Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus.

The present invention also provides a method of decreasing the toxicity of a toxin in a subject and decreasing infection in a subject comprising administering to the subject an effective amount of a composition that decreases expression or activity of a gene or a gene product set forth in Table 1, wherein the composition inhibits the toxicity of a *Clostridium perfringens* toxin, *Clostridium difficile* toxin, *Clostridium botulinum* toxin, *Clostridium tetani* toxin, saxitoxin, tetrodotoxin, abrin, conotoxin, Staphlococcal toxin, *E. coli* toxin, streptococcal toxin, diphtheria toxin, cholera toxin, pertussis toxin, *pseudomonas* toxin, *bacillus* toxin, shigatoxin, T-2 toxin, or an anthrax toxin and inhibits the infection of a pox virus, BVDV, a herpes virus, HIV, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus.

The present invention also provides a method of decreasing infection in a subject comprising administering to the subject an effective amount of a composition that decreases expression or activity of a gene or a gene product set forth in Table 1, wherein the composition inhibits co-infection by HIV and one or more viruses, bacteria, parasites or fungi. For example, decreasing co-infection of HIV and any of the viruses, including for example any families, genus, species, or group of viruses. As a further example, co-infection of HIV and a respiratory virus is provided herein. Respiratory viruses include picornaviruses, orthomyxoviruses, paramyxoviruses, coronaviruses, and adenoviruses. More specifically, the respiratory virus can be any strain of influenza, rhinovirus, adenovirus, parainfluenza virus or RSV. Also provided is decreasing co-infection of HIV and a gastrointestinal virus. Gastrointestinal viruses include picornaviruses, filoviruses, flaviviruses, calciviruses and reoviruses. More specifically, and not to be limiting, the gastrointestinal virus can be any strain of reovirus, a Norwalk virus, an Ebola virus, a Marburg virus, a rotavirus, an enterovirus, a Dengue fever virus, a yellow fever virus, or a West Nile virus. Further provided is a method of decreasing co-infection of HIV with a pox virus, LCM, Junin virus, Machupo virus, Guanarito virus, Lassa Fever virus, hantavirus, Rift Valley Fever virus Ebola virus, Marburg virus or Dengue Fever virus. More particularly, decreasing co-infection of HIV and a hepatitis virus, such as Hepatitis A, Hepatitis B or Hepatitis C is provided. Also provided is decreasing co-infection of HIV and a herpes virus, for example, HSV-1 or HSV-2. In addition decreasing co-infection of HIV and tuberculosis is also provided. Further provided is decreasing co-infection of HIV and CMV, as well as decreasing co-infection of HIV and HPV.

As described herein, the genes set forth in Table 1 can be involved in the pathogenesis of two or more respiratory viruses. Therefore, the present invention provides methods of treating or preventing an unspecified respiratory infection in a subject by administering a composition that decreases activity or expression of a gene involved in the pathogenesis of two or more respiratory viruses. More particularly, the present invention provides a method of decreasing an unspecified respiratory infection in a subject comprising: a) diagnosing a subject with an unspecified respiratory infection; and b) administering to the subject an effective amount of a composition that decreases expression or activity of a gene or a gene product set forth in Table 1, wherein the composition inhibits infection by two or more respiratory viruses selected from the group consisting of picornaviruses, orthomyxoviruses, paramyxoviruses, coronaviruses, or adenoviruses. As set forth above, in the methods of the present invention, the two or more respiratory viruses can be from the same family or from a different family of respiratory viruses. More specifically, the respiratory virus can be any strain of influenza, rhinovirus, adenovirus, parainfluenza virus or RSV. In this method, the composition can be a composition that inhibits infection by three or more, four or more, five or more; or six or more respiratory viruses selected from the group consisting of a picornaviruses, an orthomyxoviruses, paramyxoviruses, corona viruses, or adenoviruses.

As described herein, the genes set forth in Tables I can be involved in the pathogenesis of two or more gastrointestinal viruses. Therefore, the present invention provides methods of treating or preventing an unspecified gastrointestinal infection in a subject by administering a composition that decreases activity or expression of a gene involved in the pathogenesis of two or more gastrointestinal viruses. More particularly, the present invention provides a method of decreasing an unspecified gastrointestinal infection in a subject comprising: a) diagnosing a subject with an unspecified gastrointestinal infection; and b) administering to the subject an effective amount of a composition that decreases expression or activity of a gene or a gene product set forth in Table 1, wherein the composition inhibits infection by two or more gastrointestinal viruses selected from the group consisting of a flavivirus, a filovirus, a calcivirus or a reovirus. As set forth above, in the methods of the present invention, the two or more gastrointestinal viruses can be from the same family or from a different family of gastrointestinal viruses. More particularly, and not to be limiting, the gastrointestinal virus can be any strain of reovirus, a Norwalk virus, an Ebola virus, a Marburg virus, a rotavirus, an enterovirus, a Dengue fever virus, a yellow fever virus, or a West Nile virus. In this method, the composition can be a composition that inhibits infection by three or more, four or more, five or more; or six or more gastrointestinal viruses selected from the group consisting of a flavivirus, a filovirus, a calcivirus or a reovirus.

The present invention also provides a method of preventing or decreasing an unspecified pandemic or bioterror threat in a subject comprising: a) diagnosing a subject with an unspecified pandemic or bioterrorist inflicted infection; and b) administering to the subject an effective amount of a composition that decreases expression or activity of a gene or a gene product set forth in Table 1, wherein the composition inhibits infection by two or more, three or more, four or more; or five or more viruses selected from the group consisting of a pox virus, an influenza virus, West Nile virus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus and a Dengue fever virus.

The present invention also provides a method of preventing or decreasing an unspecified pandemic or bioterror threat in a subject comprising: a) diagnosing a subject with an unspecified pandemic or bioterrorist inflicted intoxication and infection; and b) administering to the subject an effective amount of a composition that decreases expression or activity of a gene or a gene product set forth in Table 1, wherein the composition inhibits the toxicity of two or more, three or more, four or more; or five or more toxins selected from the group consisting of a bacterial toxin, neurotoxins, such as botulinum neurotoxins, ricin, *Clostridium perfringens* toxins, *Clostridium difficile* toxins, *Clostridium tetani* toxins, saxitoxins, tetrodotoxins, abrin, conotoxins, Staphlococcal toxins, *E. coli* toxins, streptococcal toxins, diphtheria toxin, cholera toxin, pertussis toxin, *pseudomonas* toxin, *bacillus* toxin, shigatoxins, T-2 toxins, and anthrax toxins, and wherein the composition inhibits infection by two or more, three or more, four or more; or five or more viruses selected from the group consisting of a pox virus, an influenza virus. West Nile virus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus and a Dengue fever virus.

Also provided by the present invention is a method of managing secondary infections in a patient comprising administering to the subject an effective amount of a composition that decreases expression or activity of a gene or a gene product set forth in Table 1, wherein the composition can inhibit infection by HIV and one or more, two or more, three or more, four or more; or five or more secondary infections.

As set forth above, the genes set forth in Table 1 can be involved in the pathogenesis of three or more pathogens. Therefore, the present invention provides methods of treating or preventing an unspecified infection by administering a composition that decreases the activity or expression of a gene that is involved in the pathogenesis of three or more pathogens. Therefore, the present invention provides a method of decreasing infection in a subject comprising: a) diagnosing a subject with an unspecified infection and; b) administering a composition that decreases the expression or activity of a gene or gene product set forth in Table 1, wherein the composition decreases infection by three or more pathogens. More specifically, the three or more pathogens can be selected from the group consisting of: a pox virus, BVDV, a herpes virus, HIV, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus.

The infection can be a viral infection, a parasitic infection, a bacterial infection or a fungal infection, to name a few. As utilized herein, "an unspecified intoxication" is an intoxication that presents symptoms associated with the toxicity of a toxin, but is not identified as toxicity associated with a specific toxin. Furthermore, as utilized herein, "an unspecified infection" is an infection that presents symptoms associated with an infection, but is not identified as specific infection. One of skill in the art, for example, a physician, a nurse, a physician's assistant, a medic or any other health practitioner would know how to diagnose the symptoms of toxicity or infection even though the actual toxin or pathogen may not be known. For example, the patient can present with one or more symptoms, including, but not limited to, a fever, fatigue, lesions, weight loss, inflammation, a rash, pain (for example, muscle ache, headache, ear ache, joint pain, severe abdominal pain etc.), urinary difficulties, respiratory symptoms (for example, coughing, bronchitis, lung failure, breathing difficulties, bronchiolitis, airway obstruction, wheezing, runny nose, sinusitis, congestion, etc.), gastrointestinal symptoms (for example, nausea, diarrhea, vomiting, dehydration, abdominal pain, intestinal cramps, rectal bleeding, bloody stools, etc.), paralysis, CNS involvement, etc. This can occur in the event of a bioterrorist attack or a pandemic. In this event, one of skill in the art would know to administer a composition that inhibits toxicity and/or infection by decreasing the expression or activity of a gene or gene product set forth in Table 1 that is involved in the toxicity of several toxins and/or the pathogenesis of several pathogens. Similarly, if there is a threat of an unspecified intoxication and/or infection, for example, a threat of a bioterrorist attack, a composition that decreases the expression or activity of a gene or gene product set forth in Table 1 can be administered prophylactically to a subject to prevent an unspecified intoxication and/or infection in a subject.

By “treat,” “treating,” or “treatment” is meant a method of reducing the effects of an existing intoxication and/or infection. Treatment can also refer to a method of reducing the disease or condition itself rather than just the symptoms. The treatment can be any reduction from native levels and can be, but is not limited to, the complete ablation of the disease or the symptoms of the disease. Treatment can range from a positive change in a symptom or symptoms of intoxication and/or viral infection to complete amelioration of the intoxication and/or viral infection as detected by art-known techniques. For example, a disclosed method is considered to be a treatment if there is about a 10% reduction in one or more symptoms of the disease in a subject with the disease when compared to native levels in the same subject or control subjects. Thus, the reduction can be about a 10, 20, 30, 40, 50, 60, 70, 80, 90, 100%, or any amount of reduction in between as compared to native or control levels.

The methods of the present invention can also result in a decrease in the amount of time that it normally takes to see improvement in a subject. For example, a decrease in infection can be a decrease of hours, a day, two days, three days, four days, five days, six days, seven days, eight days, nine days, ten days, eleven days, twelve days, thirteen days, fourteen days, fifteen days or any time in between that it takes to see improvement in the symptoms, viral load or any other parameter utilized to measure improvement in a subject. For example, if it normally takes 7 days to see improvement in a subject not taking the composition, and after administration of the composition, improvement is seen at 6 days, the composition is effective in decreasing infection. This example is not meant to be limiting, as one of skill in the art would know that the time for improvement will vary depending on the infection.

As utilized herein, by “prevent,” “preventing,” or “prevention” is meant a method of precluding, delaying, averting, obviating, forestalling; stopping, or hindering the onset, incidence, severity, or recurrence of intoxication and/or infection. For example, the disclosed method is considered to be a prevention if there is about a 10% reduction in onset, incidence, severity, or recurrence of intoxication and/or infection, or symptoms of intoxication and/or infection (e.g., inflammation, fever, lesions, weight loss, etc.) in a subject exposed to a toxin and/or a pathogen when compared to control subjects exposed to a toxin and/or a pathogen that did not receive a composition for decreasing intoxication and/or infection. Thus, the reduction in onset, incidence, severity, or recurrence of infection can be about a 10, 20, 30, 40, 50, 60, 70, 80, 90, 100%, or any amount of reduction in between as compared to control subjects. For example, and not to be limiting, if about 10% of the subjects in a population do not become intoxicated and/or infected as compared to subjects that did not receive preventive treatment, this is considered prevention.

Also provided is a method of decreasing the toxicity of a toxin in a subject comprising: a) administering a composition that decreases the expression or activity of a gene or gene product set forth in Table 1 in a subject with toxicity from an unspecified toxin; b) diagnosing the type of toxicity in the subject and; c) administering a composition that decreases the expression or activity of a gene or a gene product set forth in Table 1 for the diagnosed toxicity. Further provided is a method of treating toxicity caused by a toxin comprising: a) diagnosing a subject with an intoxication; and b) removing a drug from the subject that decreases the expression or activity of a gene or gene product set forth in Table 1, if the toxicity is not a toxicity that is inhibited by a composition that decreases the expression or activity of a gene or gene product set forth in Table 1.

Also provided is a method of decreasing infection in a subject comprising:

a) administering a composition that decreases the expression or activity of a gene or gene product set forth in Table 1 in a subject with an unspecified infection; b) diagnosing the type of infection in the subject and; c) administering a composition that decreases the expression or activity of a gene or a gene product set forth in Table 1 for the diagnosed infection. Further provided is a method of treating viral infection comprising: a) diagnosing a subject with a viral infection; and b) removing a drug from the subject that decreases the expression or activity of a gene or gene product set forth in Table 1, if the viral infection is not a viral infection that is inhibited by a composition that decreases the expression or activity of a gene or gene product set forth in Table 1.

As mentioned above, upon recognizing that a subject has an intoxication and/or infection or the symptoms of an intoxication and/or infection, for example, in the case of a bioterrorist attack or a pandemic, given that a gene or gene product set forth in Table 1 can be involved in the toxicity of several toxins and/or the pathogenesis of several pathogens, a practitioner can prescribe or administer a composition that decreases the expression or activity of the gene or gene product. After administration, the practitioner, who can be the same practitioner a different practitioner, can diagnose the type of toxicity and/or infection in a subject. This diagnosis can be a differential diagnosis where the practitioner distinguishes between toxicities and/or infections by comparing signs or symptoms and eliminates certain types of toxicities and/or infection before arriving at the diagnosis for a specific toxicity and/or infection, or a diagnosis based on a test that is specific for a particular intoxication and/or infection. Once a specific toxicity and/or infection is diagnosed, if the gene or gene product is involved in the toxicity of this toxin and/or the pathogenesis of this infection, the practitioner can prescribe or administer a composition that decreases the expression or activity of that gene or gene product. This can be the same composition administered prior to diagnosis of the specific toxicity and/or infection or a different composition that decreases expression or activity.

Also provided is a method of preventing toxicity in a subject comprising administering to a subject susceptible to an unspecified toxin a composition that decreases the expression or activity of a gene or gene product set forth in Table 1. The composition can be administered in response to a lethal outbreak of a toxin. For example, the toxin can be released during a bioterrorist attack. If there is a threat of toxicity from an unspecified toxin, such as resulting from exposure to a *Clostridium perfringens* toxin, *Clostridium difficile* toxin, *Clostridium botulinum* toxin, *Clostridium tetani* toxin, saxitoxin, tetrodotoxin, abrin, conotoxin, Staphlococcal toxin, *E. coli* toxin, streptococcal toxin, diphtheria toxin, cholera toxin, pertussis toxin, *pseudomonas* toxin, *bacillus* toxin, shigatoxin, T-2 toxin, or an anthrax toxin, to name a few, a composition can be administered prophylactically to a subject to prevent the toxicity from an unspecified toxin in a subject. One of skill in the art would know to administer a composition that inhibits toxicity by decreasing the expression or activity of any gene or gene product set forth in Table 1 that is involved in the pathogenesis of two or more, three or more, four or more; or five or more toxins.

Also provided is a method of preventing infection in a subject comprising administering to a subject susceptible to an unspecified infection a composition that decreases the expression or activity of a gene or gene product set forth in Table 1. The composition can be administered in response to a lethal outbreak of an infection. For example, the infection can be a pandemic or a bioterrorist created infection. If there is a threat of an unspecified infection, such as a viral infection, a bacterial infection, a parasitic infection or an infection by a chimeric pathogenic agent, to name a few, a composition can be administered prophylactically to a subject to prevent an unspecified infection in a subject. The threat can also come in the form of a toxin. One of skill in the art would know to administer a composition that inhibits infection by decreasing the expression or activity of any gene or gene product set forth in Table 1 that is involved in the pathogenesis of two or more, three or more, four or more; or five or more pathogens.

Such prophylactic use can decrease the number of people in a population that are intoxicated and/or infected, thus preventing further spread of a pandemic or decreasing the effects of a bioterrorist attack.

In the methods of the present invention, the composition can comprise one or more of, a chemical, a compound, a small molecule, an inorganic molecule, an aptamer, an organic molecule, a drug, a protein, a CDNA, a peptide, an antibody, a morpholino, a triple helix molecule, an siRNA, an shRNAs, an miRNA, an antisense nucleic acid or a ribozyme that decreases the expression or activity of a gene or gene product set forth in Table 1. The composition can be administered before or after intoxication and/or infection. The decrease in toxicity and/or infection in a subject need not be complete as this decrease can be a 10%, 20%, 30%, 40%, 50%, 60%, 70%, 80%, 90%, 100% or any other percentage decrease in between as long as a decrease occurs. This decrease can be correlated with amelioration of symptoms associated with toxicity and/or infection. These compositions can be administered to a subject alone or in combination with other therapeutic agents described herein, such as anti-viral compounds, antibacterial agents, antifungal agents, antiparasitic agents, anti-inflammatory agents, anti-cancer agents, etc. Examples of toxins, viral infections, bacterial infections, fungal infections parasitic infections are set forth above. The compounds set forth herein or identified by the screening methods set forth herein can be administered to a subject to decrease toxicity and/or infection by any toxin, pathogen or infectious agent set forth herein. Any of the compounds set forth herein or identified by the screening methods of the present invention can also be administered to a subject to decrease the toxicity and/or infection by any toxin and/or pathogen, now known or later discovered in which a gene or gene product set forth in Table 1 is involved.

Various delivery systems for administering the therapies disclosed herein are known, and include encapsulation in liposomes, microparticles, microcapsules, expression by recombinant cells, receptor-mediated endocytosis (Wu and Wu, *J. Biol. Chem.* 1987, 262:4429-32), and construction of therapeutic nucleic acids as part of a retroviral or other vector. Methods of introduction include, but are not limited to, mucosal, topical, intradermal, intrathecal, intranasal, intratracheal, via nebulizer, via inhalation, intramuscular, otic delivery (ear), eye delivery (for example, eye drops), intraperitoneal, vaginal, rectal, intravenous, subcutaneous, intranasal, and oral routes. The compounds can be administered by any convenient route, for example by infusion or bolus injection, by absorption through epithelial or mucocutaneous linings (for example, oral mucosa, rectal, vaginal and intestinal mucosa, etc.) and can be administered together with other biologically active agents. Administration can be systemic or local. Pharmaceutical compositions can be delivered locally to the area in need of treatment, for example by topical application or local injection.

Pharmaceutical compositions are disclosed that include a therapeutically effective amount of an RNA, DNA, antisense molecule, ribozyme, siRNA, shRNA molecule, miRNA molecule, aptamer, drug, protein, small molecule, peptide inorganic molecule, organic molecule, antibody or other therapeutic agent, alone or with a pharmaceutically acceptable carrier. Furthermore, the pharmaceutical compositions or methods of treatment can be administered in combination with (such as before, during, or following) other therapeutic treatments, such as other antiviral agents, antibacterial agents, antifungal agents and antiparasitic agents.

For all of the administration methods disclosed herein, each method can optionally comprise the step of diagnosing a subject with an intoxication and/or infection or diagnosing a subject in need of prophylaxis or prevention of intoxication and/or infection.

Delivery Systems

The pharmaceutically acceptable carriers useful herein are conventional. *Remington's Pharmaceutical Sciences*, by Martin, Mack Publishing Co., Easton, Pa., 15th Edition (1975), describes compositions and formulations suitable for pharmaceutical delivery of the therapeutic agents herein disclosed. In general, the nature of the carrier will depend on the mode of administration being employed. For instance, parenteral formulations usually include injectable fluids that include pharmaceutically and physiologically acceptable fluids such as water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension; emulsion, tablet, pill, capsule, sustained release formulation, or powder. For solid compositions (for example powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

Embodiments of the disclosure including medicaments can be prepared with conventional pharmaceutically acceptable carriers, adjuvants and counterions as would be known to those of skill in the art.

The amount of therapeutic agent effective in decreasing or inhibiting toxicity or infection can depend on the nature of the toxin or pathogen and its associated disorder or condition, and can be determined by standard clinical techniques. Therefore, these amounts will vary depending on the type of virus, bacteria, fungus, parasite or other pathogen. For example, the dosage can be anywhere from 0.01 mg/kg to 100 mg/kg. Multiple dosages can also be administered depending on the type of toxin or pathogen, and the subject's condition. In addition, in vitro assays can be employed to identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

In an example in which a nucleic acid is employed to reduce toxicity or infection, such as an antisense or siRNA molecule, the nucleic acid can be delivered intracellularly (for example by expression from a nucleic acid vector or by receptor-mediated mechanisms), or by an appropriate nucleic acid expression vector which is administered so that it becomes intracellular, for example by use of a retroviral vector (see U.S. Pat. No. 4,980,286), or by direct injection, or by use of microparticle bombardment (such as a gene gun: Biolistic, Dupont), or coating with lipids or cell-surface receptors or transfecting agents, or by administering it in linkage to a homeobox-like peptide which is known to enter the nucleus (for example Joliot et al., *Proc. Natl. Acad. Sci. USA* 1991, 88:1864-8). siRNA carriers also include, polyethylene glycol (PEG), PEG-liposomes, branched carriers composed of histidine and lysine (HK polymers), chitosan-thiamine pyrophosphate carriers, surfactants (for example, Survanta and Infasurf), nanochitosan carriers, and D5W solution. The present disclosure includes all forms of nucleic acid delivery, including synthetic oligos, naked DNA, plasmid and viral delivery, integrated into the genome or not.

As mentioned above, vector delivery can be via a viral system, such as a retroviral vector system which can package a recombinant retroviral genome (see e.g., Pastan et al., *Proc. Natl. Acad. Sci. U.S.A,* 85:4486, 1988; Miller et al., *Mol. Cell. Biol.* 6:2895, 1986). The recombinant retrovirus can then be used to infect and thereby deliver to the infected cells a nucleic acid, for example an antisense molecule or siRNA. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), and pseudotyped retroviral vectors (Agrawal et al., *Exper. Hematol.* 24:738-747, 1996). Other nonpathogenic vector systems such as the foamy virus vector can also be utilized (Park et al. "Inhibition of simian immunodeficiency virus by foamy virus vectors expressing siRNAs." *Virology.* 2005 Sep. 20). It is also possible to deliver short hairpin RNAs (shRNAs) via vector delivery systems in order to inhibit gene expression (See Pichler et al. "In vivo RNA interference-mediated ablation of MDR1 P-glycoprotein." *Clin Cancer Res.* 2005 Jun. 15; 11(12): 4487-94; Lee et al. "Specific inhibition of HIV-1 replication by short hairpin RNAs targeting human cyclin T1 without inducing apoptosis." *FEBS Lett.* 2005 Jun. 6; 579(14):3100-6.).

Physical transduction techniques can also be used, such as liposome delivery and receptor-mediated and other endocytosis mechanisms (see, for example. Schwartzenberger et al., *Blood* 87:472-478, 1996) to name a few examples. This invention can be used in conjunction with any of these or other commonly used gene transfer methods.

Transgenic Cells and Non-Human Mammals

The present invention also provides a non-human transgenic mammal comprising a functional deletion of a gene set forth in Table 1, wherein the mammal has decreased susceptibility to the toxicity of a toxin and/or infection by a pathogen, such as a virus, a bacterium, a fungus or a parasite. Exemplary transgenic non-human mammals include, but are not limited to, ferrets, fish, guinea pigs, chinchilla, mice, monkeys, rabbits, rats, chickens, cows, and pigs. Such knock-out animals are useful for reducing the transmission of viruses from animals to humans and for further validating a target. In the transgenic animals of the present invention one or both alleles of a gene set forth in Table 1 can be functionally deleted.

By "decreased susceptibility" is meant that the animal is less susceptible to toxicity and/or infection or experiences decreased toxicity of a toxin and/or infection by a pathogen as compared to an animal that does not have one or both alleles of a gene set forth in Table 1 functionally deleted. The animal does not have to be completely resistant to the toxin and/or pathogen. For example, the animal can be 10%, 20%, 30%, 40%, 50%, 60%, 70%, 80%, 90%, 100% or any percentage in between less susceptible to the toxicity of a toxin or infection by a pathogen as compared to an animal that does not have a functional deletion of a gene set forth in Table 1. Furthermore, decreasing toxicity and/or infection or decreasing susceptibility to toxicity and/or infection includes decreasing receptor binding, inflammation responses, entry, replication, pathogenesis, insertion, lysis, or other steps in the toxicity of a toxin or the replication strategy of a virus or other pathogen into a cell or subject, or combinations thereof.

Therefore, the present invention provides a non-human transgenic mammal comprising a functional deletion of a gene set forth in Table 1, wherein the mammal has decreased susceptibility to the toxicity of a toxin and/or infection by a pathogen, such as a virus, a bacterium, a parasite or a fungus. A functional deletion is a mutation, partial or complete deletion, insertion, or other variation made to a gene sequence that inhibits production of the gene product or renders a gene product that is not completely functional or non-functional. Functional deletions can be made by insertional mutagenesis (for example via insertion of a transposon or insertional vector), by site directed mutagenesis, via chemical mutagenesis, via radiation or any other method now known or developed in the future that results in a transgenic animal with a functional deletion of a gene set forth in Table 1.

Alternatively, a nucleic acid sequence such as siRNA, a morpholino or another agent that interferes with a gene set forth in Table 1 can be delivered. The expression of the sequence used to knock-out or functionally delete the desired gene can be regulated by an appropriate promoter sequence. For example, constitutive promoters can be used to ensure that the functionally deleted gene is not expressed by the animal. In contrast, an inducible promoter can be used to control when the transgenic animal does or does not express the gene of interest. Exemplary inducible promoters include tissue-specific promoters and promoters responsive or unresponsive to a particular stimulus (such as light, oxygen, chemical concentration, such as a tetracycline inducible promoter).

The transgenic animals of the present invention that comprise a functionally deleted a gene set forth in Table 1 can be examined during exposure to various toxins and pathogens. Comparison data can provide insight into mechanisms of toxicity as well as the life cycles of pathogens. Moreover, knock-out animals or functionally deleted (such as birds or pigs) that are otherwise susceptible to toxicity or an infection (for example influenza) can be made to resist toxicity or infection, conferred by disruption of the gene. If disruption of the gene in the transgenic animal results in an increased resistance to toxicity and/or infection, these transgenic animals can be bred to establish flocks or herds that are less susceptible to toxicity and/or infection.

Transgenic animals, including methods of making and using transgenic animals, are described in various patents and publications, such as WO 01/43540; WO 02/19811; U.S. Pub. Nos: 2001-0044937 and 2002-0066117; and U.S. Pat. Nos. 5,859,308; 6,281,408; and 6,376,743; and the references cited therein.

The transgenic animals of this invention also include conditional gene knockdown animals produced, for example, by utilizing the SIRIUS-Cre system that combines siRNA for specific gene-knockdown, Cre-loxP for tissue-specific expression and tetracycline-on for inducible expression. These animals can be generated by mating two parental lines that contain a specific siRNA of interest gene and tissue-specific recombinase under tetracycline control. See Chang et al. "Using siRNA Technique to Generate Transgenic Animals with Spatiotemporal and Conditional Gene Knockdown." American Journal of Pathology 165:1535-1541 (2004) which is hereby incorporated in its entirety by this reference regarding production of conditional gene knockdown animals.

The present invention also provides cells including an altered or disrupted gene set forth in Table 1 that are resistant to the toxicity of a toxin or infection by a pathogen. These cells can be in vitro, ex vivo or in vivo cells and can have one or both alleles altered. These cells can also be obtained from the transgenic animals of the present invention. Such cells therefore include cells having decreased susceptibility to a toxin and/or to a virus or any of the other pathogens described herein, including bacteria, parasites and fungi.

Since the genes set forth herein are also involved in viral infection, also provided herein are methods of overexpressing any of the genes set forth in Table 1 in host cells. Overexpression of these genes can provide cells that increase the amount of virus produced by the cell, thus allowing more efficient production of viruses. Also provided is the overexpression of the genes set forth herein in avian eggs, for example, in chicken eggs.

Methods of screening agents, such as a chemical, a compound, a small or large molecule, an organic molecule, an inorganic molecule, a peptide, a drug, a protein, a cDNA, an antibody, a morpholino, a triple helix molecule, an siRNA, an shRNAs, an miRNA, an antisense nucleic acid or a ribozyme set forth using the transgenic animals described herein are also provided.

Screening for Resistance to Infection

Also provided herein are methods of screening host subjects for resistance to toxicity and/or infection by characterizing a nucleotide sequence or amino acid sequence of a host gene set forth in Table 1. The nucleic acid or amino acid sequence of a subject can be isolated, sequenced, and compared to the wild type sequence of a gene set forth in Table 1. The greater the similarity between that subject's nucleic acid sequence or amino acid sequence and the wildtype sequence, the more susceptible that person is to toxicity and/or infection, while a decrease in similarity between that subject's nucleic acid sequence or amino acid sequence and the wildtype sequence, the more resistant that subject can be to intoxication and/or infection. Such screens can be performed for any gene set forth in Table I for any species.

Assessing the genetic characteristics of a population can provide information about the susceptibility or resistance of that population to the toxicity of a toxin and/or viral infection. For example, polymorphic analysis of alleles in a particular human population, such as the population of a particular city or geographic area, can indicate how susceptible that population is to toxicity and/or infection. A higher percentage of alleles substantially similar to a wildtype gene set forth in Table 1 can indicate that the population is more susceptible to toxicity and/or infection, while a large number of polymorphic alleles that are substantially different than a wildtype gene sequence can indicate that a population is more resistant to toxicity and/or infection. Such information can be used, for example, in making public health decisions about vaccinating susceptible populations.

The present invention also provides a method of screening a cell for a variant form of a gene set forth in Table 1. A variant can be a gene with a functional deletion, mutation or alteration in the gene such that the amount or activity of the gene product is altered. These cells containing a variant form of a gene can be contacted with a toxin and/or a pathogen to determine if cells comprising a naturally occurring variant of a gene set forth in Table 1 differs in their resistance to toxicity and/or infection. For example, cells from an animal, for example, a chicken, can be screened for a variant form of a gene set forth in Table 1. If a naturally occurring variant is found and chickens possessing a variant form of the gene in their genome are less susceptible to toxicity and/or infection, these chickens can be selectively bred to establish flocks that are resistant to toxicity and/or infection. By utilizing these methods, flocks of chickens that are resistant to avian flu or other toxins and/or pathogens can be established. Similarly, other animals can be screened for a variant form of a gene set forth in Table 1. If a naturally occurring variant is found and animals possessing a variant form of the gene in their genome are less susceptible to toxicity and/or infection, these animals can be selectively bred to establish populations that are resistant to toxicity and/or infection. These animals include, but are not limited to, cats, dogs, livestock (for example, cattle, horses, pigs, sheep, goats, etc.), laboratory animals (for example, mouse, monkey, rabbit, rat, gerbil, guinea pig, etc.) and avian species (for example, flocks of chickens, geese, turkeys, ducks, pheasants, pigeons, doves etc.). Therefore, the present application provides populations of animals that comprise a naturally occurring variant of a gene set forth in Table 1 that results in decreased susceptibility to the toxicity of a toxin and/or viral infection, thus providing populations of animals that are less susceptible to the toxicity of a toxin and/or viral infection. Similarly, if a naturally occurring variant is found and animals possessing a variant form of the gene in their genome are less susceptible to the toxicity of a toxin and/or bacterial, parasitic or fungal infection, these animals can be selectively bred to establish populations that are resistant to the toxicity of a toxin and/or bacterial, parasitic or fungal infection.

Screening Methods

The present invention provides a method of identifying a compound that binds to a gene product set forth in Table 1 and can decrease the toxicity of a toxin in a cell comprising: a) contacting a compound with a gene product set forth in Table 1; b) detecting binding of the compound to the gene product; and c) associating the binding with a decrease in toxicity by the toxin.

The present invention provides a method of identifying an agent that decreases the toxicity of a toxin in a cell comprising: a) administering the agent to a cell containing a cellular gene encoding a gene product set forth in Table 1; and b) detecting the level and/or activity of the gene product produced by the cellular gene, a decrease or elimination of the gene product and/or gene product activity indicating an agent with antitoxin activity.

Also provided is a method of identifying an agent that decreases the toxicity of a toxin in a cell comprising: a) administering the agent to a cell containing a cellular gene encoding a gene product set forth in Table 1; b) contacting the cell with a toxin; and c) determining the level of toxicity, a decrease or elimination of toxicity indicating that the agent is an agent that decreases the toxicity of a toxin.

This method can further comprise optimizing a compound that binds the gene product in an assay that determines the functional ability to decrease the toxicity of two or more toxins. This method can be cell based or an in vivo assay. The two or more toxins can be any two or more toxins set forth herein. For example, the two or more toxins can be botulinum neurotoxins, ricin, *Clostridium perfringens* toxins, *Clostridium difficile* toxins, *Clostridium tetani* toxins, saxitoxins, tetrodotoxins, abrin, conotoxins, Staphlococcal toxins, *E. coli* toxins, streptococcal toxins, diphtheria toxin, cholera toxin, pertussis toxin, *pseudomonas* toxin, *bacillus* toxin, shigatoxins, T-2 toxins, anthrax toxins, cyanotoxins, hemotoxins, necrotoxins, and mycotoxins, such as aflatoxin, amatoxin, citrinin, cytohalasin, ergotamine, fumonisin, gliotoxin, ibotenic acid, muscimol, ochratoxin, patulin, sterigmatocystin, trichothecene, vomitoxin, zeranol, and zearalenone, chimeric forms of the toxins listed herein, and the like. The cell population used in the method can be the same cell population for each toxin or can be different cell populations.

This method can further comprise measuring the level of expression and/or activity of the gene product set forth in Table 1. This method can further comprise associating the level of toxicity with the level of expression and/or activity a gene product set forth in Table 1. In the screening methods disclosed herein, the level of toxicity can be measured, for example, by measuring cytotoxicity.

In the methods of the present invention, if the agent has previously been identified as an agent that decreases or inhibits the level and/or activity of a gene product set forth in Table 1, this can indicate a decrease in the toxicity of a toxin. A decrease in toxicity as compared to toxicity in a cell that was not contacted with the agent known to decrease or inhibit the level and/or activity of the gene product can be sufficient to identify the agent as an agent that decreases or inhibits the toxicity of a toxin.

The methods described above can be utilized to identify any agent with an activity that decreases toxicity, prevents toxicity or promotes cellular survival after contact with a toxin(s). Therefore, the cell can be contacted with a toxin before, or after being contacted with the agent. The cell can also be contacted concurrently with the toxin and the agent. The agents identified utilizing these methods can be used to inhibit toxicity in cells either in vitro, ex vivo or in vivo.

In the methods described herein, once the cell containing a cellular gene encoding a gene product set forth in Table 1 has been contacted with an agent, the level of toxicity can be assessed by measuring cell viability, apoptosis, LDH release or any other marker of cytotoxicity known one of ordinary skill in the art. For example, the level of toxicity can be measured CytoTox-Glo assay (see Niles, A. et at. (2007) *Anal. Biochem.* 366, 197-206) or the Cell-Titer-Glo assay from Promega. If there is a decrease in toxicity then the composition is an effective agent that decreases toxicity. This decrease does not have to be complete as the decrease can be a 10%, 20%, 30%, 40%, 50%, 60%, 70%, 80%, 90%, 100% decrease or any percentage decrease in between.

The present invention also provides a method of identifying a compound that binds to a gene product set forth in Table 1 and can decrease infection of a cell by a pathogen comprising: a) contacting a compound with a gene product set forth in Table 1; b) detecting binding of the compound to the gene product; and c) associating the binding with a decrease in infection by the pathogen.

The present invention provides a method of identifying an agent that decreases infection of a cell by a pathogen comprising: a) administering the agent to a cell containing a cellular gene encoding a gene product set forth in Table 1; and b) detecting the level and/or activity of the gene product produced by the cellular gene, a decrease or elimination of the gene product and/or gene product activity indicating an agent with antipathogenic activity.

Also provided is a method of identifying an agent that decreases infection in a cell by a pathogen comprising: a) administering the agent to a cell containing a cellular gene encoding a gene product set forth in Table 1; b) contacting the cell with a pathogen; and c) determining the level of infection, a decrease or elimination of infection indicating that the agent is an agent that decreases infection.

The present invention also provides a method of identifying a compound that binds to a gene product set forth in Table 1 and can decrease infection by three or more pathogens comprising: a) contacting a compound with a gene product set forth in Table 1; b) detecting binding of the compound to the gene product; and c) associating binding with a decrease in infection by three or more pathogens. This method can further comprise optimizing a compound that binds the gene product in an assay that determines the functional ability to decrease infection by three or more pathogens. This method can be cell based or an in vivo assay. The three or more pathogens can be any three or more pathogens set forth herein. For example, the three or more pathogens can be respiratory pathogens selected from the group consisting of picornaviruses, orthomyxoviruses, paramyxoviruses, coronaviruses or adenoviruses. In another example, the three or more pathogens can be gastrointestinal pathogens selected from filoviruses, flaviviruses, calciviruses and reoviruses. The three or more pathogens can also be a combination of respiratory and gastrointestinal viruses. In another example, the three or more pathogens can be selected from the group consisting of: an HIV virus, a pox virus, a herpes virus, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanr Forest Virus, Yellow Fever, Rabies, Chikungunya virus or a Dengue fever virus. The cell population used in the method can be the same cell population for each pathogen or can be different cell populations. Typically, the agent would be administered to a different cell population for each pathogen assayed. For example, and not to be limiting, if the pathogens are viruses, a cell population is contacted with the agent and a first virus, another cell population is contacted with the agent and second virus, a third cell population is contacted with the agent and a third virus etc. in order to determine whether the agent inhibits infection by three or more viruses. Since the cell type will vary depending on whether or not a given virus can infect the cell, one of skill in the art would know how to pair the cell type with the virus in order to perform the assay.

This method can further comprise measuring the level of expression and/or activity of the gene product set forth in Table 1. This method can further comprise associating the level of infection with the level of expression and/or activity a gene product set forth in Table 1. In the screening methods disclosed herein, the level of infection can be measured, for example, by measuring viral replication.

In the methods of the present invention, if the agent has previously been identified as an agent that decreases or inhibits the level and/or activity of a gene product set forth in Table 1, this can indicate a decrease in infection. A decrease in infection as compared to infection in a cell that was not contacted with the agent known to decrease or inhibit the level and/or activity of the gene product can be sufficient to identify the agent as an agent that decreases or inhibits infection.

The methods described above can be utilized to identify any agent with an activity that decreases infection, prevents infection or promotes cellular survival after infection with a pathogen(s). Therefore, the cell can be contacted with a pathogen before, or after being contacted with the agent. The cell can also be contacted concurrently with the pathogen and the agent. The agents identified utilizing these methods can be used to inhibit infection in cells either in vitro, ex vivo or in vivo.

In the methods described herein, once the cell containing a cellular gene encoding a gene product set forth in Table 1 has been contacted with an agent, the level of infection can be assessed by measuring an antigen or other product associated with a particular infection. For example, the level of viral infection can be measured by real-time quantitative reverse transcription-polymerase chain reaction (RT-PCR) assay (See for example, Payungporn et al. "Single step multiplex real-time RT-PCR for H5N1 influenza A virus detection." *J Virol Methods*. Sep. 22, 2005; Landolt et al. "Use of real-time reverse transcriptase polymerase chain reaction assay and cell culture methods for detection of swine influenza A viruses" *Am J Vet Res.* 2005 January; 66(1):119-24). If there is a decrease in infection then the composition is an effective agent that decreases infection. This decrease does not have to be complete as the decrease can be a 10%, 20%, 30%, 40%, 50%, 60%, 70%, 80%, 90%, 100% decrease or any percentage decrease in between.

The present invention further provides a method of identifying a compound that binds to a gene product set forth in Table 1 and can decrease the toxicity of a toxin in a cell and decrease infection in a cell by a pathogen comprising: a) contacting a compound with a gene product set forth in Table 1; b) detecting binding of the compound to the gene product; and c) associating the binding with a decrease in toxicity by the toxin and infection by the pathogen.

The present invention provides a method of identifying an agent that decreases the toxicity of a toxin in a cell and decreases infection in a cell by a pathogen comprising: a) administering the agent to a cell containing a cellular gene encoding a gene product set forth in Table 1; and b) detecting the level and/or activity of the gene product produced by the cellular gene, a decrease or elimination of the gene product and/or gene product activity indicating an agent with antitoxin and antipathogenic activity.

Also provided is a method of identifying an agent that decreases the toxicity of a toxin in a cell and decreases infection in a cell by a pathogen comprising: a) administering the agent to a cell containing a cellular gene encoding a gene product set forth in Table 1; b) contacting the cell with a toxin and a pathogen; and c) determining the level of intoxication and infection, a decrease or elimination of toxicity and infection indicating that the agent is an agent that decreases the toxicity of a toxin and the infection by a pathogen.

In the methods of the present invention any cell that can be intoxicated with a toxin and/or infected with a pathogen can be utilized. The cell can be prokaryotic or eukaryotic, such as a cell from an insect, fish, crustacean, mammal, bird, reptile, yeast or a bacterium, such as *E. coli*. The cell can be part of an organism, or part of a cell culture, such as a culture of mammalian cells or a bacterial culture. The cell can also be in a nonhuman subject thus providing in vivo screening of agents that decrease the toxicity of a toxin and/or infection by a pathogen. Cells susceptible to intoxication and/or infection are well known and can be selected based on the pathogen of interest.

The test agents or compounds used in the methods described herein can be, but are not limited to, chemicals, small molecules, inorganic molecules, organic molecules, drugs, proteins, cDNAs, large molecules, antibodies, morpholinos, triple helix molecule, peptides, siRNAs, shRNAs, miRNAs, antisense RNAs, ribozymes or any other compound. The compound can be random or from a library optimized to bind to a gene or gene product set forth in Table 1. Drug libraries optimized for the proteins in the class of proteins provided herein can also be screened or tested for binding or activity. Compositions identified with the disclosed approaches can be used as lead compositions to identify other compositions having even greater antitoxin and/or antipathogenic activity. For example, chemical analogs of identified chemical entities, or variants, fragments or fusions of peptide agents, can be tested for their ability to decrease toxicity and/or infection using the disclosed assays. Candidate agents can also be tested for safety in animals and then used for clinical trials in animals or humans.

In the methods set forth herein, the level of the gene product can be measured by any standard means, such as by detection with an antibody specific for the protein. The nucleic acids set forth herein and fragments thereof can be utilized as primers to amplify nucleic acid sequences, such as a gene transcript of a gene set forth in Table 1 by standard amplification techniques. For example, expression of a gene transcript can be quantified by real time PCR using RNA isolated from cells. A variety of PCR techniques are familiar to those skilled in the art. For a review of PCR technology, see White (1997) and the publication entitled "PCR Methods and Applications" (1991, Cold Spring Harbor Laboratory Press), which is incorporated herein by reference in its entirety for amplification methods. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated herein by reference in its entirety for PCR methods. One of skill in the art would know how to design and synthesize primers that amplify any of the nucleic acid sequences set forth herein or a fragment thereof.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4'.5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N$^1$,N$^1$-tetramethyl-6-carboxyrhodamine (TAMRA), radioactive labels, e.g. $^{32}$P, $^{35}$S, $^3$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified fragment, can be analyzed by one of a number of methods known in the art. The nucleic acid can be sequenced by dideoxy or other methods. Hybridization with the sequence can also be used to determine its presence, by Southern blots, dot blots, etc.

In the methods of the present invention, the level of gene product can be compared to the level of the gene product in a control cell not contacted with the compound. The level of gene product can be compared to the level of the gene product in the same cell prior to addition of the compound. Activity or function, can be measured by any standard means, such as by enzymatic assays that measure the conversion of a substrate to a product or binding assays that measure the binding of a gene product set forth in Table 1 to another protein, for example.

Moreover, the regulatory region of a gene set forth in Table 1 can be functionally linked to a reporter gene and compounds can be screened for inhibition of reporter gene expression. Such regulatory regions can be isolated from genomic sequences and identified by any characteristics observed that are characteristic for regulatory regions of the species and by their relation to the start codon for the coding region of the gene. As used herein, a reporter gene encodes a reporter protein. A reporter protein is any protein that can be specifically detected when expressed. Reporter proteins are useful for detecting or quantitating expression from expression sequences. Many reporter proteins are known to one of skill in the art. These include, but are not limited to, β-galactosidase, luciferase, and alkaline phosphatase that produce specific detectable products. Fluorescent reporter proteins can also be used, such as green fluorescent protein (GFP), cyan fluorescent protein (CFP), red fluorescent protein (RFP) and yellow fluorescent protein (YFP).

The toxicity of a toxin can be measured via any of the toxicity measurement methods known to one of skill in the art, such as, for example, the MTT cell proliferation assay from Promega, the CytoTox-Glo assay (see Niles, A. et al. (2007) *Anal. Biochem.* 366, 197-206) or the Cell-Titer-Glo assay from Promega.

Viral infection can also be measured via cell based assays. Briefly, cells (20,000 to 2,500,000) are infected with the desired pathogen, and the incubation continued for 3-7 days. The antiviral agent can be applied to the cells before, during, or after infection with the pathogen. The amount of virus and agent administered can be determined by skilled practitioners. In some examples, several different doses of the potential therapeutic agent can be administered, to identify optimal dose ranges. Following transfection, assays are conducted to determine the resistance of the cells to infection by various agents.

For example, if analyzing viral infection, the presence of a viral antigen can be determined by using antibody specific for the viral protein then detecting the antibody. In one example, the antibody that specifically binds to the viral protein is labeled, for example with a detectable marker such as a fluorophore. In another example, the antibody is detected by using a secondary antibody containing a label. The presence of bound antibody is then detected, for example using microscopy, flow cytometry and ELISA. Similar methods can be used to monitor bacterial, protozoal, or fungal infection (except that the antibody would recognize a bacterial, protozoal, or fungal protein, respectively).

Alternatively, or in addition, the ability of the cells to survive intoxication and/or viral infection is determined, for example, by performing a cell viability assay, such as trypan blue exclusion. Plaque assays can be utilized as well.

The amount of protein in a cell, can be determined by methods standard in the art for quantitating proteins in a cell, such as Western blotting, ELISA, ELI SPOT, immunoprecipitation, immunofluorescence (e.g., FACS), immunohistochemistry, immunocytochemistry, etc., as well as any other method now known or later developed for quantitating protein in or produced by a cell.

The amount of a nucleic acid in a cell can be determined by methods standard in the art for quantitating nucleic acid in a cell, such as in situ hybridization, quantitative PCR, RT-PCR, Taqman assay, Northern blotting, ELISPOT, dot blotting, etc., as well as any other method now known or later developed for quantitating the amount of a nucleic acid in a cell.

The ability of an antitoxin agent to prevent or decrease the toxicity of a toxin, for example, any of the toxins listed above, can be assessed in an animal model. Several animal models for measuring the toxicity of toxins are known in the art.

The ability of an antiviral agent to prevent or decrease infection by a virus, for example, any of the viruses listed above, can be assessed in an animal model. Several animal models for viral infection are known in the art. For example, mouse HIV models are disclosed in Sutton et al. (*Res. Initial Treat. Action,* 8:22-4, 2003) and Pincus et al. (*AIDS Res.*

Hum. Retroviruses 19:901-8, 2003); guinea pig models for Ebola infection are disclosed in Parren et al. (*J. Virol.* 76:6408-12, 2002) and Xu et al. (*Nat. Med.* 4:37-42, 1998); cynomolgus monkey (*Macaca fascicularis*) models for influenza infection are disclosed in Kuiken et al. (*Vet. Pathol.* 40:304-10, 2003); mouse models for herpes are disclosed in Wu et al. (*Cell Host Microbe* 22:5(1):84-94. 2009); pox models are disclosed in Smee et al. (*Nucleosides Nucleotides Nucleic Acids* 23(1-2):375-83, 2004) and in Bray et al. (*J. Infect. Dis.* 181(1):10-19); and *Franciscella tularensis* models are disclosed in Klimpel et al. (*Vaccine* 26(52):6874-82. 2008).

Other animal models for influenza infection are also available. These include, but are not limited to, a cotton rat model disclosed by Ottolini et al. (*J. Gen. Virol.*, 86(Pt 10): 2823-30, 2005), as well as ferret and mouse models disclosed by Maines et al. (*J. Virol.* 79(18):11788-11800, 2005). One of skill in the art would know how to select an animal model for assessing the in vivo activity of an agent for its ability to decrease infection by viruses, bacteria, fungi and parasites.

Such animal models can also be used to test agents for an ability to ameliorate symptoms associated with toxicity and/or viral infection. In addition, such animal models can be used to determine the $LD_{50}$ and the $ED_{50}$ in animal subjects, and such data can be used to determine the in vivo efficacy of potential agents. Animal models can also be used to assess antibacterial, antifungal and antiparasitic agents.

Animals of any species, including, but not limited to, birds, ferrets, cats, mice, rats, rabbits, fish (for example, zebra fish) guinea pigs, pigs, micro-pigs, goats, and non-human primates, e.g., baboons, monkeys, and chimpanzees, can be used to generate an animal model of intoxication, viral infection, bacterial infection, fungal infection or parasitic infection if needed.

For example, for a model of viral infection, the appropriate animal is inoculated with the desired virus, in the presence or absence of the antiviral agent. The amount of virus and agent administered can be determined by skilled practitioners. In some examples, several different doses of the potential therapeutic agent (for example, an antiviral agent) can be administered to different test subjects, to identify optimal dose ranges. The therapeutic agent can be administered before, during, or after infection with the virus. Subsequent to the treatment, animals are observed for the development of the appropriate viral infection and symptoms associated therewith. A decrease in the development of the appropriate viral infection, or symptoms associated therewith, in the presence of the agent provides evidence that the agent is a therapeutic agent that can be used to decrease or even inhibit viral infection in a subject. For example, a virus can be tested which is lethal to the animal and survival is assessed. In other examples, the weight of the animal or viral titer in the animal can be measured. Similar models and approaches can be used for bacterial, fungal and parasitic infections.

In the methods of the present invention, the level of toxicity and/or infection can be associated with the level of gene expression and/or activity, such that a decrease or elimination of toxicity and/or infection associated with a decrease or elimination of gene expression and/or activity indicates that the agent is effective against the toxin and/or pathogen. For example, the level of toxicity and/or infection can be measured in a cell after administration of siRNA that is known to inhibit a gene product set forth in Table 1. If there is a decrease in toxicity and/or infection then the siRNA is an effective agent that decreases toxicity and/or infection. This decrease does not have to be complete as the decrease can be a 10%, 20%, 30%, 40%, 50%, 60%, 70%, 80%, 90%, 100% decrease or any percentage decrease in between. In the event that the compound is not known to decrease expression and/or activity of a gene product set forth in Table 1, the level of expression and/or activity of can be measured utilizing the methods set forth above and associated with the level of toxicity and/or infection. By correlating a decrease in expression and/or activity with a decrease in toxicity and/or infection, one of skill in the art can confirm that a decrease in toxicity and/or infection is affected by a decrease in expression and/or activity of a gene or gene product set forth in Table 1. Similarly, the level of toxicity and/or infection can be measured in a cell, utilizing the methods set forth above and known in the art, after administration of a chemical, small molecule, drug, protein, cDNA, antibody, aptamer, shRNA, miRNA, morpholino, antisense RNA, ribozyme or any other compound. If there is a decrease in toxicity and/or infection, then the chemical, small molecule, drug, protein, cDNA, antibody, shRNA, miRNA, morpholino, antisense RNA, ribozyme or any other compound is an effective antitoxin and/or antipathogenic agent.

The genes and nucleic acids of the invention can also be used in polynucleotide arrays. Polynucleotide arrays provide a high throughput technique that can assay a large number of polynucleotide sequences in a single sample. This technology can be used, for example, to identify samples with reduced expression of as compared to a control sample. This technology can also be utilized to determine the effects of reduced expression of a gene set forth in Table 1 on other genes. In this way, one of skill in the art can identify genes that are upregulated or downregulated upon reducing expression of a gene set forth in Table 1. Similarly, one of skill in the art can identify genes that are upregulated or downregulated upon increased expression of a gene set forth in Table 1. This allows identification of other genes that are upregulated or downregulated upon modulation of expression that can be targets for therapy, such as antitoxin therapy, antiviral therapy, antibacterial therapy, antiparasitic therapy or antifungal therapy.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides selected from nucleotide sequences set forth under GenBank Accession Nos. herein and other nucleic acid sequences that would be selected by one of skill in the art depending on what genes, in addition to one or more of the genes set forth in Table 1 are being analyzed.

The array can also be a microarray that includes probes to different polymorphic alleles of these genes. A polymorphism exists when two or more versions of a nucleic acid sequence exist within a population of subjects. For example, a polymorphic nucleic acid can be one where the most common allele has a frequency of 99% or less. Different alleles can be identified according to differences in nucleic acid sequences, and genetic variations occurring in more than 1% of a population (which is the commonly accepted frequency for defining polymorphism) are useful polymorphisms for certain applications. The allelic frequency (the proportion of all allele nucleic acids within a population that are of a specified type) can be determined by directly counting or estimating the number and type of alleles within a population. Polymorph isms and methods of determining allelic frequencies are discussed in Hartl, D. L. and Clark, A.

G., Principles of Population Genetics, Third Edition (Sinauer Associates, Inc., Sunderland Mass., 1997), particularly in chapters 1 and 2.

These microarrays can be utilized to detect polymorphic alleles in samples from subjects. Such alleles may indicate that a subject is more susceptible to toxicity and/or infection or less susceptible to toxicity and/or infection. For example, microarrays can be utilized to detect polymorphic versions of genes set forth in Table 1 that result in decreased gene expression and/or decreased activity of the gene product to identify subjects that are less susceptible to the toxicity of a toxin and/or viral infection. In addition, the existence of an allele associated with decreased expression in a healthy individual can be used to determine which genes are likely to have the least side effects if the gene product is inhibited or bound or may be selected for in commercial animals and bred into the population.

The substrate can be any substrate to which polynucleotide probes can be attached, including but not limited to glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734. Commercially available polynucleotide arrays, such as Affymetrix GeneChip™, can also be used. Use of the GeneChip™ to detect gene expression is described, for example, in Lockhart et al., Nature Biotechnology 14:1675 (1996); Chee et al., Science 274:610 (1996); Hacia et al., Nature Genetics 14:441, 1996; and Kozal et al., Nature Medicine 2:753, 1996.

Disclosed herein in particular is the toxin receptor PVRL3, which can be used to bind to either the A or B toxin of *C. difficile* to find points of interaction. This interaction can then be used to determine small molecules or antibodies that can be used in the treatment of *C. difficile* toxic infection. The crystal structure of PVRL3 while bound to *C. difficile* A and/or B toxin can also be used in the discovery of new molecules and antibodies for use in the treatment of *C. difficile* toxic infection. This can allow for the design of a single antibody or small molecule that can block both the A and the B toxin. Therefore disclosed are methods of screening for compounds and antibodies in the treatment of *C. difficile* toxins using the receptor PVRL3.

Methods of Making Compounds

The present invention provides a method of making a compound that decreases the toxicity of a toxin in a cell, comprising: a) synthesizing a compound; b) administering the compound to a cell containing a cellular gene encoding a gene product set forth in Table 1; c) contacting the cell with a toxin; d) determining the level of toxicity, a decrease or elimination of toxicity indicating that the agent is an agent that decreases toxicity; and e) associating the agent with decreasing expression or activity of the gene product.

Further provided is a method of making a compound that decreases the toxicity of a toxin in a cell, comprising: a) optimizing a compound to bind a gene product set forth in Table 1; b) administering the compound to a cell containing a cellular gene encoding the gene product; c) contacting the cell with toxin; d) determining the level of toxicity, a decrease or elimination of toxicity indicating the making of a compound that decreases toxicity in a cell by a toxin. This method can further synthesizing therapeutic quantities of the compound.

The present invention also provides a method of synthesizing a compound that binds to a gene product set forth in Table 1 and decreases the toxicity of a toxin in a cell comprising: a) contacting a library of compounds with a gene product set forth in Table 1; b) associating binding with a decrease in toxicity; and c) synthesizing derivatives of the compounds from the library that bind to the gene product.

The present invention also provides a business method to reduce the cost of drug discovery of drugs that can reduce the toxicity of a toxin comprising: screening, outside of the United States, for drugs that reduce toxicity by binding to or reducing the function of a gene product set forth in Table 1; and b) importing drugs that reduce toxicity into the United States. Also provided is a method of making drugs comprising directing the synthesis of drugs that reduce toxicity by binding to or reducing the function of a gene or gene product set forth in Table 1.

The present invention provides a method of making a compound that decreases infection of a cell by a pathogen, comprising: a) synthesizing a compound; b) administering the compound to a cell containing a cellular gene encoding a gene product set forth in Table 1; c) contacting the cell with an infectious pathogen; d) determining the level of infection, a decrease or elimination of infection indicating that the agent is an agent that decreases infection; and e) associating the agent with decreasing expression or activity of the gene product.

Further provided is a method of making a compound that decreases infection in a cell by a pathogen, comprising: a) optimizing a compound to bind a gene product set forth in Table 1; b) administering the compound to a cell containing a cellular gene encoding the gene product; c) contacting the cell with an infectious pathogen; d) determining the level of infection, a decrease or elimination of infection indicating the making of a compound that decreases infection in a cell by a pathogen. This method can further synthesizing therapeutic quantities of the compound.

The present invention also provides a method of synthesizing a compound that binds to a gene product set forth in Table 1 and decreases infection by a pathogen comprising: a) contacting a library of compounds with a gene product set forth in Table 1; b) associating binding with a decrease in infection; and c) synthesizing derivatives of the compounds from the library that bind to the gene product.

The present invention also provides a business method to reduce the cost of drug discovery of drugs that can reduce infection by a pathogen comprising: screening, outside of the United States, for drugs that reduce infection by binding to or reducing the function of a gene product set forth in Table 1; and b) importing drugs that reduce infection into the United States. Also provided is a method of making drugs comprising directing the synthesis of drugs that reduce infection by binding to or reducing the function of a gene or gene product set forth in Table 1.

EXAMPLES

Example 1: Identification of Genes Essential for the Toxicity of a Toxin

CaCo-2 cells were used for the preparation of gene trap libraries, as they are efficiently killed by toxins, and represent physiologically relevant cells. Parental, toxin-sensitive cells were infected with the U3neoSV1 vector (MO1=0.1). Following infection of CaCo-2 cells with U3neoSV1, the medium was changed and the cells grown overnight at 37° C. On the following day, neomycin was added to select for cells containing insertion of the U3neoSV1 vector, and cells were grown to confluence. All the toxins used in this study are currently available or can be made.

Selecting Cells Resistant to the Toxicity of a Toxin

CaCo-2 cells transfected with the gene trap vector were plated in six 100 mm dishes (approximately 5×106 cells per dish) in MEM supplemented with 10% FBS and 750 μg/mL G418. Toxin was added to a final concentration of 15 pM, and the treated cells were incubated at 37° C. for 16 hours. The toxin-containing medium was replaced with fresh medium and surviving cells were cultured for 5 days. Medium then was replaced with fresh MEM containing 7.5 pM toxin, and the cells were incubated for 16 hours. The toxin-containing medium was replaced with fresh medium and surviving cells were cultured for 5 days. Medium then was replaced with fresh MEM containing 7.5 pM toxin, and the cells were incubated for 16 hours. Medium then was replaced with fresh MEM and surviving cells were allowed to grow 14 days before clonal populations were isolated.

Identifying the Gene Targets Disrupted in the Toxin Resistant Cells

To identify the mutated genes from toxin-resistant cells isolated from the gene-trap libraries, genomic DNAs were extracted using a QIAamp DNA Blood Maxi Kit (QIAGEN). The *E. coli* shuttle vector and genomic DNA flanking the retrovirus integration site was recovered. Individual colonies were amplified, and plasmid DNA containing the recovered genomic DNAs was sequenced using primers annealing to the shuttle vector. The target genes were identified through bioinformatics.

Example 2: Identification of Genes Essential in Viral Infection

Following infection with the U3NeoSV1 retrovirus gene trap shuttle vector, libraries of mutagenized Vero cells were isolated in which each clone contained a single gene disrupted by provirus integration. Gene entrapment was performed essentially as described in U.S. Pat. No. 6,448,000 and U.S. Pat. No. 6,777,177. The entrapment libraries were infected with HSV, RSV, rhinovirus or Dengue fever virus and virus-resistant clones were selected as described below.

HSV

Four days prior to infection, Vero gene trap library cells were thawed at room temperature. 13 mLs of complete growth medium and a thawed gene trap library aliquot were combined in a sterile 15 mL conical tube. This was centrifuged at 1000 rpm for 5 minutes to pellet the cells. The supernatant was discarded and the cells were resuspended in complete growth medium and the aliquot of cells seeded into 4 T150 flask. The cells were allowed to grow for 4 days at 37° C. in 5% $CO_2$ or until the cells were 70-100% confluent. On the day of infection, the medium in the T150 flasks was replaced with 19 mLs of fresh complete growth medium immediately before infecting the cells. One aliquot of HSV Strain 186 was thawed from the −80° C. freezer at 4° C. for 30 minutes. The HSV-2 (186 strain) was diluted in complete growth medium to a final concentration of 495 p.f.u./ml. 1 mL of diluted virus was added to each of the 4 T150 flasks containing Vero gene trap library cells. The cells were incubated at 37° C., 5% $CO_2$ for 2 hours. The medium was discarded from the flasks into the waste container and replaced with 20 mLs of fresh complete growth medium to remove the inoculum. The cells were incubated at 37° C., 5% $CO_2$. Infection was allowed to proceed without changing the medium until the cells were approximately 90% dead or dying (routinely 3 or 4 days post-infection). From then on, the medium was changed daily through day 7 post-infection. The medium was changed on days 10, 14, 17, 21, etc. post-infection. HSV-resistant colonies (clones) were observed 2-3 weeks post-infection by examining the underside of the flasks. When visible colonies appeared, they were marked and looked at under the microscope to determine which colonies are either (A) unhealthy/dying cells or are (B) actually two colonies very close together, 24-well plate(s) with 1 mL of complete growth medium in as many wells as there were resistant colonies were prepared. Resistant cells were trypsinized and cells from each HSV-resistant clone were transferred to a single well of the 24 well plate (already containing 1 ml of complete growth medium). This process was repeated for each colony. The colonies were grown until cells in several wells approach 20-30% confluency. At this point, cells were detached and seeded into duplicate 24-well plates. Resistance confirmation was performed by re-infecting clones in one 24-well plate. Following identification of resistant clones, resistant clones in the uninfected 24-well plates were expanded in T75 flasks for subsequent genomic DNA isolation (DNeasy kits, Qiagen, Inc.).

Identitication of Genes Disrupted in HSV-Resistant Clones

The U3NeoSV1 gene trap vector contains a plasmid origin of replication and ampicillin resistance gene; thus, regions of genomic DNA adjacent to the targeting vector were readily cloned by plasmid rescue and sequenced. The flanking sequences were compared to the nucleic acid databases to identify candidate cellular genes that confer resistance to lytic infection by herpes simplex virus when altered by gene entrapment.

RSV

Four days prior to infection, Vero gene trap library cells were thawed at room temperature. 13 mLs of complete growth medium and a thawed gene trap library aliquot were combined in a sterile 15 mL conical tube. This was centrifuged at 1000 rpm for 5 minutes to pellet the cells. The supernatant was discarded and the cells were resuspended in complete growth medium and the aliquot of cells seeded into 4 T150 flask. The cells were allowed to grow for 4 days at 37° C. in 5% $CO_2$ or until the cells were 70-100% confluent. On the day of infection, the medium in the T150 flasks was replaced with 19 mLs of fresh complete growth medium immediately before infecting the cells. One aliquot of RSV A2 strain was thawed from the −80° C. freezer at 4° C. for 30 minutes. The RSV A2 strain was diluted in complete growth medium to a final concentration of 11,812 p.f.u./ml. 1 mL of diluted virus was added to each of the 4 T150 flasks containing Vero gene trap library cells. The cells were incubated at 37° C., 5% $CO_2$ for 2 hours. The medium was discarded from the flasks and replaced with 20 mLs of fresh complete growth medium to remove the inoculum. The cells were incubated at 37° C., 5% $CO_2$. Infection was allowed to proceed without changing the medium until the cells were approximately 90% dead or dying (approximately 3 or 4 days post-infection). From then on, the medium was changed daily through day 7 post-infection. The medium was changed on days 10, 14, 17, 21, etc. post-infection. RSV-resistant colonies (clones) were observed 2-3 weeks post-infection by examining the underside of the flasks. When visible colonies appeared, they were marked and looked at under the microscope to determine which colonies are either (A) unhealthy/dying cells or are (B) actually two colonies very close together. 24-well plate(s) with 1 mL of complete growth medium in as many wells as there were resistant colonies were prepared. Resistant cells were trypsinized and cells from each RSV-resistant clone were transferred to a single well of the 24 well plate (already containing 1 ml of complete growth medium). This process was repeated tor each colony. The colonies were grown until cells in several wells approach 20-30% confluency. At this point, cells were detached and seeded into duplicate 24-well plates. Resistance confirmation was performed by re-infecting clones in one 24-well plate. Following identification of resistant clones, resistant clones in the uninfected 24-well plates were expanded in T75 flasks for subsequent genomic DNA isolation (DNeasy kits, Qiagen, Inc.).

Identitication of Genes Disrupted in RSV-Resistant Clones

The U3NeoSV1 gene trap vector contains a plasmid origin of replication and ampicillin resistance gene; thus, regions of genomic DNA adjacent to the targeting vector were readily cloned by plasmid rescue and sequenced. The flanking sequences were compared to the nucleic acid databases to identify candidate cellular genes that confer resistance to lytic infection by respiratory syncytial virus when altered by gene entrapment.

Rhinovirus

Four days prior to infection, an aliquot of TZM-bl gene trap library cells were thawed at room temperature. 13 mLs of complete growth medium and thawed gene trap library aliquot were combined in a sterile 15 mL conical tube. This was centrifuged at 1000 rpm for 5 minutes to pellet the cells. The supernatant was discarded and the cells were resuspended in complete growth medium and the aliquot of cells was seeded into 4 T150 flasks with reclosable lids. Cells were allowed grow for 4 days at 37° C. in 5% $CO_2$ or until the cells were 70-100% confluent. On the day of infection, the medium was replaced in the T150 flasks with 19 mLs of fresh complete growth medium immediately before infecting the cells. One aliquot of Rhinovirus-16 Strain 11757 from the −80° C. freezer was thawed at 4° C. tor 30 minutes. Rhinovirus was diluted in complete growth medium to a final concentration of $1\times10^5$ p.f.u./ml. Approximately 1 mL of the diluted virus was added to each of 4 T150 flasks containing TZM-bl gene trap library cells. 200 μL of sterile MgCl2 was added to each T150 flask (final MgCl2 concentration=40 mM). The T150 flasks were placed on a rocker and incubated at 33° C., 5% $CO_2$, rocking cells gently at the lowest setting. Infection was allowed to proceed without changing the medium until the cells were >99.9% dead or dying (routinely 6-7 days post-infection). The medium was changed and the flasks transferred to a 37° C., 5% $CO_2$ incubator.

The medium was changed on days 10, 14, 17, 21, etc. post-infection (following this pattern of days), while maintaining cells at 37° C., 5% $CO_2$.

Rhinovirus resistant clones were observed 2-3 weeks post-infection by examining the underside of the flasks. When visible colonies appeared, they were marked and looked at under the microscope to determine which colonies are either (A) unhealthy/dying cells or are (B) actually two colonies very close together. 24-well plate(s) with 1 mL of complete growth medium in as many wells as there were resistant colonies were prepared. Resistant cells were trypsinized and cells from each rhinovirus-resistant clone were transferred to a single well of the 24 well plate (already containing 1 ml of complete growth medium). This process was repeated for each colony. The colonies were grown until cells in several wells approach 20-30% confluency. At this point, cells were detached and seeded into duplicate 24-well plates. Resistance confirmation was performed by re-infecting clones in one 24-well plate. Following identification of resistant clones, resistant clones in the uninfected 24-well plates were expanded in T75 flasks for subsequent genomic DNA isolation (DNeasy kits, Qiagen, Inc.).

Identification of Genes Disrupted in Rhinovirus-Resistant Clones

The U3NeoSV1 gene trap vector contains a plasmid origin of replication and ampicillin resistance gene; thus, regions of genomic DNA adjacent to the targeting vector were readily cloned by plasmid rescue and sequenced. The flanking sequences were compared to the nucleic acid databases to identify candidate cellular genes that confer resistance to lytic infection by rhinovirus when altered by gene entrapment.

siRNA and Small Molecule Studies

Any of the genes set forth in Table 1 is further analyzed by contacting cells comprising a gene set forth in Table 1 with siRNA or small molecule that targets the gene product of the gene, and any pathogen or toxin set forth herein to identify the gene as a gene involved in pathogenic infection (for example, and not to be limiting, a pox virus, BVDV, a herpes virus, HIV, an RSV virus, an influenza virus, a hepatitis C virus, a hepatitis B virus, Epstein Barr Virus, Human Papilloma Virus, CMV, West Nile virus, a rhinovirus, an adenovirus, measles virus, Marburg virus, Ebola virus, Rift Valley Fever Virus, LCM, Junin virus, Machupo virus, Guanarito virus, Lassa Fever virus, Hantavirus, SARS virus, Nipah virus, Caliciviruses, Hepatitis A, LaCrosse, California encephalitis, VEE, EEE, WEE, Japanese Encephalitis Virus, Kyasanur Forest Virus, Yellow Fever, Rabies, Chikungunya virus or a Dengue fever virus), or toxicity, such as *C. difficile*. A decrease in viral infection or toxicity indicates that the gene is a gene that is involved in pathogenic infection or toxicity. This process can be performed for all of the genes set forth herein with any of the viruses, bacteria, parasites or fungi set forth herein.

siRNA Transfections can be performed as follows: Pools of 4 duplexed siRNA molecules targeting a gene of interest are reconstituted to a final working concentration of 50 μM as directed by the manufacturer (Qiagen). Twenty-four hours prior to transfection, cells are plated in 6-well dishes at $3\times10^5$ cells per well, such that at the time of transfection, the cells are approximately 30% confluent. Prior to transfection, the cells are washed once with 1× phosphate buffered saline, and the medium replaced with approximately 1.8 ml antibiotic-free medium. siRNA aliquots are diluted with Opti-MEM and RNAseOUT (Invitrogen), 100 μl and 1 μl per transfection, respectively. In a separate tube, transfection reagent Lipofectamine2000 (Invitrogen) or Oligofectamine (Invitrogen) are diluted in Opti-MEM as directed by the manufacturer. Following a 5 minute incubation at room temperature, the diluted siRNA is added to the transfection reagent mixture, and incubated for an additional 20 minutes prior to adding to independent wells of the 6-well dishes. Transfections are incubated at 37° C. for 48 hours without changing the medium.

Virus Infections and Toxicity: Following 48-hour transfection, medium is aspirated from 6-well plates. Viruses are diluted in the appropriate medium and 500 μl of either virus-free medium or virus dilution is added to each well, and adsorption is allowed to occur at the appropriate temperature for 1 hour. Following adsorption, inoculum is aspirated off the cells, cells are washed once with 1× phosphate buffered saline, and 2 ml growth medium is added to the cells. The infected cells are incubated for 72 hours at the appropriate temperature prior to harvesting samples for viral titration.

Viral and Toxin Genomic Extractions: Seventy-hours after inoculating cells, medium is harvested from 6-well dishes and centrifuged for 2 minutes at 10,000 rpm to remove any cellular debris. 200 µl of clarified medium is added to 25 µl Proteinase K, to which 200 µl PureLink96 Viral RNA/DNA lysis buffer (Invitrogen) is added according to the manufacturer. Samples were processed and viral genomic RNA or DNA is extracted using an epMotion 5075 robotics station (Eppendorf) and the PureLink96 Viral RNA/DNA kit (Invitrogen).

cDNA and Quantitative Real-Time PCR Reactions: 3 µl of extracted viral RNA is converted to cDNA using M-MLV reverse transcriptase (Invitrogen) and AmpliTaq Gold PCR buffer (Applied Biosystems), MgCl$_2$, dNTPs and RNAse-OUT (Invitrogen) are added to achieve a final concentration of 5 mM, 1 mM and 2U/µl, respectively. Random hexamers (Applied Biosystems) are added to obtain 2.5 mM final concentration. Reactions are incubated at 42° C. for 1 hour, followed by heat inactivation of the reverse transcriptase at 92° C. for 10 minutes. Quantitative real-time PCR reactions are set up in 10 µl volumes using 1 µl of template cDNA or extracted viral DNA using virus-specific TaqMan probes (Applied Biosystems) and RealMasterMix (Eppendorf). 2-step reactions are allowed to proceed through 40 to 50 cycles on an ep RealPlex thermocycler (Eppendorf). Quantitative standards for real-time PCR are constructed by cloning purified amplicons into pCR2-TOPO (Invitrogen) and sequenced as necessary.

The amount of toxicity the cells contacted with siRNA to the gene of interest is calculated and compared to the cell death associated in control cells that did not receive siRNA targeting the gene of interest.

Example 3: Small Molecule Interactions

The following are examples of small molecules that are known to interact with the genes disclosed in Table 1 and can be utilized to inhibit cellular intoxication and/or treat *C. difficile* infection.

LGALS3BP: neopterin, lactose
LGALS3: n-acetyllactosamine; c(yigsr)3-nh2; lactose; gal (beta 1-3)galnac; galactose.
CDH17: valacyclovir
SCSDL: lathosterol; 7-dehydrocholesterol; sterol; squalene
CCNG1: mimosine; retinoid; rapamycin; actinomycin d

What is claimed is:

1. An cell comprising a functional deletion in a nucleic acid encoding a gene product selected from the list consisting of: Transmembrane 4 superfamily 1 (SEQ ID NO:369), NEDD4 BP 2 like 2 (SEQ ID NO:370), ADP-ribosylation factor-like 6 interacting protein 1 (SEQ ID NO:371), SEC31A (SEQ ID NO:372), sterol-C5-desaturase (ERG3 delta-5-desaturase homolg, *S. cerevisiae*)-like (SEQ ID NO:373), and Fibronectin III Domain Containing I (SEQ ID NO:374).

2. The cell of claim 1, wherein the gene product has decreased activity.

3. The cell of claim 1, wherein the cell has decreased sensitivity to *C. difficile* toxin.

4. The cell of claim 1, wherein the gene product has decreased activity and wherein the cell has decreased sensitivity to *C. difficile* toxin.

5. The cell of claim 3, wherein the *C. difficile* toxin is *C. difficile* toxin A.

6. The cell of claim 3, wherein the *C. difficile* toxin is *C. difficile* toxin B.

* * * * *

SEQUENCE LISTING

```
<160> NUMBER OF SEQ ID NOS: 374

<210> SEQ ID NO 1
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 1
tgatccgctt tatcctcatc cagaa                                          25

<210> SEQ ID NO 2
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 2
cgagacgcca aacacaccaa ctttg                                          25

<210> SEQ ID NO 3
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 3
ccaaacacac caactttgtg gagtt                                          25

<210> SEQ ID NO 4
<211> LENGTH: 25
<212> TYPE: DNA
<213> ORGANISM: Artificial Sequence
<220> FEATURE:
<223> OTHER INFORMATION: synthetic construct; siRNA
```

```
<400> SEQUENCE: 4
caactttgtg gagttccgga acttt                                              25

<210> SEQ ID NO 5
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 5
actttgtgga gttccggaac tttaa                                              25

<210> SEQ ID NO 6
<211> LENGTH: 22
<212> TYPE: DNA
<213> ORGANISM: Artificial Sequence
<220> FEATURE:
<223> OTHER INFORMATION: synthetic construct; siRNA

<400> SEQUENCE: 6
gctcaggcca ttatgctgga tt                                                 22

<210> SEQ ID NO 7
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 7
cattatgctg ctggattgga cctca                                              25

<210> SEQ ID NO 8
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 8
gctgctggat tggacctcaa tgaca                                              25

<210> SEQ ID NO 9
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 9
cctactctgg gaagcgtgaa ccatt                                              25

<210> SEQ ID NO 10
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 10
gggaccacag tgctgatgga tttga                                              25
```

```
<210> SEQ ID NO 11
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 11
gagataatcg cagcaccaac ctgct                                          25

<210> SEQ ID NO 12
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 12
gagaagtgat gctgatggct gataa                                          25

<210> SEQ ID NO 13
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 13
agaagtgatg ctgatggctg ataaa                                          25

<210> SEQ ID NO 14
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 14
ggtgtggttt ctttggtgtt tctga                                          25

<210> SEQ ID NO 15
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 15
gatccatctg ttctgtccgg cgttt                                          25

<210> SEQ ID NO 16
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 16
ggctcctcga taaagtggag ctgat                                          25

<210> SEQ ID NO 17
<211> LENGTH: 25
<212> TYPE: DNA
<213> ORGANISM: Artificial Sequence
<220> FEATURE:
<223> OTHER INFORMATION: synthetic construct; siRNA
```

<400> SEQUENCE: 17
gctcctcgat aaagtggagc tgatg                                         25

<210> SEQ ID NO 18
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 18
gagctgatgc tgcccgagaa attga                                         25

<210> SEQ ID NO 19
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 19
tgcccgagaa attgaggccg ttgta                                         25

<210> SEQ ID NO 20
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 20
cccgagaaat tgaggccgtt gtaca                                         25

<210> SEQ ID NO 21
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 21
ccttgtggct ttctctactt cctct                                         25

<210> SEQ ID NO 22
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 22
gagcaagcat aagctgccaa accaa                                         25

<210> SEQ ID NO 23
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 23
caagtgatcc ttcagttcct ttgaa                                         25

<210> SEQ ID NO 24
<211> LENGTH: 25

```
<212> TYPE: DNA
<213> ORGANISM: Artificial Sequence
<220> FEATURE:
<223> OTHER INFORMATION: synthetic construct; siRNA

<400> SEQUENCE: 24
ggaactggga gaagatggct ttaaa                                          25

<210> SEQ ID NO 25
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 25
gaactgggag aagatggctt taaag                                          25

<210> SEQ ID NO 26
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 26
gagactaatt gagtctgcac acgat                                          25

<210> SEQ ID NO 27
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 27
tggcctcaga atgactgcaa gacta                                          25

<210> SEQ ID NO 28
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 28
caagactaag ggactttgaa gtaaa                                          25

<210> SEQ ID NO 29
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 29
ccattggcaa ctgacttgat ccgaa                                          25

<210> SEQ ID NO 30
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 30
```
tggagaaggt gtgttggaaa gtcaa					25

<210> SEQ ID NO 31
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 31
caggaaagcc cttcttgtat gtcaa					25

<210> SEQ ID NO 32
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 32
ccactcccaa tggccagctt tatta					25

<210> SEQ ID NO 33
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 33
catatccgct ggaaattcat gtaaa					25

<210> SEQ ID NO 34
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 34
caagatactc ctcagtacaa cttaa					25

<210> SEQ ID NO 35
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 35
cacaaacatt gggtccacca tctta					25

<210> SEQ ID NO 36
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 36
cggctaataa cggtgctctg ttgtt					25

<210> SEQ ID NO 37
<211> LENGTH: 25
<212> TYPE: DNA
<213> ORGANISM: Artificial Sequence

```
<220> FEATURE:
<223> OTHER INFORMATION: synthetic construct; siRNA

<400> SEQUENCE: 37
ccagctgcct catttggcga ataat                                              25

<210> SEQ ID NO 38
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 38
ccctgaactc catctcgcct ttgaa                                              25

<210> SEQ ID NO 39
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 39
caagcaatca tattcagctc cagaa                                              25

<210> SEQ ID NO 40
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 40
caggatccga tagctctctg cttat                                              25

<210> SEQ ID NO 41
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 41
ccttaatgtg catgatggtt gtgtt                                              25

<210> SEQ ID NO 42
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 42
cagacaatgc caatttacgt gtcat                                              25

<210> SEQ ID NO 43
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 43
gatggaactg ttaggtggtt tgata                                              25
```

```
<210> SEQ ID NO 44
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 44
cccgaaagat gatacagcac gagaa                                          25

<210> SEQ ID NO 45
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 45
gatgcagaga atgtctgata tgtta                                          25

<210> SEQ ID NO 46
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 46
gcaccttagc taagatcgcg gagat                                          25

<210> SEQ ID NO 47
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 47
caccttagct aagatcgcgg agata                                          25

<210> SEQ ID NO 48
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 48
ccttagctaa gatcgcggag ataga                                          25

<210> SEQ ID NO 49
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 49
gagatagaag cagagatggc tcgga                                          25

<210> SEQ ID NO 50
<211> LENGTH: 25
<212> TYPE: DNA
<213> ORGANISM: Artificial Sequence
<220> FEATURE:
<223> OTHER INFORMATION: synthetic construct; siRNA
```

```
<400> SEQUENCE: 50
gatagaagca gagatggctc ggact                                              25

<210> SEQ ID NO 51
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 51
tcaggaagct caatgacctg atcaa                                              25

<210> SEQ ID NO 52
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 52
gccaaggttc acgcctacat catca                                              25

<210> SEQ ID NO 53
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 53
cctacatcat cagctccctc aagaa                                              25

<210> SEQ ID NO 54
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 54
gctccctcaa gaaagagatg cccaa                                              25

<210> SEQ ID NO 55
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 55
cctcaagaaa gagatgccca atgtc                                              25

<210> SEQ ID NO 56
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 56
cacacattcc gggtcaacct cttta                                              25

<210> SEQ ID NO 57
```

```
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 57
gatcagtgac gagtgggata ttcca                                    25

<210> SEQ ID NO 58
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 58
ggaacttacg ttactggctt gaaga                                    25

<210> SEQ ID NO 59
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 59
gcttattgac ttctcacctt gtgaa                                    25

<210> SEQ ID NO 60
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 60
gagatccgag tgaggaacct gttca                                    25

<210> SEQ ID NO 61
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 61
aggagatgag aatactgtca ttgat                                    25

<210> SEQ ID NO 62
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 62
gagatgagaa tactgtcatt gatct                                    25

<210> SEQ ID NO 63
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 63
```
caagaggcag tatgcagatt gttca                                          25

<210> SEQ ID NO 64
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 64
cagtatgcag attgttcaga gattt                                          25

<210> SEQ ID NO 65
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 65
gactgtaatt cagagacgat ctgat                                          25

<210> SEQ ID NO 66
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 66
aggagatgag aatactgtca ttgat                                          25

<210> SEQ ID NO 67
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 67
gagatgagaa tactgtcatt gatct                                          25

<210> SEQ ID NO 68
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 68
caagaggcag tatgcagatt gttca                                          25

<210> SEQ ID NO 69
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 69
cagtatgcag attgttcaga gattt                                          25

<210> SEQ ID NO 70
<211> LENGTH: 25
<212> TYPE: DNA

```
<213> ORGANISM: Artificial Sequence
<220> FEATURE:
<223> OTHER INFORMATION: synthetic construct; siRNA

<400> SEQUENCE: 70
gactgtaatt cagagacgat ctgat                                              25

<210> SEQ ID NO 71
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 71
gcaaggagag ctattccgtg tacgt                                              25

<210> SEQ ID NO 72
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 72
caaggagagc tattccgtgt acgtg                                              25

<210> SEQ ID NO 73
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 73
aggagagcta ttccgtgtac gtgta                                              25

<210> SEQ ID NO 74
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 74
gagagctatt ccgtgtacgt gtaca                                              25

<210> SEQ ID NO 75
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 75
gctattccgt gtacgtgtac aaggt                                              25

<210> SEQ ID NO 76
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 76
aagaataggg cacaggtata ttgaa                                              25
```

```
<210> SEQ ID NO 77
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 77
gaatagggca caggtatatt gaaat                                           25

<210> SEQ ID NO 78
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 78
agggcacagg tatattgaaa tcttt                                           25

<210> SEQ ID NO 79
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 79
gggcacaggt atattgaaat cttta                                           25

<210> SEQ ID NO 80
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 80
ggtagagggt ataacagcat tggca                                           25

<210> SEQ ID NO 81
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 81
ccatgatgcg ttatctgggt ctgga                                           25

<210> SEQ ID NO 82
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 82
tgctgggcca ctgattgtgc cttat                                           25

<210> SEQ ID NO 83
<211> LENGTH: 24
<212> TYPE: DNA
<213> ORGANISM: Artificial Sequence
<220> FEATURE:
```

<223> OTHER INFORMATION: synthetic construct; siRNA

<400> SEQUENCE: 83
gctgggccac tgahgtgcct tata                                    24

<210> SEQ ID NO 84
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 84
tgattgtgcc ttataacctg cctttt                                  25

<210> SEQ ID NO 85
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 85
tggtgcctcg catgctgata acaat                                   25

<210> SEQ ID NO 86
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 86
gctggtgtgg tctgcaccaa tgaaa                                   25

<210> SEQ ID NO 87
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 87
gctggtgtgg tctgcaccaa tgaaa                                   25

<210> SEQ ID NO 88
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 88
gcagcaatgt caccatgagt gtgga                                   25

<210> SEQ ID NO 89
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 89
agggaccttc tcaggtactt ctact                                   25

<210> SEQ ID NO 90
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 90
caggtacttc tactcccgaa ggatt                                          25

<210> SEQ ID NO 91
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 91
acggaaacct gtgccattct gtgta                                          25

<210> SEQ ID NO 92
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 92
cggaaacctg tgccattctg tgtat                                          25

<210> SEQ ID NO 93
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 93
gccattctgt gtatgagaac gtttg                                          25

<210> SEQ ID NO 94
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 94
cattctgtgt atgagaacgt ttgca                                          25

<210> SEQ ID NO 95
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 95
gaggccctat gcaaggccaa cttta                                          25

<210> SEQ ID NO 96
<211> LENGTH: 25
<212> TYPE: DNA
<213> ORGANISM: Artificial Sequence
<220> FEATURE:
<223> OTHER INFORMATION: synthetic construct; siRNA

```
<400> SEQUENCE: 96
gctgccaatt ccataggtca caggt                                              25

<210> SEQ ID NO 97
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 97
tgccaattcc ataggtcaca ggtat                                              25

<210> SEQ ID NO 98
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 98
gccaattcca taggtcacag gtatg                                              25

<210> SEQ ID NO 99
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 99
ccaattccat aggtcacagg tatgt                                              25

<210> SEQ ID NO 100
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 100
caattccata ggtcacaggt atgtt                                              25

<210> SEQ ID NO 101
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 101
ccctgtaaca gcaactccat gtgga                                              25

<210> SEQ ID NO 102
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 102
gaggacatag ttatttgcag gagaa                                              25

<210> SEQ ID NO 103
<211> LENGTH: 25
```

```
<212> TYPE: DNA
<213> ORGANISM: Artificial Sequence
<220> FEATURE:
<223> OTHER INFORMATION: synthetic construct; siRNA

<400> SEQUENCE: 103
cagttgtaaa gaatctgaac cttct                                    25

<210> SEQ ID NO 104
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 104
gagggtcata ataatggtct cttaa                                    25

<210> SEQ ID NO 105
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 105
catgttaact ggaattgcat gactt                                    25

<210> SEQ ID NO 106
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 106
caagcataat ggaacagaca ggttt                                    25

<210> SEQ ID NO 107
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 107
gagaacggtg tgaagaccat cacct                                    25

<210> SEQ ID NO 108
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 108
cagcagggtt aaagaagcta agcaa                                    25

<210> SEQ ID NO 109
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 109
```
catttctcag ctccattcta ctgtt                                          25

<210> SEQ ID NO 110
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 110
tcacctgatt gaatttgcca ggaag                                          25

<210> SEQ ID NO 111
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 111
gagcattgga tatgatgata ctgat                                          25

<210> SEQ ID NO 112
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 112
cagctgagct tcaagaacat gtgca                                          25

<210> SEQ ID NO 113
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 113
agctgagctt caagaacatg tgcaa                                          25

<210> SEQ ID NO 114
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 114
gcttcaagaa catgtgcaag ctcaa                                          25

<210> SEQ ID NO 115
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 115
agaacatgtg caagctcaag ccgct                                          25

<210> SEQ ID NO 116
<211> LENGTH: 25
<212> TYPE: DNA
<213> ORGANISM: Artificial Sequence

```
<220> FEATURE:
<223> OTHER INFORMATION: synthetic construct; siRNA

<400> SEQUENCE: 116
gctgtatgag atccctgaca cctat                                          25

<210> SEQ ID NO 117
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 117
tccctgacac ctatgcccaa acaga                                          25

<210> SEQ ID NO 118
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 118
cacctatgcc caaacagagg gagat                                          25

<210> SEQ ID NO 119
<211> LENGTH: 23
<212> TYPE: DNA
<213> ORGANISM: Artificial Sequence
<220> FEATURE:
<223> OTHER INFORMATION: synthetic construct; siRNA

<400> SEQUENCE: 119
tgcccaaaca gagggagatg cag                                            23

<210> SEQ ID NO 120
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 120
gagaagattg tggacaagag cacaa                                          25

<210> SEQ ID NO 121
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 121
gaatatcagg gaagagtctt gttta                                          25

<210> SEQ ID NO 122
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 122
acggcaacga ttatcagcca gtaca                                          25
```

<210> SEQ ID NO 123
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 123
ccagtacaag ctatttccaa ccaga      25

<210> SEQ ID NO 124
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 124
tagaggaagg cgaattactt gtgtt      25

<210> SEQ ID NO 125
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 125
gaaggcgaat tacttgtgtt gtaaa      25

<210> SEQ ID NO 126
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 126
tgaagacagt ctaccgtcac gagaa      25

<210> SEQ ID NO 127
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 127
gggccatggg cttcattctg atgta      25

<210> SEQ ID NO 128
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 128
ccatgggctt cattctgatg tatga      25

<210> SEQ ID NO 129
<211> LENGTH: 25
<212> TYPE: DNA
<213> ORGANISM: Artificial Sequence
<220> FEATURE:
<223> OTHER INFORMATION: synthetic construct; siRNA

```
<400> SEQUENCE: 129
catcaccaat gaagagtcct tcaat                                          25

<210> SEQ ID NO 130
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 130
caccaatgaa gagtccttca atgct                                          25

<210> SEQ ID NO 131
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 131
gcttcaaagc caagctccac cgaaa                                          25

<210> SEQ ID NO 132
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 132
aagggtaatt cgaggtaaca cttat                                          25

<210> SEQ ID NO 133
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 133
gaaagcatgt cgatgtgcaa acaga                                          25

<210> SEQ ID NO 134
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 134
gacagaccac caacaccact cttta                                          25

<210> SEQ ID NO 135
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 135
ggaagacaat tgagcagtct cttct                                          25

<210> SEQ ID NO 136
```

```
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 136
catcttccga caagctatta gtctt                                          25

<210> SEQ ID NO 137
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 137
gacaagctat tagtcttctg attgt                                          25

<210> SEQ ID NO 138
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 138
caagtccgtc gagagattaa gttta                                          25

<210> SEQ ID NO 139
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 139
gaggttacag caaattacat gatga                                          25

<210> SEQ ID NO 140
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 140
gccttcatca tagactggta tataa                                          25

<210> SEQ ID NO 141
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 141
gctcagcaat tggatgcaac attta                                          25

<210> SEQ ID NO 142
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 142
```
caaggaagtt gtgattgccc agaat                                    25

<210> SEQ ID NO 143
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 143
ccagactaat ctggtagctt ctggt                                    25

<210> SEQ ID NO 144
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 144
gagcatggca gatcctgaat tgtta                                    25

<210> SEQ ID NO 145
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 145
cagaaacaag ttgacaagct ttcat                                    25

<210> SEQ ID NO 146
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 146
cggccaagtg tgttccataa catca                                    25

<210> SEQ ID NO 147
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 147
tccataacat caagctgttc gttct                                    25

<210> SEQ ID NO 148
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 148
cagctcatga tctccggcta cctaa                                    25

<210> SEQ ID NO 149
<211> LENGTH: 25
<212> TYPE: DNA

```
<213> ORGANISM: Artificial Sequence
<220> FEATURE:
<223> OTHER INFORMATION: synthetic construct; siRNA

<400> SEQUENCE: 149
gatatgccac aggacttcaa ggctt                                          25

<210> SEQ ID NO 150
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 150
ggcaactgct caagctacac agaaa                                          25

<210> SEQ ID NO 151
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 151
gggtcatttc aaagagggct tatga                                          25

<210> SEQ ID NO 152
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 152
ggtcatttca aagagggctt atgag                                          25

<210> SEQ ID NO 153
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 153
catttcaaag agggcttatg aggct                                          25

<210> SEQ ID NO 154
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 154
caaagagggc ttatgaggct gtgaa                                          25

<210> SEQ ID NO 155
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 155
aaagagggct tatgaggctg tgaaa                                          25
```

<210> SEQ ID NO 156
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 156
tgttctactg tgaactgctt gtgtg                                  25

<210> SEQ ID NO 157
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 157
gaactgcttg tgtgttggca ggcta                                  25

<210> SEQ ID NO 158
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 158
tgttggcagg ctaccggtaa gaatg                                  25

<210> SEQ ID NO 159
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 159
tggcaggcta ccggtaagaa tggtt                                  25

<210> SEQ ID NO 160
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 160
ggctaccggt aagaatggtt ggtgt                                  25

<210> SEQ ID NO 161
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 161
ccgcagcaag ctgagatctg tatct                                  25

<210> SEQ ID NO 162
<211> LENGTH: 25
<212> TYPE: DNA
<213> ORGANISM: Artificial Sequence
<220> FEATURE:

<223> OTHER INFORMATION: synthetic construct; siRNA

<400> SEQUENCE: 162
cagcaagctg agatctgtat ctgtg                                    25

<210> SEQ ID NO 163
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 163
catgaagact ttgtgtggct acatg                                    25

<210> SEQ ID NO 164
<211> LENGTH: 24
<212> TYPE: DNA
<213> ORGANISM: Artificial Sequence
<220> FEATURE:
<223> OTHER INFORMATION: synthetic construct; siRNA

<400> SEQUENCE: 164
acaacagact atgctgggch atta                                     24

<210> SEQ ID NO 165
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 165
caacagacta tgctgggctt attat                                    25

<210> SEQ ID NO 166
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 166
cctcctgtgc atcgcggcta atatt                                    25

<210> SEQ ID NO 167
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 167
tctgtattgg ctgctctcat tggaa                                    25

<210> SEQ ID NO 168
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 168
gcactgaacc caagcacatt gtgga                                    25

```
<210> SEQ ID NO 169
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 169
aacccaagca cattgtggaa tggaa                                          25

<210> SEQ ID NO 170
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 170
acccaagcac attgtggaat ggaat                                          25

<210> SEQ ID NO 171
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 171
ccggtgaatc caagtgtcct ctgat                                          25

<210> SEQ ID NO 172
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 172
cggtgaatcc aagtgtcctc tgatg                                          25

<210> SEQ ID NO 173
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 173
caagtgtcct ctgatggtca aagtt                                          25

<210> SEQ ID NO 174
<211> LENGTH: 25
<212> TYPE: DNA
<213> ORGANISM: Artificial Sequence
<220> FEATURE:
<223> OTHER INFORMATION: synthetic construct; siRNA

<400> SEQUENCE: 174
agtgtcctct gatggtcaaa gttct                                          25

<210> SEQ ID NO 175
<211> LENGTH: 25
<212> TYPE: DNA
<213> ORGANISM: Artificial Sequence
<220> FEATURE:
<223> OTHER INFORMATION: synthetic construct; siRNA
```

```
<400> SEQUENCE: 175
ccatcaatgt ggccgtgcat gtgtt                                          25

<210> SEQ ID NO 176
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 176
cttcgtctgg ctggtctctc                                                20

<210> SEQ ID NO 177
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 177
gtctggctgg tctctcggat                                                20

<210> SEQ ID NO 178
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 178
gtctggctgg tctctcggat t                                              21

<210> SEQ ID NO 179
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 179
ccttcgtctg gctggtctct                                                20

<210> SEQ ID NO 180
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 180
cttcgtctgg ctggtctct                                                 19

<210> SEQ ID NO 181
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 181
ggctctcatt ggtccttcgc a                                              21

<210> SEQ ID NO 182
<211> LENGTH: 20
```

<212> TYPE: DNA
<213> ORGANISM: Artificial Sequence
<220> FEATURE:
<223> OTHER INFORMATION: synthetic construct; antisense RNA

<400> SEQUENCE: 182
ggctctcatt ggtccttcgc                                             20

<210> SEQ ID NO 183
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 183
gagtagtcat agtcggctcc c                                           21

<210> SEQ ID NO 184
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 184
agtagtcata gtcggctccc                                             20

<210> SEQ ID NO 185
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 185
gtagtcatag tcggctccc                                              19

<210> SEQ ID NO 186
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 186
attatctccc tccgccatc                                              19

<210> SEQ ID NO 187
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 187
attatctccc tccgccatcg                                             20

<210> SEQ ID NO 188
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 188
ttatctccct ccgccatcg                                                   19

<210> SEQ ID NO 189
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 189
ttgttgtccc acccaagca                                                   19

<210> SEQ ID NO 190
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 190
atctccctcc gccatcgtct                                                  20

<210> SEQ ID NO 191
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 191
cactctctcc attccctgcc a                                                21

<210> SEQ ID NO 192
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 192
actctctcca ttccctgcca                                                  20

<210> SEQ ID NO 193
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 193
tcactctctc cattccctgc c                                                21

<210> SEQ ID NO 194
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 194
actctctcca ttccctgcca t                                                21

<210> SEQ ID NO 195
<211> LENGTH: 20
<212> TYPE: DNA
<213> ORGANISM: Artificial Sequence

```
<220> FEATURE:
<223> OTHER INFORMATION: synthetic construct; antisense RNA

<400> SEQUENCE: 195
cactctctcc attccctgcc                                                    20

<210> SEQ ID NO 196
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 196
gtgttctcgt ccctggctgt                                                    20

<210> SEQ ID NO 197
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 197
gttctcgtcc ctggctgttg t                                                  21

<210> SEQ ID NO 198
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 198
gtgttctcgt ccctggctgt t                                                  21

<210> SEQ ID NO 199
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 199
tgtgttctcg tccctggctg t                                                  21

<210> SEQ ID NO 200
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 200
ctgtgttctc gtccctggct                                                    20

<210> SEQ ID NO 201
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 201
gccatcttct cccagttcca                                                    20
```

```
<210> SEQ ID NO 202
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 202
gccatcttct cccagttcca g                                          21

<210> SEQ ID NO 203
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 203
gccatcttct cccagttcc                                             19

<210> SEQ ID NO 204
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 204
agccatcttc tcccagttcc                                            20

<210> SEQ ID NO 205
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 205
agccatcttc tcccagttcc a                                          21

<210> SEQ ID NO 206
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 206
gtcccttagt cttgcagtca                                            20

<210> SEQ ID NO 207
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 207
agtcccttag tcttgcagtc a                                          21

<210> SEQ ID NO 208
<211> LENGTH: 21
<212> TYPE: DNA
<213> ORGANISM: Artificial Sequence
<220> FEATURE:
<223> OTHER INFORMATION: synthetic construct; antisense RNA
```

-continued

<400> SEQUENCE: 208
gtcccttagt cttgcagtca t                                          21

<210> SEQ ID NO 209
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 209
agtcccttag tcttgcagtc                                            20

<210> SEQ ID NO 210
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 210
gtcccttagt cttgcagtc                                             19

<210> SEQ ID NO 211
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 211
actccctctc ctcaaactct                                            20

<210> SEQ ID NO 212
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 212
gcctcccatg tccttcact                                             19

<210> SEQ ID NO 213
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 213
ctccctctcc tcaaactct                                             19

<210> SEQ ID NO 214
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 214
cgacatactc cctctcctca                                            20

<210> SEQ ID NO 215

```
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 215
acgacatact ccctctcctc a                                              21

<210> SEQ ID NO 216
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 216
ccttcttcct cctcttcctc c                                              21

<210> SEQ ID NO 217
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 217
tcttcctcct cttcctcctc t                                              21

<210> SEQ ID NO 218
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 218
cttcctcctc ttcctcctct                                                20

<210> SEQ ID NO 219
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 219
tcttcctcct cttcctcctc                                                20

<210> SEQ ID NO 220
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 220
cttcttcctc ctcttcctcc t                                              21

<210> SEQ ID NO 221
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 221
```

```
actcttctct rctctcttcc                                               20

<210> SEQ ID NO 222
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 222
ctcgcctcat actctccttc t                                             21

<210> SEQ ID NO 223
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 223
ctcttctctt ctctcttcc                                                19

<210> SEQ ID NO 224
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 224
actcttctct tctctcttcc g                                             21

<210> SEQ ID NO 225
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 225
ctcgcctcat actctccttc                                               20

<210> SEQ ID NO 226
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 226
gcctcccttg tccttcttct                                               20

<210> SEQ ID NO 227
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 227
cctcccttgt ccttcttctt                                               20

<210> SEQ ID NO 228
<211> LENGTH: 20
<212> TYPE: DNA
```

```
<213> ORGANISM: Artificial Sequence
<220> FEATURE:
<223> OTHER INFORMATION: synthetic construct; antisense RNA

<400> SEQUENCE: 228
ctccaccacc accacccttt                                              20

<210> SEQ ID NO 229
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 229
cctcccttgt ccttcttct                                               19

<210> SEQ ID NO 230
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 230
gcctcccttg tccttcttct t                                            21

<210> SEQ ID NO 231
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 231
tcttcacttc tcttcccaca                                              20

<210> SEQ ID NO 232
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 232
gtcttcactt ctcttcccac a                                            21

<210> SEQ ID NO 233
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 233
cttcacttct cttcccaca                                               19

<210> SEQ ID NO 234
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 234
tcctcttccc agtcgtccac                                              20
```

<210> SEQ ID NO 235
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 235
gtctcctctt cccagtcgtc					20

<210> SEQ ID NO 236
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 236
tctcctcttc ccagtcgtcc					20

<210> SEQ ID NO 237
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 237
tctcctcttc ccagtcgtcc a					21

<210> SEQ ID NO 238
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 238
ctcctcttcc cagtcgtcca					20

<210> SEQ ID NO 239
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 239
ataccaccac ccatgccag					19

<210> SEQ ID NO 240
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 240
gaataccacc acccatgcca g					21

<210> SEQ ID NO 241
<211> LENGTH: 20
<212> TYPE: DNA
<213> ORGANISM: Artificial Sequence
<220> FEATURE:

<223> OTHER INFORMATION: synthetic construct; antisense RNA

<400> SEQUENCE: 241
agtccatcct cctccatcgg                                               20

<210> SEQ ID NO 242
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 242
gaataccacc acccatgcca                                               20

<210> SEQ ID NO 243
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 243
gtcatgatct ctgtcccacg t                                             21

<210> SEQ ID NO 244
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 244
tcaccatcct tcccgcccttt                                              20

<210> SEQ ID NO 245
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 245
gtttcccatt gtcctccgtg t                                             21

<210> SEQ ID NO 246
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 246
tcccattgtc ctccgtgttc t                                             21

<210> SEQ ID NO 247
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 247
tcccattgtc ctccgtgttc                                               20

<210> SEQ ID NO 248
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 248
ttcccattgt cctccgtgtt c                                    21

<210> SEQ ID NO 249
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 249
ccatccttct tctgtgcct                                       19

<210> SEQ ID NO 250
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 250
gccatccttc ttctgtgcct                                      20

<210> SEQ ID NO 251
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 251
gccatccttc ttctgtgcct t                                    21

<210> SEQ ID NO 252
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 252
ccatccttct tctgtgcctt                                      20

<210> SEQ ID NO 253
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 253
tgccatcctt cttctgtgcc t                                    21

<210> SEQ ID NO 254
<211> LENGTH: 19
<212> TYPE: DNA
<213> ORGANISM: Artificial Sequence
<220> FEATURE:
<223> OTHER INFORMATION: synthetic construct; antisense RNA

```
<400> SEQUENCE: 254
atccctctcc accttccgt                                                19

<210> SEQ ID NO 255
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 255
ccacgaatcc ctctccacct                                               20

<210> SEQ ID NO 256
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 256
accacgaatc cctctccacc t                                             21

<210> SEQ ID NO 257
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 257
aatccctctc caccttccg                                                19

<210> SEQ ID NO 258
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 258
ccacgaatcc ctctccacct t                                             21

<210> SEQ ID NO 259
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 259
ctgtctttct tcccttccc                                                19

<210> SEQ ID NO 260
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 260
actgtctttc ttcccttccc                                               20

<210> SEQ ID NO 261
<211> LENGTH: 20
```

<210> SEQ ID NO 261
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 261
ggtagactcc aggtgcaggt                                              20

<210> SEQ ID NO 262
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 262
gactgtcttt cttcccttcc c                                            21

<210> SEQ ID NO 263
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 263
gactctcctg ttgttctcat                                              20

<210> SEQ ID NO 264
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 264
ggcatcagtc aggtcccaca                                              20

<210> SEQ ID NO 265
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 265
tcttctccac caagccctcc                                              20

<210> SEQ ID NO 266
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 266
tcttctccac caagccctcc a                                            21

<210> SEQ ID NO 267
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 267
cttctccacc aagccctcca                                                      20

<210> SEQ ID NO 268
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 268
caagccctcc acctcctcat                                                      20

<210> SEQ ID NO 269
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 269
ttccgtttgg tcctcctccc                                                      20

<210> SEQ ID NO 270
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 270
tttccgtttg gtcctcctcc c                                                    21

<210> SEQ ID NO 271
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 271
gtttccgttt ggtcctcctc c                                                    21

<210> SEQ ID NO 272
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 272
ggtttccgtt tggtcctcct c                                                    21

<210> SEQ ID NO 273
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 273
ggtttccgtt tggtcctcc                                                       19

<210> SEQ ID NO 274
<211> LENGTH: 21
<212> TYPE: DNA
<213> ORGANISM: Artificial Sequence

```
<220> FEATURE:
<223> OTHER INFORMATION: synthetic construct; antisense RNA

<400> SEQUENCE: 274
gggttcgagg ctacagtgag a                                              21

<210> SEQ ID NO 275
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 275
ccgctgggct caagtgttt                                                 19

<210> SEQ ID NO 276
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 276
gggttcgagg ctacagtgag                                                20

<210> SEQ ID NO 277
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 277
gtggcaggat cacatctcac t                                              21

<210> SEQ ID NO 278
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 278
gggttcgagg ctacagtga                                                 19

<210> SEQ ID NO 279
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 279
ctggctgtca attcataggt c                                              21

<210> SEQ ID NO 280
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 280
gtcaattcat aggtcagagc                                                20
```

<210> SEQ ID NO 281
<211> LENGTH: 22
<212> TYPE: DNA
<213> ORGANISM: Artificial Sequence
<220> FEATURE:
<223> OTHER INFORMATION: synthetic construct; antisense RNA

<400> SEQUENCE: 281
tgtcaattct ataggtcaga gc                                    22

<210> SEQ ID NO 282
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 282
ggctgtcaat tcataggtca g                                     21

<210> SEQ ID NO 283
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 283
ggctgtcaat tcataggtca                                       20

<210> SEQ ID NO 284
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 284
ccacatggag ttgctgttac a                                     21

<210> SEQ ID NO 285
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 285
ccacatggag ttgctgttac                                       20

<210> SEQ ID NO 286
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 286
gggcacttcc acatggagtt                                       20

<210> SEQ ID NO 287
<211> LENGTH: 19
<212> TYPE: DNA
<213> ORGANISM: Artificial Sequence
<220> FEATURE:
<223> OTHER INFORMATION: synthetic construct; antisense RNA

```
<400> SEQUENCE: 287
gggcacttcc acatggagt                                              19

<210> SEQ ID NO 288
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 288
tgggcacttc cacatggagt t                                           21

<210> SEQ ID NO 289
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 289
gctcctaccc accactctat                                             20

<210> SEQ ID NO 290
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 290
gctcctaccc accactcta                                              19

<210> SEQ ID NO 291
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 291
gtgcctgatt cctcccttca                                             20

<210> SEQ ID NO 292
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 292
gctcctaccc accactctat t                                           21

<210> SEQ ID NO 293
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 293
ctcctaccca ccactctatt                                             20

<210> SEQ ID NO 294
```

```
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 294
ggtctcctgg ctgctcttgt                                              20

<210> SEQ ID NO 295
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 295
gtctcctggc tgctcttgtc                                              20

<210> SEQ ID NO 296
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 296
tctcctggct gctcttgtcc                                              20

<210> SEQ ID NO 297
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 297
agctgcatca tccgactccc                                              20

<210> SEQ ID NO 298
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 298
gctgctcttg tccatctctg c                                            21

<210> SEQ ID NO 299
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 299
cctcctccag ccacttgttc                                              20

<210> SEQ ID NO 300
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 300
```
cctcctccag ccacttgttc a                    21

<210> SEQ ID NO 301
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 301
gcctcctcca gccacttgtt                      20

<210> SEQ ID NO 302
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 302
cctcctccag ccacttgtt                       19

<210> SEQ ID NO 303
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 303
ctcctccagc cacttgttca                      20

<210> SEQ ID NO 304
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 304
cactctctcc attccctgcc a                    21

<210> SEQ ID NO 305
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 305
actctctcca ttccctgcca                      20

<210> SEQ ID NO 306
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 306
tcactctctc cattccctgc c                    21

<210> SEQ ID NO 307
<211> LENGTH: 21
<212> TYPE: DNA

```
<213> ORGANISM: Artificial Sequence
<220> FEATURE:
<223> OTHER INFORMATION: synthetic construct; antisense RNA

<400> SEQUENCE: 307
actctctcca ttccctgcca t                                              21

<210> SEQ ID NO 308
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 308
cactctctcc attccctgcc                                                20

<210> SEQ ID NO 309
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 309
aacataccac tccctcctg                                                 19

<210> SEQ ID NO 310
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 310
gtccatccaa cctgctccac a                                              21

<210> SEQ ID NO 311
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 311
gtccatccaa cctgctccac                                                20

<210> SEQ ID NO 312
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 312
tgtccatcca acctgctcca c                                              21

<210> SEQ ID NO 313
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 313
aaacatacca ctccctcct                                                 19
```

<210> SEQ ID NO 314
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 314
ctttccttcc ttctctccca c                                              21

<210> SEQ ID NO 315
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 315
ttccttcctt ctctcccaca                                                20

<210> SEQ ID NO 316
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 316
tccttccttc tctcccaca                                                 19

<210> SEQ ID NO 317
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 317
tcctttcctt ccttctctcc c                                              21

<210> SEQ ID NO 318
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 318
tttccttcct tctctcccac                                                20

<210> SEQ ID NO 319
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 319
tcccagctct gtggtcatca                                                20

<210> SEQ ID NO 320
<211> LENGTH: 21
<212> TYPE: DNA
<213> ORGANISM: Artificial Sequence
<220> FEATURE:

<223> OTHER INFORMATION: synthetic construct; antisense RNA

<400> SEQUENCE: 320
ttcccagctc tgtggtcatc a                                    21

<210> SEQ ID NO 321
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 321
tcgtcttgct tcttcatggt c                                    21

<210> SEQ ID NO 322
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 322
ttcccagctc tgtggtcatc                                      20

<210> SEQ ID NO 323
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 323
tcccagctct gtggtcatc                                       19

<210> SEQ ID NO 324
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 324
tcctagcctc ccgttgtctc t                                    21

<210> SEQ ID NO 325
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 325
cctcttccta gcctcccgtt                                      20

<210> SEQ ID NO 326
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 326
cctagcctcc cgttgtctct                                      20

```
<210> SEQ ID NO 327
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 327
ctcttcctag cctcccgttg t                                             21

<210> SEQ ID NO 328
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 328
tcctagcctc ccgttgtctc                                               20

<210> SEQ ID NO 329
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 329
gctttccctc tgtcatctcc t                                             21

<210> SEQ ID NO 330
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 330
gctttccctc tgtcatctcc                                               20

<210> SEQ ID NO 331
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 331
cgctttccct ctgtcatctc c                                             21

<210> SEQ ID NO 332
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 332
ccgccaatcc tatcccaca                                                19

<210> SEQ ID NO 333
<211> LENGTH: 20
<212> TYPE: DNA
<213> ORGANISM: Artificial Sequence
<220> FEATURE:
<223> OTHER INFORMATION: synthetic construct; antisense RNA
```

-continued

```
<400> SEQUENCE: 333
gccgccaatc ctatcccaca                                                  20

<210> SEQ ID NO 334
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 334
ccatctgtgc ttcctccca                                                   19

<210> SEQ ID NO 335
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 335
ccatctgtgc ttcctcccat                                                  20

<210> SEQ ID NO 336
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 336
accatctgtg cttcctccca                                                  20

<210> SEQ ID NO 337
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 337
ccatctgtgc ttcctcccat g                                                21

<210> SEQ ID NO 338
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 338
accatctgtg cttcctccc                                                   19

<210> SEQ ID NO 339
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 339
cttctgtctc tcccttgccc t                                                21

<210> SEQ ID NO 340
<211> LENGTH: 21
```

-continued

```
<212> TYPE: DNA
<213> ORGANISM: Artificial Sequence
<220> FEATURE:
<223> OTHER INFORMATION: synthetic construct; antisense RNA

<400> SEQUENCE: 340
tccttctgtc tctcccttgc c                                              21

<210> SEQ ID NO 341
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 341
ctccttctgt ctctcccttg                                                20

<210> SEQ ID NO 342
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 342
cttctgtctc tcccttgccc                                                20

<210> SEQ ID NO 343
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 343
ccttctgtct ctccttgcc                                                 19

<210> SEQ ID NO 344
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 344
gccctctttg aaatgaccc                                                 19

<210> SEQ ID NO 345
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 345
agccctcttt gaaatgaccc                                                20

<210> SEQ ID NO 346
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 346
```
ctgggtttca cagcctcat                                          19

<210> SEQ ID NO 347
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 347
ctctgggttt cacagcctca                                         20

<210> SEQ ID NO 348
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 348
ctgggtttca cagcctcata                                         20

<210> SEQ ID NO 349
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 349
gtccctgctg acaccaacca                                         20

<210> SEQ ID NO 350
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 350
gtccctgctg acaccaacca t                                       21

<210> SEQ ID NO 351
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 351
tccctgctga caccaaccat                                         20

<210> SEQ ID NO 352
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 352
tccctgctga caccaacca                                          19

<210> SEQ ID NO 353
<211> LENGTH: 21
<212> TYPE: DNA
<213> ORGANISM: Artificial Sequence

```
<220> FEATURE:
<223> OTHER INFORMATION: synthetic construct; antisense RNA

<400> SEQUENCE: 353
tccctgctga caccaaccat t                                              21

<210> SEQ ID NO 354
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 354
gctgccactc tcttccgttt                                                20

<210> SEQ ID NO 355
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 355
gctgccactc tcttccgtt                                                 19

<210> SEQ ID NO 356
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 356
gctgccactc tcttccgttt g                                              21

<210> SEQ ID NO 357
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 357
tgctgccact ctcttccgtt                                                20

<210> SEQ ID NO 358
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 358
tgctgccact ctcttccgt                                                 19

<210> SEQ ID NO 359
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 359
caccactctc agcccattcc                                                20
```

<210> SEQ ID NO 360
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 360
acaccactct cagcccattc c                                              21

<210> SEQ ID NO 361
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 361
caccactctc agcccattcc t                                              21

<210> SEQ ID NO 362
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 362
accactctca gcccattcct                                                20

<210> SEQ ID NO 363
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 363
accactctca gcccattcc                                                 19

<210> SEQ ID NO 364
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 364
tcccatccct cgtccttcag                                                20

<210> SEQ ID NO 365
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 365
tcccatccct cgtccttca                                                 19

<210> SEQ ID NO 366
<211> LENGTH: 20
<212> TYPE: DNA
<213> ORGANISM: Artificial Sequence
<220> FEATURE:
<223> OTHER INFORMATION: synthetic construct; antisense RNA

<400> SEQUENCE: 366
atcccatccc tcgtccttca                                           20

<210> SEQ ID NO 367
<211> LENGTH: 21
<212> TYPE: DNA
<213> ORGANISM: Artificial Sequence
<220> FEATURE:
<223> OTHER INFORMATION: synthetic construct; antisense RNA

<400> SEQUENCE: 367
atcccatccc tcgtccttca g                                         21

<210> SEQ ID NO 368
<211> LENGTH: 19
<212> TYPE: DNA
<213> ORGANISM: Artificial Sequence
<220> FEATURE:
<223> OTHER INFORMATION: synthetic construct; antisense RNA

<400> SEQUENCE: 368
atcccatccc tcgtccttc                                            19

<210> SEQ ID NO 369
<211> LENGTH: 1712
<212> TYPE: DNA
<213> ORGANISM: Homo sapiens

<400> SEQUENCE: 369
aagggcggga cattcccct gcctcttcgc accacagcca gagcctgcca ttaggaccaa      60
tgaaagcaaa gtacctcatc ccctcagtga ctaagaatcg cagtatttaa gaggtagcag    120
gaatgggctg agagtggtgt tgctttctc caccagaagg gcacactttc atctaatttg    180
gggtatcact gagctgaaga caaagagaag ggggagaaaa cctagcagac caccatgtgc    240
tatgggaagt gtgcacgatg catcggacat tctctggtgg ggctcgccct cctgtgcatc    300
gcggctaata ttttgcttta ctttcccaat ggggaaacaa agtatgcctc cgaaaaccac    360
ctcagccgct tcgtgtggtt cttttctggc atcgtaggag gtggcctgct gatgctcctg    420
ccagcatttg tcttcattgg gctggaacag gatgactgct gtggctgctg tggccatgaa    480
aactgtggca aacgatgtgc gatgctttct tctgtattgg ctgctctcat ggaattgca    540 ggatctggct actgtgtcat tgtggcagcc cttggcttag cagaaggacc actatgtctt    600
gattccctcg gccagtggaa ctacaccttt gccagcactg agggcagta ccttctggat    660 acctccacat ggtccgagtg cactgaaccc aagcacattg tggaatggaa tgtatctctg    720
ttttctatcc tcttggctct tggtggaatt gaattcatct tgtgtcttat tcaagtaata    780
aatggagtgc ttggaggcat atgtggcttt tgctgctctc accaacagca atatgactgc    840
taaaagaacc aacccaggac agagccacaa tcttcctcta tttcattgta atttatatat    900
ttcacttgta ttcatttgta aaactttgta ttagtgtaac atactcccca cagtctactt    960
ttacaaacgc ctgtaaagac tggcatcttc acaggatgtc agtgtttaaa tttagtaaac   1020 ttctttttg tttgtttatt tgtttttgtt ttttttaag gaatgaggaa acaaaccacc   1080
ctctgggggt aatttacaga ctgagtgaca gtactcagta tatctgagat aaactctata   1140
atgttttgga taaaataac attccaatca ctattgtata tatgtgcatg tattttttaa   1200
attaaagatg tctagttgct ttttataaga ccaagaagga gaaaatccga caacctggaa   1260

| | |
|---|---:|
| agattttttgt tttcactgct tgtatgatgt ttcccattca tacacctata aatctctaac | 1320 |
| aagaggccct ttgaactgcc ttgtgttctg tgagaaacaa atatttactt agagtggaag | 1380 |
| gactgattga gaatgttcca atccaaatga atgcatcaca acttacaatg ctgctcattg | 1440 |
| ttgtgagtac tatgagattc aaattttttct aacatatgga aagccttttg tcctccaaag | 1500 |
| atgagtacta gggatcatgt gtttaaaaaa agaaaggcta cgatgactgg gcaagaagaa | 1560 |
| agatgggaaa ctgaataaag cagttgatca gcatcattgg aacatgggga cgagtgacgg | 1620 |
| caggaggacc acgaggaaat accctcaaaa ctaacttgtt tacaacaaaa taaagtattc | 1680 |
| actaccatgt taaaaaaaaa aaaaaaaaaa aa | 1712 |

<210> SEQ ID NO 370
<211> LENGTH: 2860
<212> TYPE: DNA
<213> ORGANISM: Homo sapiens

<400> SEQUENCE: 370

| | |
|---|---:|
| gccatcttgc gtacggaggt gaggtttgtt accgcgattc tgagaggtgg gcttttagtc | 60 |
| cctccagacc tcggctttag tgctgtctcc gcttttcttt caccttcaca gaggttcgtg | 120 |
| tcttcctaaa agaaggttttt attgggaggt aaaggtcaat gcgtaggggt agagtaagat | 180 |
| gtcttatggt gaaattgaag gtaaattctt gggacctaga aagaagtaa cgagtgagcc | 240 |
| acgctgtaaa aaattgaagt caaccacaga gtcgtatgtt tttcacaatc atagtaatgc | 300 |
| tgattttcac agaatccaag agaaaactgg aaatgattgg gtccctgtga ccatcattga | 360 |
| tgtcagagga catagttatt tgcaggagaa caaaatcaaa actacagatt tgcatagacc | 420 |
| tttgcatgat gagatgcctg gtaatagacc agatgttatt gaatccattg attcacaggt | 480 |
| tttacaggaa gcacgtcctc cattagtatc cgcagacgat gagatatata gcacaagtaa | 540 |
| agcatttata ggacccattt acaaaccccc tgagaaaaag aaacgtaatg aagggaggaa | 600 |
| tgaggcacat gttctaaatg gtataaatga cagaggagga caaaagaga aacagaaatt | 660 |
| taactctgaa aaatcagaga ttgacaatga attattccag ttttacaaag aaattgaaga | 720 |
| gcttgaaaag gaaaaagatg gttttgagaa cagttgtaaa gaatctgaac cttctcagga | 780 |
| acaatttgtt ccatttttatg agggtcataa taatggtctc ttaaaacctg atgaagaaaa | 840 |
| gaaagatctt agtaataaag ctatgccatc acattgtgat tatcagcaga acttggggaa | 900 |
| tgagccagac aaatatccct gtaatggaca agtaatacct acattttgtg cacttcatt | 960 |
| tacttctttc aggcctgaat ggcagtcagt atatcctttt atagtgccct atggtccccc | 1020 |
| tcttcccagt ttgaactatc atttaaacat tcagagattc agtggtccac caaatccacc | 1080 |
| atcaaatatt ttccaagccc aagatgactc tcagatacaa aatggatatt atgtaaataa | 1140 |
| ttgtcatgtt aactggaatt gcatgacttt tgatcagaac aatgaatata ctgactgtag | 1200 |
| tgagaatagg agtagtgttc atccctctgg aaatggctgc agtatgcaag atcgatatgt | 1260 |
| gagtaatggt ttctgtgaag tcagagaaag atgctgaaaa gatcattgta tggacaagca | 1320 |
| taatggaaca gacaggtttg tgaaccagca gtttcaagag gaaaagttaa ataaattgca | 1380 |
| gaagttactt attcttttaa gaggtctgcc tggttctggg aaaacaacat tgtctcgaat | 1440 |
| tctgcttggt cagaatcgtg atggcattgt gttcagcact gatgactatt ttcaccatca | 1500 |
| agatgggtac aggtataatg ttaatcaact tggtgatgcc catgactgga accagaacag | 1560 |
| agcaaaacaa gctatcgatc agggaagatc tccagttata atagataaca ctaatatacag | 1620 |
| agcttgggaa atgaagccat atgtggaagt ggccatagga aaaggataca gagtagagtt | 1680 |

```
tcatgaacct gaaacttggt ggaaatttga tcctgaagaa ttagaaaaga ggaataaaca   1740
tggtgtgtct cgaaagaaga ttgctcagat gttggatcgt tatgaatatc aaatgtccat   1800
ttctattgta atgaattcag tggaaccatc acacaaaagc acacaaagac ctcctcctcc   1860
acaggggaga cagaggtggg gaggctctct tggctcacat aatcgtgtct gtgtcacaaa   1920
taatcattaa attagctatt ttcagctaac acatttgttg ttgcacttga aaaagagtta   1980
gtgagcctgt cttggagttt aagtagtttc aaataaaaaa aggctacagt gcctcacaaa   2040
ggatgttccc agcaagttgt ttaaattccc agcaagttgt taaagtgtaa ataaaaatat   2100
atgaaattgt atttttaaatg ttttatatt ctcttgttgt aatactcttg ctgttatgg    2160 aagcacctga gtaatagagt ggtgggtagg agctaggatg ttttctaca atcgaatttt   2220 aaactaattt atctattta tagacactat tgaacagttt tttaatagtt catatctaaa    2280
tctaactttt cataaaactt tacggttttt ccttcactac cttaaatatg caagaaatac   2340
tgacttggta tagggtacct tagttttctc tattcattag acaggtaaaa ttatatttca   2400
gctgattgat ctgtgtgaca aaattatttc ttagctataa tcagcacatc acttagttca   2460
aacaaaattc cccagcaaat gttagatagt aggtatatca gtcacctggg gagttttctt   2520
cataatatgc atattcatct tgtaatgcat acatagttat catcctcctt ctcaacccat   2580
ctccctaacc ccacatgctt gccagttctt gaagggataa agtgattcta ataatgtttt   2640
acttctctct gttcaattta atgtgatata attctagtat aaaaatattt tggacagttg   2700
cttaacatgg tcataagagg atttgtacta tagaatatct tctagtacta atttttctgt   2760
agagcaaatt atatttctct cactggatag tttttagatg tgtttcttca tataaaatta   2820
aaaactgaga tggaattcaa aaaaaaaaaa aaaaaaaaa                          2860
```

<210> SEQ ID NO 371
<211> LENGTH: 2280
<212> TYPE: DNA
<213> ORGANISM: Homo sapiens

<400> SEQUENCE: 371

```
gtgcgggttt cggttggagg actcgttggg gaggtggcct gcgcttgtag agactgcatc     60
cccgagacga tggcggaggg agataatcgc agcaccaacc tgctggctgc agagactgca   120
agtctggaag aacagctgca aggatgggga gaagtgatgc tgatggctga taagtcctc    180 cgatgggaaa gagcctggtt tccacctgcc atcatgggtg tggtttcttt ggtgtttctg   240
attatctact atctagatcc atctgttctg tccggcgttt cctgttttgt tatgtttttg   300
tgcttggctg actaccttgt tcccattcta gcgcctagaa ttttggctc caataaatgg    360 accactgaac aacagcaaag attccatgaa atttgcagca atctagtaaa aactcgacgc   420
agagctgtgg gttggtggaa acgcctcttc acactaaagg aagaaaaacc taagatgtac   480
ttcatgacca tgatcgtttc ccttgctgcg gttgcttggg tgggacaaca agtccacaac   540
ctgcttctca cctacctgat agtgacttcc ttactattgc ttcctggact aaaccaacat   600
ggaatcattt tgaagtacat tggaatggcc aagagggaga taaacaaact tctcaaacaa   660
aaagaaaaga aaaacgaatg attcatctgc tttaatcagt gtgattaatg cagcaccaat   720
tgccccggga accgtttctg ctgtactatc tggatactaa aatgttacgg aagtagctct   780
ttgttctccc tcactctgcc cttagttaat agaaattcag actcgccaag taaggcttcg    840
tgcatagtgt cttcatgtcg cgtatagttg agcgcgttct tagcagttgg cttcatggac    900
```

```
aactcattag tgttttgact tttcttaccc agcgttaatt gaattcttgc ttttagacaa      960
cttccttttt gtagtggtga accttgccct ttagtacagt tcaagtgaat ctggataatt     1020
gttcatcttt gctttagctt agataccatg tagtggtctg tggctacagg aagctggttc     1080
tgtctgcttc cacagtctgc ttaaaaaact gtctgacttc gtgaatatag agaccaagtt     1140
taccacttct gatgaagaga ccaattaaga ttcattcctc attctgtttc tttccagtgg     1200
gagaagagtc cccatgaaat aagatgaaac tgattccatg cactagtaca tgtaggcttc     1260
tcccttgtgc aaagcttagc aatttgtagg aaactttgat cttttttgtcc aagaaaagga    1320 atgtctgaca ggcttaagct ttcgtcccct tgcacttaga ctcgaagtta gtaaatcctt     1380
aaaggctttt taatagcaga cttccaaaag attgcattta ggatttctag catgcttta     1440 atttcagatt ttcagctgac attagctata gtatacagta ggttaagact catgtctatg     1500
actttcactc taagactggc aaaaggacag cagtcttcta tgtttagtca atattcattt     1560
cagtagaaga taatcttatc taattttttga gaccagaata agccttttaa ggtaaacctc     1620
aaaattatca ttttatggta atactgacca ttttagtccc ctaggtttga catgggagat     1680
agtgactaca ctggtgtctg acttttttcc tagagatttc tccctgaaaa atacaagggc     1740
tgttggtgag agcagacttg aggtgatgat agttggcctc tggtctacaa agatttcata     1800
actccttgga aagcttctta taatcattct taacttcttg gtagctagaa atttagagta     1860
gttgaaatct ttaggaatga acttctgagg gccaaaaaat gtgactgacg ggaacaattc     1920
ttaaactgat taactagctg taatatagtt ttgtgaattt attgcactga tgttgtacct     1980
tgtggtatat ctgtccctat taaataagtg ttgttttctc ctctttaata ttgctgtgaa     2040
cagtggtgcc cattgtagca tatgtttgat tttttttat tatttcataa gaaaactacg      2100
ttaattttac cttactttca ttgtaaataa gcctgtcttc ctatctggat tttttgtgtg     2160
catacatatt ctactgatta actacttttg cagttttaat cctgtattat ttcttctact     2220
ttgttttgtg taaagggga aaaataaaa aaagctggaa tcttaaaaaa aaaaaaaaaa        2280
```

<210> SEQ ID NO 372
<211> LENGTH: 4269
<212> TYPE: DNA
<213> ORGANISM: Homo sapiens

<400> SEQUENCE: 372

```
agatgtcgct cccggaagtg ttgggcgcag ggcgtggctg cggctgcggc tgccacgttg       60
gaacggaacg tggaggtggc cctggccggg gaggaggggc ggcggcgaat gctgggagag      120
tccgacgagc gctgcactaa cgcaggatcc ggctgccgaa ggtcctcgcc agcaggatga      180
agttaaagga agtagatcgt acagccatgc aggcatggag ccctgcccag aatcaccccca     240 tttacctagc aacaggaaca tctgctcagc aattggatgc aacatttagt acgaatgctt     300
cccttgagat atttgaatta gacctctctg atccatcctt ggatatgaaa tcttgtgcca     360
cattctcctc ttctcacagg taccacaagt tgatttgggg gccttataaa atggattcca     420
aaggagatgt ctctggagtt ctgattgcag gtggtgaaaa tggaaatatt attctctatg     480
atccttctaa aattatagct ggagacaagg aagttgtgat tgcccagaat gacaagcata     540
ctggcccagt gagagccttg gatgtgaaca ttttccagac taatctggta gcttctggtg     600
ctaatgaatc tgaaatctac atatgggatc taaataattt tgcaaccccca atgacaccag     660 gagccaaaac acagccgcca gaagatatca gctgcattgc atggaacaga caagttcagc     720
atattttagc atcagccagt cccagtggcc gggccactgt atgggatctt agaaaaaatg     780
```

```
agccaatcat caaagtcagt gaccatagta acagaatgca ttgttctggg ttggcatggc    840
atcctgatgt tgctactcag atggtccttg cctccgagga tgaccggtta ccagtgatcc    900
agatgtggga tcttcgattt gcttcctctc cacttcgtgt cctggaaaac catgccaggg    960
ggattttggc aattgcttgg agcatggcag atcctgaatt gttactgagc tgtggaaaag   1020
atgctaagat tctctgctcc aatccaaaca caggagaggt gttatatgaa cttcccacca   1080
acacacagtg gtgcttcgat attcagtggt gtccccgaaa tcctgctgtc ttatcagctg   1140
cttcgtttga tgggcgtatc agtgtttatt ctatcatggg aggaagcaca gatggtttaa   1200
gacagaaaca agttgacaag ctttcatcat cttttgggaa tcttgatccc tttggcacag   1260
gacagcccct tcctccgtta caaattccac agcagactgc tcagcatagt atagtgctgc   1320
ctctgaagaa gccgcccaag tggattcgaa ggcctgttgg tgcttctttt tcatttggag   1380
gcaaactggt tacgtttgag aatgtcagaa tgccttctca tcagggagct gagcagcagc   1440
agcagcagca ccatgtgttc attagtcagg ttgtaacaga aaaggagttc ctcagccgat   1500
cagaccaact tcagcaggct gtgcagtcac aaggatttat caattattgc caaaaaaaaa   1560
ttgatgcttc tcagactgaa tttgagaaaa atgtgtggtc cttttttgaag gtaaactttg   1620
aggatgattc tcgtggaaaa taccttgaac ttctaggata cagaaaagaa gatctaggaa   1680
agaagattgc tttggccttg aacaaagtgg atggagccaa tgtggctctt aaagactctg   1740
accaagtagc acagagtgat ggggaggaga gccctgctgc tgaagagcag ctcttgggag   1800
agcacattaa agaggaaaaa gaagaatctg aatttctacc ctcatctgga ggaacattta   1860
atatctctgt cagtggggac attgatggtt taattactca ggctttgctg acgggcaatt   1920
ttgagagtgc tgttgacctt tgtttacatg ataaccgcat ggccgatgcc attatattgg   1980
ccatagcagg tggacaagaa ctcttggctc gaacccagaa aaaatacttc gcaaaatccc   2040
aaagcaaaat taccaggctc atcactgcag tggtgatgaa gaactggaaa gagattgttg   2100
agtcttgtga tcttaaaaat tggagagagg ctttagctgc agtattgact tatgcaaagc   2160
cggatgaatt ttcagccctt tgtgatcttt tgggaaccag gcttgaaaat gaaggagata   2220
gcctcctgca gactcaagca tgtctctgct atatttgtgc agggaatgta gagaaattag   2280
ttgcatgttg gactaaagct caagatggaa gccacccttt gtcacttcag gatctgattg   2340
agaaagttgt catcctgcga aaagctgtgc aactcactca agccatggac actagtactg   2400
taggagttct cttggctgcg aagatgagtc agtatgccaa tttgttggca gctcagggca   2460
gtattgctgc agccttggct tttcttcctg acaacaccaa ccagccaaat atcatgcagc   2520
ttcgtgacag actttgtaga gcacaaggag agcctgtagc aggacatgaa tcacctaaaa   2580
ttccgtacga gaaacagcag ctccccaagg gcaggcctgg accagttgct ggccaccacc   2640
agatgccaag agttcaaact caacaatatt atccccatgg agaaaatcct ccacctccgg   2700
gtttcataat gcatggaaat gttaatccaa atgctgctgg tcagcttccc acatctccag   2760
gtcatatgca cacccaggta ccaccttatc cacagccaca gccttatcaa ccagcccagc   2820
cgtatccctt cggaacaggg gggtcagcaa tgtatcgacc tcagcagcct gttgctcctc   2880
ctacttcaaa cgcttaccct aacaccccctt acatatcttc tgcttcttcc tatactgggc   2940
agtctcagct gtacgcagca cagcaccagg cctcttcacc tacctccagc cctgctactt   3000
ctttccctcc tccccttcc tctggagcat ccttccagca tggcgaccca ggagctccac   3060
catcatcttc agcttatgca ctgcctcctg gaacaacagg tacactgcct gctgccagtg   3120
```

-continued

| | |
|---|---|
| agctgcctgc gtcccaaaga acaggtcctc agaatggttg gaatgaccct ccagctttga | 3180 |
| acagagtacc caaaaagaag aagatgcctg aaaacttcat gcctcctgtt cccatcacat | 3240 |
| caccaatcat gaacccgttg ggtgacccca gtcacaaat gctgcagcaa cagccttcag | 3300 |
| ctccagtacc actgtcaagc cagtcttcat tcccacagcc acatcttcca ggtggccagc | 3360 |
| ccttccatgg cgtacagcaa cctcttggtc aaacaggcat gccaccatct tttcaaagc | 3420 |
| ccaatattga aggtgcccca ggggctccta ttggaaatac cttccagcat gtgcagtctt | 3480 |
| tgccaacaaa aaaattacc aagaaaccta ttccagatga gcacctcatt ctaaagacca | 3540 |
| catttgagga tcttattcag cgctgccttt cttcagcaac agaccctcaa accaagagga | 3600 |
| agctagatga tgccagcaaa cgtttggagt ttctgtatga taaacttagg gaacagacac | 3660 |
| tttcaccaac aatcaccagt ggtttacaca acattgcaag gagcattgaa actcgaaact | 3720 |
| actcagaagg attgaccatg catacccaca tagttagcac cagcaacttc agtgagacct | 3780 |
| ctgctttcat gccagttctc aaagttgttc tcacccaggc caataagctg ggtgtctaaa | 3840 |
| aggacagctt ctcttccact caatattgcc atttttccaa agaaacatgt taaaaaaaaa | 3900 |
| aattataaga catggactag tcctcattag catgtttgca tagcaaccag tcaagagcat | 3960 |
| ttacactatt tctgctgata tactcacctt agaactgctc agaaccctgg tgctttattt | 4020 |
| ttgttttaat cttttgttgc cagtgatgat tttcctattc tgcaaatagt gtatttcctg | 4080 |
| gattacacat agtatggttt cctgaagtat tctgataaat gtgttttta aaccctcaat | 4140 |
| atactttta gaaaggagc atctggttat gcataaagca gagctaaaac taaatttctt | 4200 |
| tcatgtcctc cctacttcct cagtgtcaat cagattaaag tgtgtaatcc taaaaaaaaa | 4260 |
| aaaaaaaaa | 4269 |

<210> SEQ ID NO 373
<211> LENGTH: 7019
<212> TYPE: DNA
<213> ORGANISM: Homo sapiens

<400> SEQUENCE: 373

| | |
|---|---|
| gggccggggg gcgatggaat aaagaagat ggagagactt cagcgcctgg gactcgggtg | 60 |
| ggcgaggcgg aaggtgtcct cgcagcacgg cttttctccg cgccgcggtt ggttagcgag | 120 |
| tgccctctgg gtgctaggcg ttgggcggat ggtaggatcg cggtagcata cggatccgag | 180 |
| tcctgcgccg agtgagagga gaggctggca ggggctaagt gatggatctt gtactccgtg | 240 |
| ttgcagatta ctattttttt acaccatacg tgtatccagc cacatggcca gaagatgaca | 300 |
| tcttccgaca agctattagt cttctgattg taacaaatgt tggtgcttac atcctttatt | 360 |
| tcttctgtgc aacactgagc tattattttg tcttcgatca tgcattaatg aaacatccac | 420 |
| aatttttaaa gaatcaagtc cgtcgagaga ttaagtttac tgtccaggca ttgccatgga | 480 |
| taagtattct tactgttgca ctgttcttgc tggagataag aggttacagc aaattacatg | 540 |
| atgacctagg agagtttcca tatggattgt ttgaacttgt cgttagtata atatctttcc | 600 |
| tcttttttcac tgacatgttc atctactgga ttcacagagg ccttcatcat agactggtat | 660 |
| ataagcgcct acataaacct caccatattt ggaagattcc tactccattt gcaagtcatg | 720 |
| cttttcaccc tattgatggc tttcttcaga gtctacctta ccatatatac ccttttatct | 780 |
| ttccattaca caaggtggtt tatttaagtc tgtacatctt ggttaatatc tggacaattt | 840 |
| ccattcatga cggtgatttt cgtgtccccc aaatcttaca gccatttatt aatggctcag | 900 |
| ctcatcatac agaccaccat atgttctttg actataatta tggacaatat ttcactttgt | 960 |

-continued

```
gggataggat tggcggctca ttcaaaaatc cttcatcctt tgaggggaag ggaccgctca   1020
gttatgtgaa ggagatgaca gagggaaagc gcagcagcca ttcaggaaat ggctgtaaga   1080
atgaaaaatt attcaatgga gagtttacaa agactgaata gattattgcc cagttattct   1140
taagtaagga caaagaagga aatatcatcg tatttctttt ttttaataag gaaaaaataa   1200
tatccataca gtcaagatac atagtaaatg gtatcatttg gaaatcagca tcgtgggcac   1260
tgctgaggaa tgatcctagt ggtaggtcag aagaagatgc tgtgaacacc aggactttaa   1320
tcttatgctt aaaatgccag atgttgttcg ggggacaact tgtatctttc tagcagcaga   1380
tctgtagttt gtatagcctc aacaacaatt ttaaataaga tggagaataa attattgagg   1440
ggactaggct atatgcattt gccttcatcc acccatgttt attaagaatc attgtgctta   1500
ataataccaa gactaagcac cataaccaag aaatactaat gtaaagattg tttcttgttt   1560
caggaatggt taattcttca acgttggtat gataatgata acttgttttg acttgaataa   1620
agtactacat cagtgtggaa aaaaattctg atacattagc agctatgtaa atgacctaat   1680
tgatagcagg tgtaataaga ctatcgtctt cctacacata ggaggctcat tctctggaca   1740
cactatcacc tattcatttt tactgattaa caaataaatt ggaatttaaa aatatcgata   1800
tcaccatgat ttaatccaga tctgggatta tgtagctaaa cattgtgatg attattattt   1860
aaaaccatta tttaataaga gtaaaaatat gtgaatctgg atatatttaa aaaagaaat   1920 ttgatgccca gataatatat taggcactac tgattttttta gttaaattga tgcactacac   1980
ttttgatgtt tgaagttaca aacctgtaat ttttttgtaa aggaaataat tgccaaatac   2040
ctaggcccat tgctgacgat tagttctaaa atcttattcc tcctcttctc ccctcacttt   2100
tccctacttc ctctgcaaaa agatttaaca aatacattca taaggaaatg tgtgttgtaa   2160
caaatatatt gcaaaaacat agtttgtaaa ggcattctat aagctattta tgtaaaatca   2220 ataaagttg atcataatta aactgtatca gttgagtatt atagcagcac aaagtattct   2280
ttgtacagat tttgtgccaa tttgaagcca cagaaatgat gtggattgtt aattgtgttt   2340
tagaacatcc ccggacactc agtgtcacag ggggaaagaa gtgggtacca cattctgttt   2400
atatttcaca ttttaactag atttgagtgt ttttagcaag aaatcagtct taaaatctaa   2460
tgtctgggat ccagaagaaa atgtctttaa tctgtgagtt attgtcacaa tgtcatctta   2520
tttaaatgta ccaattagca ttttgtaata ggcaaatgtc atttagtgct tttcaccaat   2580
cccactcacc cccggtgctc cgccttgcct aagaaaaaga aattaaggag aagtaaactt   2640
tatttcctaa tataatgtca gctgatattt attgagcttt tcctctttgc ccagagacta   2700
ggacccaaag aagttaagta actattccca ggtttatttc tctctcatat gatgtcccat   2760
gtggatgttt gtggtcagtg gacagctttc cacctagtct ttctgcgacc caggctcctt   2820
cctcttgggg ctctgccttt ctctcagtcc atagagccct cttgttgaa agagcacata   2880 ggaaaagaag gaaagtctg tgtggaaaat gtttctgggt caggcctgga agtggtgcat   2940
atctcttccg cccatgttcc tttggacaga actccgtcac atggcccacc tagagagatt   3000
ttgggaaatg tgtccagctg tgtgcctggg aggaaggggg caccatttc ttgagcagct   3060 agacagtttg ccgtatttgt ggtgttctcc tcttgttgat gttgaaatgg tgaatgagcc   3120
ataaagtatt tcaggttatc cacacactaa tcatctcagt gtctttaatt cttaactcca   3180
atatgaatgt ttaaagcttc ctctagattc ttattcctat ataactaata gagaagaaag   3240
gacagcttcc tatggggaag acagaggctt cctcatagat gttaggaata atcaaacttg   3300
```

-continued

```
cccctgccct ttcacccgtc tcaaattctg gtcttttaaa gcagcgttat gttaagtagt      3360
cctaacattg taatatacag tactgccaca ttctcctact ttctattaga ggaagtcaga      3420
gaatatttat ggaagtgagg acccaaatta ccttctacag atgactttta tagttacagg      3480
acagaaagtg aaaatcaagg ttacgttttc tacttttgtg gtagaaattg agaagtgggt     3540
ggatatggtt cgagaagacc tttcagaaac acagagactg agtctttgtc ttccatgctg      3600
tctctgcagt actgagtgaa tttccttata cccttgtatc atgttttcct cccatcttct      3660
agaagctggg gacagatttg aagagaatt acacaagttc agttttttga tacatggatt      3720
ttacagtgca tgcaggttat ttatgtagag aggaggtctg ggagaaagat ggaaactagg      3780
gagatgactg agaacaaaga tatttgggat taacacagat agaagaaaag tttgaaacca     3840
tgagattgtc acagcatgaa aaagatatt caaagacact aaccaacttg aggggtgcag      3900
tggtctgaat gtgtcctcca aaattcaaat gtggaaatgt atttgccagt gagatagtat     3960
gtagaggtgg ggccttgagg aagtgattaa gtcatgaggg ctctgggatt aatgacttaa     4020
aaagaggtgt gaggcagctg ttcagccctt ctgtctcctg tcccttttt tttttttttt       4080
tttgagatgg agtcttgctc tgttgcccca ggctggagtg cagtggcgtg atcttggttc     4140
actgcaagct ccacctcccg ggttcacgcc attctcctgc ctcagcctcc cgagtagctg      4200
ggactacagg tgcccgccac caccacgccc ggctaatttt ttatattttt agtagagatg     4260
gggtttcacc gtgttagcca ggatggtctt gatctcctga cctcatgatc tgcctgcctc     4320
ggcctcccaa agtgctggga ttataggtgt gagccaccat gcccagcccc ttctgtccct     4380
tctaacgtga ggacccagca acaaggtacc atcttgaaag cagcaactgg ggactcagca    4440
gacaccaaac caactggtgc ttaaccgtga cttcccagcc tccagagctg taagaaaata    4500
aatttctatt atttatagat tacccagttg aagatacttt gttaaggcag tacaaatgga     4560
ctaagacaag ggggaagaaa tttgcattcc tgatcttccc aacttcttca aattcacaac    4620
acttgaatga cagtcttatt tcagcactta ctgctatcac ctattacttt tatgtgtgtc     4680
ttacctattt gagatgccag attccttgga agtagagacc gtgtctgaat catcattgta    4740
ttaaaccact catccttaac aaatgcccaa gccatggtta aagttcaata aatactttgt   4800
tgaatttatt aataaaatgg cagaaatgtc attctcttcc atatatgttt aataaatccc      4860
tgataggtgc taagcactgc actaggtaaa aattctcttc tgatgctgtc ttttttggcca   4920
accatttttt tatcatttat tcattagctg acatttgcta agtgctttgg aggggtcaaa    4980
aggggaagta atgagaaatc aaagatggtc cctacatcaa ggataaacta tcttttttta    5040
gtcactcaaa gtcataaccc tttggaaaca aaacccacca gtaccccaga ttttgaccac   5100
agatgaatca gtactacaag gactggttag agggttgaat gaatctgtat actcagcact   5160
taacacagca ctctgggtaa aagaaaaaag atcctcaaag atattagttg gttacatcaa   5220
gaaaggacaa acttaggtta atctataact tcatctcaga ggaacaggaa ctttggagat    5280
aaacagggct ctgccacttg caagttgcac catccctggt ttctccatct gtaaattgat    5340
taaaacactg cctatctaat aagattaaat aagttagaag cattcagtta aatgtcaact   5400
gaaactattg ttcatgtaaa ttgtgcttga tgcttttct ttctagattc aatgattatt     5460
gtcatttac ctccataggc cctcaataga aatcagttgc agagggcaga agcctagata    5520
ttttcacctt aaaattggag ggtgaaagac attgaggtga agtagagata gagggtacac   5580
agaaaaatcg tataagtaaa actaacatcg ttaacattat ttactgtaag ttatctttgt   5640
aagagtggta aaatacattg tgttgttaaa taatttcatt taaaaaatgc atcactttgt   5700
```

```
gtgttttat attgctaaaa ccataaggcc agtctacaag gtttgtagat aaaatagaaa     5760 catacccttcc ttgaaaagca gaataaattt tttaaaggca ggaaggaagt gtttgaacca    5820
tgtgtcaaca agctttactg tcaaagcagg cttttggtat gggaagaaaa atacttataa    5880
atacttgttt taatatttgc tttattaaaa tacatttaaa atacagcatt tttaaatctc    5940
taagctcaac ttgaagatat aagaacagta aatttgataa aaatgagaaa ttacattccc    6000
atttctttaa caatttgtaa attccaatta tcctgaacat ttaataccat ttacatattt    6060
tattaatcac attttcttaa acatttgata agagatttaa tattttgatc caactaccaa    6120
aaaagcagac ttgtgtactt gacagatttt tctaaacact tcacaactca cgattcaaac    6180
aaagacaaaa tagcatatca aaagttaatc actcagttgg aaagcactca taccataggc    6240
ttttattcat ttcttgaata attttgttat atcttcctct tttaggctgc aatgagctat    6300
aattgcacta ctgcactcca cgctgggtga cagagcaaga ccctatctct aaaaataaaa    6360
aagtatatat atataaaaat atcttcctct attataattt aactcattaa gccatttatt    6420
tagatgtaaa cttgcccccc tgacatgtgg tatgaaacaa atagaaacct agaaatttag    6480
tgcatattca aatattaaga cagacactgg tgtggtgact tttgtctgtc gcttcattgg    6540 gacgttttt ctttctgatc aacttaatga aattataatt tactataatt aagtgtagcc    6600
atttttactg tagagttcaa tgatctttga tgaacgtgta cacccatgta accaccaccc    6660
ccaatcaaag taagaacat tttcttacca gaataaattt cctctccgtt tgcagtcatt     6720
ctccccagcc ctaggtcacc actgatccac cttctgttac tggaaggtta gttttcttcc    6780
ctgatttaga atttcatata aattaaatca gatagtatat actcttgtgt ttagtttctt    6840
tagcttaaca tgtttagaga tatttgctgt tgcctgtgtc tgtagctttt tgttttcatt    6900
gctgaatagt atttcattgt aatataccac agttggttta tgtatttgct gatgaatatt    6960
tgtgttattt ccagcgtggg attattatga ataaagttgc tacaaacatt tgtatacaa     7019

<210> SEQ ID NO 374
<211> LENGTH: 6578
<212> TYPE: DNA
<213> ORGANISM: Homo sapiens

<400> SEQUENCE: 374
ctcagtggcg gagcgcggct gccggtgtgc ggccgggagc gatcgccgcg gggcaggggc      60
gcggcgggca ccgcgcagag cgcgcagaac agacggacgg cggcggggac ccgacggcgg    120
cgcctcggca ctccccagac tccggccagc gccccctgc cagccgcaag cacccagccc     180
cggcccaccc cgggctctcg atggcccccg aggccggggc gaccctgcgc gcgccgcgcc    240
ggctgtcctg ggcggcgctg ctgctcttgg ccgcgctgct cccgtcgcc tcctcggcgg     300 cggcctcagt tgaccaccca ctgaagccaa ggcatgtgaa actgctgtcc actaaaatgg    360
gcctgaaagt cacgtgggac ccacccaaag atgctaccag tagacctgtg agcattaca    420 acattgccta tgggaagtca ctgaaaagtc ttaaatacat caaggtgaat gcggagacat    480
actccttcct tattgaggat gtggagccgg gggtagtgta ctttgtgctg cttactgcag    540
aaaaccacag tggagtgagc cgtcctgttt acagagctga aagcccacct ggaggtgaat    600
ggatcgagat tgatggtttt cccattaagg gtccaggacc atttaatgaa accgtcacag    660
aaaaggaagt gccaacaag cccttgcgtg tgcgtgtccg gtcctcagat acaggctgt      720 ccgttgcgtg gaaggcacca cgcctgtctg agccaagag tccacgcaga tcacgggtt      780
```

```
ttctcctggg ctacggggag agtggccgga agatgaatta tgttccactg acaagagatg    840
aacggacaca cgaaattaaa aagctagcct cggaatccgt gtatgtggtc tccctgcagt    900
ccatgaactc tcagggccgg agccaaccag tctacagggc tgccctaaca aagcgaaaga    960
tttcagaaga ggacgaattg gatgtacctg acgacatcag cgtccgggtt atgtcatctc   1020
agtctgtgct tgtgtcctgg gtggatcctg ttctggaaaa acagaagaaa gttgttgcat   1080
caagacagta caccgtgcgc tatcgagaga ggggggaatt ggccaggtgg gattataagc   1140
agatcgctaa caggcgtgtg ctgattgaga acctgattcc agacactgtg tatgaatttg   1200
cagtccgtat ttcacagggt gaaagagatg gcaaatggag tacgtcagtc ttccaaagaa   1260
caccagaatc tgcccctacc acagctcctg aaaacttgaa cgtctggcca gtcaatggca   1320
aacctacagt tgtcgctgca tcttgggatg cgctaccaga gactgagggg aaagtgaaag   1380
aatacattct ttcatacgcc ccggctctca accatttgg agcaaagtcc ctcacctatc    1440
ctggagacac tacttctgcc ctggtggatg gtctgcagcc tggggaacgc tatcttttca   1500
aaatccgggc cacaaacagg agaggcctgg gacctcactc caaagccttc attgtcgcta   1560
tgccaacaac cagtaaggcg gatgttgagc agaacacgga ggacaatggg aaacccgaaa   1620
aacctgagcc ttcctcacct tctcccagag ctccagcttc ctcccaacac ccctctgtgc   1680
ctgcttctcc ccaagggaga aatgccaagg accttcttct tgacttgaag aacaaaatat   1740
tggctaatgg tggggcgccc cgaaaacccc agcttcgcgc caagaaggca gaggagctgg   1800
atcttcagtc gacagaaatc actggggagg aggagctggg ttcccgggag gactcgccca   1860
tgtcaccctc agacacccaa gaccagaaac ggacccgag gccgcaagt agacacggcc    1920
actcggtggt tgctcccggc aggactgcag tgagggcccg gatgccagcg ctgccccgaa   1980
gggaaggcgt agataagcct ggcttttccc tggccacgca gccccgccca ggggcgcccc   2040
cctcggcttc ggcctctcct gcccaccacg cgtccaccca gggcacctct catcgtcctt   2100
ccctgcctgc cagcttgaat gacaacgact tggtggactc agacgaagat gagcgcgctg   2160
tgggctccct ccaccccaag ggcgccttcg cccagccccg ccagccctg tccccagcc    2220
gccagtcccc gtccagcgtt ctccgcgaca gaagctctgt gcaccccggc gcaaagccag   2280
cctcgccggc ccggaggacc ccccattcag gggccgcaga ggaagattcc agtgcctcag   2340
ccccacccctc aagactttct ccaccccatg ggggatcatc tcggctgctg cccacccagc   2400
cacacctgag ctctccactt tccaagggcg ggaaggatgg tgaggacgcc ccagccacca   2460
actccaatgc gccatcacgg tccaccatgt cctcctccgt ctcttctcat ctctcgtcca   2520
ggacgcaggt ctctgaggga gcggaggctt ctgatggtga aagccacggt gacggcgata   2580
gggaagacgg cggaaggcag gcggaggcca cggcccagac gctgcgggcc cggcctgcct   2640
ctggacactt ccatttgctc agacacaaac cctttgctgc caacgggagg tctccaagca   2700
ggttcagcat tgggcgggga cctcggctgc agccctccag ctccccacag tcgactgtgc   2760
cctcccgagc ccacccagg gttccctctc actctgattc ccaccctaag cttagctcag   2820
gtatccatgg agacgaggag gatgagaagc cgcttcctgc caccgttgtc aatgaccacg   2880
tgccttcctc ctccaggcag cccatctccc ggggctggga ggacttaagg agaagcccgc   2940
agagagggc cagcctgcat cggaaggaac ccatcccaga gaaccccaaa tccacagggg   3000
cagatacaca tcctcagggc aagtactcct ccctggcctc caaggctcag gatgttcaac   3060
agagcacaga cgcggacacg gagggtcatt ctcccaaagc acagccaggg tccacagacc   3120
gccacgcgtc ccctgctcgt ccgcccgcag cacggtcaca gcagcatccc agtgttccca   3180
```

```
gaaggatgac acccggccgg gccccacaac agcagccccc tcctcccgtc gccacgtccc    3240
agcaccaccc gggaccccag agcagagacg cgggtcggtc accttcccag cccaggctct    3300
cactgaccca ggccgggcgg ccccgcccca cgtcgcaggg ccgctcccac tcctcctcgg    3360
acccttacac ggcgagctcc agagggatgc tccccacggc cctccagaac caggacgagg    3420
atgcccaggg cagctacgac gacgacagca cagaagtcga ggcccaggat gtgcgggccc    3480
ccgcgcacgc cgcgcgcgcc aaggaggcag ctgcgtccct tcccaagcac cagcaggtgg    3540
agtctcccac aggcgcaggg gcaggtggcg accacaggtc ccagcgcgga catgcggcct    3600
cccccgccag gcccagccga cccggcgccc ccagtcccg cgcccgggta cccagcaggg    3660
cagcgccggg gaagtcggag cctccttcca agcggcccct gtcctccaag tcccagcagt    3720
cggtctcagc cgaggacgac gaggaggagg acgcgggatt ttttaaaggc gggaaagaag    3780
accttctgtc ttcctctgtg ccaaagtggc cctcttcctc cactcccagg ggcggcaaag    3840
acgccgatgg gagcctcgcc aaggaagaga gggagcctgc catcgcgctt gcccctcgcg    3900
gagggagcct ggctcctgtg aagcgacctc tccccccacc tccaggcagc tcccccaggg    3960
cctcccacgt cccttcccga ctgccgcctc gcagcgctgc caccgtgagc cccgtcgcgg    4020
gcacccaccc ctggccgcag tacaccacgc gcgcccacc tggccacttc tccaccaccc    4080
cgatgctgtc cttgcgccag aggatgatgc atgccagatt ccgtaaccct ctctcccgac    4140
agcctgccag accctcttac agacaaggtt ataatggcag accaaatgta aagggaaag    4200 tccttcctgg tagtaatgga aaccgaatg acagagaat tatcaatggc cctcaaggaa    4260
caaagtgggt tgtggaccttt gatcgtgggt tagtattgaa tgcagaagga aggtacctcc    4320
aagattcaca tggaaatcct cttcggatta aactaggagg agatggtcga accattgtag    4380
atctggaagg gaccccgtg gtgagtcctg acggcctccc actctttggg caggggcgac    4440
atggcacacc tctggccaat gcccaagata agccaatttt gagtcttgga ggaaagccgc    4500
tggtgggctt ggaggtcatc aaaaaaacca cccatccccc taccactacc atgcagccca    4560
ccactactac gacgcccctg cctaccacta caaccccgag gcccaccact gccaccaccc    4620
gccgcacgac caccacccgc cgcacgacca ccaggcgtcc aacaaccaca gtccgaacca    4680
ctacgcggac aaccaccacc accaccccca cacccaccac tcccatcccc acctgtcccc    4740
ctgggacctt ggaacggcac gacgatgatg gcaacctgat aatgagctcc aatgggatcc    4800
cagagtgcta cgctgaagaa gatgagttct caggcttgga gactgacact gcagtaccta    4860
cggaagaggc ctacgttata tatgatgaag attatgaatt tgagacgtca aggccaccaa    4920
ccaccactga gccttcgacc actgctacca caccgagggt gatcccagag gaaggcgcca    4980
tcagttcctt tcctgaagaa gaatttgatc tggctgaag gaaacgattt gttgctcctt    5040
acgtgacgta cctaaataaa gacccatcag ccccgtgctc tctgactgat gcactggatc    5100
acttccaagt ggacagcctg gatgaaatca tccccaatga cctgaagaag agtgacctgc    5160
ctccccagca tgctccccgc aacatcaccg tggtggccgt ggaaggttgc cactcatttg    5220
tcattgtgga ctgggacaaa gccacccag gagatgtggt cacaggttac ttggtttaca    5280
gtgcatccta tgaagacttc atcaggaaca agtggtccac tcaagcttca tcagtaactc    5340
acttgcccat tgagaaccta aagcccaaca cgaggtatta ttttaaagtg caagcacaaa    5400
atcctcatgg ctacgaccct atcagccctt cggtctcatt tgtcaccgaa tcagataatc    5460
ctctgcttgt tgtgaggccc ccaggcggtg agcctatctg gatcccattc gctttcaaac    5520
```

```
-continued atgatcccag ctacacggac tgccatggac ggcaatatgt gaagcgcacg tggtatcgaa    5580
agttcgtggg agttgttctt tgtaattcac tgaggtataa aatctacctc agtgacaacc    5640
tgaaagatac attctacagc attggagaca gctggggaag aggtgaagac cattgccaat    5700
ttgtggattc acaccttgat ggaagaacag ggcctcagtc ctatgtagaa gccctcccta    5760
ctattcaagg ctactatcgc cagtatcgtc aggagcctgt caggtttggg aacatcggct    5820
tcggaacccc ctactactat gtgggctggt acgagtgtgg ggtctccatc cctggaaagt    5880
ggtaatcaca ggaccgtcat gctgcaagct tgccctgccc agccccacca actaagtcgc    5940
actaggggct gtgagcaaag acagccagcg tgctcagccc cgctgcccta ggtgccagga    6000
aggtcataga tggacactgg ccattctggt catctcagtc tggaactcag tcccacttct    6060
tggcctggac aatgaacagg attcagtttt gctgttaact ttgcttctct actttttttt    6120
gtttgtttgt aatagcacat cccagagaca tcagaaacca gcaactgatt cagtgtgatt    6180
tccagacttt ttaggcatga aattcggaca cttcagtatt tccaggaata gcatatgcac    6240
gctgttcttg cttcatggaa tgctacatgc tttctgtttt tctcattttg gatttctcca    6300
aaactaactg aatttaagct tcaggtccct ttgtatgcag tagaaaggaa ttattaaaaa    6360
caccaccaaa gaaaataaat atatcctact tgaaatttac tctatggact tacccactgc    6420
tagaataaat gtatcaaatc ttatttgtaa attctcaatt ttgatatata tatgtatata    6480
tgcatataca tatccacact tgtctgcaag aatattgatt aaaattgcta aatttgtact    6540
tgttcaccag aaaaaaaaaa aaaaaaaaaa aaaaaaa                              6578
```